United States Patent
Giavazzi et al.

(10) Patent No.: US 9,952,300 B2
(45) Date of Patent: Apr. 24, 2018

(54) DYNAMIC CONTRAST ENHANCED MRI METHOD AND AGENTS FOR THE ASSESSMENT OF THE MACROMOLECULAR TRANSPORT WITHIN PATHOLOGIC TISSUES

(71) Applicant: BRACCO IMAGING S.P.A., Milan (IT)

(72) Inventors: Raffaella Giavazzi, Milan (IT); Alessandro Maiocchi, Monza (IT); Michele Moschetta, Trani (IT); Giovanni Valbusa, Verbania (IT)

(73) Assignee: BRACCO IMAGING S.P.A., Milan (IT)

( * ) Notice: Subject to any disclaimer, the term of this patent is extended or adjusted under 35 U.S.C. 154(b) by 749 days.

(21) Appl. No.: 14/382,585

(22) PCT Filed: Mar. 5, 2013

(86) PCT No.: PCT/EP2013/054350
§ 371 (c)(1),
(2) Date: Sep. 3, 2014

(87) PCT Pub. No.: WO2013/131884
PCT Pub. Date: Sep. 12, 2013

(65) Prior Publication Data
US 2015/0050218 A1   Feb. 19, 2015

Related U.S. Application Data

(60) Provisional application No. 61/606,530, filed on Mar. 5, 2012.

(51) Int. Cl.
*G01R 33/56*   (2006.01)
*A61B 5/055*   (2006.01)
(Continued)

(52) U.S. Cl.
CPC .......... *G01R 33/5601* (2013.01); *A61B 5/055* (2013.01); *A61K 49/085* (2013.01); *A61K 49/10* (2013.01); *A61K 49/106* (2013.01)

(58) Field of Classification Search
CPC .. G01R 33/5601; A61B 5/055; A61K 49/106; A61K 49/085; A61K 49/10
See application file for complete search history.

(56) References Cited

U.S. PATENT DOCUMENTS 7,128,895 B2 * 10/2006 Cavagna ............... A61K 49/085
                                                            424/1.45
8,195,275 B2 *  6/2012 Zwick .................. A61B 5/0515
                                                            382/128
(Continued)

FOREIGN PATENT DOCUMENTS

EP    0806968 A2   11/1997
EP    1904460 A1    4/2008
(Continued)

OTHER PUBLICATIONS

Preda et al. "Dynamic contrast-enhanced MRI using macromolecular contrast media for monitoring the response to isolated limb perfusion in experimental soft-tissue sarcomas." MAGMA (Oct. 10, 2004) 17:296-302.*
(Continued)

*Primary Examiner* — Long V Le
*Assistant Examiner* — Angela M Hoffa
(74) *Attorney, Agent, or Firm* — Vivicar Law, PLLC

(57) ABSTRACT

The present invention generally relates to paramagnetic contrast agents and a Dynamic Contrast Enhanced-MRI method for the non-invasive estimation of the delivery of a macromolecular anticancer drug or pro-drug within pathological tissues and, especially, in solid tumors and for the optimization of anticancer therapies.

8 Claims, 8 Drawing Sheets

(51) Int. Cl.
A61K 49/08 (2006.01)
A61K 49/10 (2006.01)

(56) References Cited

U.S. PATENT DOCUMENTS

| | | | | |
|---|---|---|---|---|
| 8,200,312 | B2* | 6/2012 | Degani | A61B 5/03 600/420 |
| 2002/0151787 | A1* | 10/2002 | Bjornerud | A61K 49/1863 600/420 |
| 2003/0103904 | A1* | 6/2003 | Cavagna | A61K 49/085 424/9.365 |
| 2007/0059246 | A1 | 3/2007 | Cavagna et al. | |
| 2008/0294035 | A1 | 11/2008 | Zwick et al. | |
| 2009/0220432 | A1* | 9/2009 | Artemov | A61K 49/0041 424/9.34 |
| 2009/0264734 | A1* | 10/2009 | Degani | A61B 5/03 600/420 |
| 2010/0284927 | A1* | 11/2010 | Lu | A61K 49/16 424/9.2 |

FOREIGN PATENT DOCUMENTS

| | | |
|---|---|---|
| JP | 2003-531870 | 10/2003 |
| WO | 1995-032741 A1 | 12/1995 |
| WO | 1996-023526 A2 | 8/1996 |
| WO | 2000-037738 A1 | 6/2000 |
| WO | 2000-038738 A1 | 7/2000 |
| WO | 01/82974 | 11/2001 |
| WO | 2003-008390 A1 | 1/2003 |
| WO | 2006-023658 A2 | 3/2006 |
| WO | 2006-136564 A1 | 12/2006 |
| WO | 2008-071679 A1 | 6/2008 |
| WO | 2009-055542 A1 | 4/2009 |

OTHER PUBLICATIONS

Padhani, Anwar R. "Dynamic Contrast Enhanced MRI in Clinical Oncology: Current Status and Future Directions." J MRI (2002) 16:407-422.*

Jackson et al. "Imaging Tumor Vascular Heterogeneity and Angiogenesis using Dynamic Contrast-Enhanced Magnetic Resonance Imaging." Clin Cancer Res (Jun. 15, 2007) 13(12): 3449-3459.*

Turkbey et al. "Imaging of Tumor Angiogenesis: Functional or Targeted?". AJR Am J Roentgenol (Aug. 2009) 193(2): 304-313.*

Choyke et al. "Functional Tumor Imaging with Dynamic Contrast-Enhanced Magnetic Resonance Imaging". J MRI (2003) 17:509-520.*

Office Action for Chinese application No. 201380012698.2, dated Jan. 26, 2016 (English translation) [B0658 CN].

Abramoff, Michael D. et al., "Image Processing witih ImageJ", Biophotonics International, vol. 11, No. 7, 2004, Laurin Publishing Co. Inc., pp. 36-42.

Barrett, Tristan et al., "Macromolecular MRI contrast agents for imaging tumor angiogenesis", European Journal of Radiology, Elsevier Science, NL, vol. 60, No. 3, Dec. 1, 2006, pp. 353-366, XP028004637, ISSN: 0720-048X.

Boschi, Federico et al., "Tumor microvasculature observed using different contrast agents: a comparison between Gd-DTPA-Albumin and B-22956/1 in an experimental model of mammary carcinoma", Magnetic Resonance Materials in Physics, Biology and Medicine, Chapman and Hall, London, GB, vol. 21, No. 3, Mar. 4, 2008, pp. 169-176, XP019596834, ISSN: 1352-8661.

Bowers, William F. et al., "Ultrafiltration vs Equilibrium Dialysis for Determination of Free Fraction", Clinical Pharmacokinetics, vol. 9 (Suppl. 1), 1984, pp. 49-60, ADIS Press Limited.

Bronstad, Aurora, et al., "Effects of the taxanes paclitaxel and docetaxel on edema formation and interstitial fluid pressure", AJP-Heart Circ Physiol, vol. 287, www.ajpheart.org, 2004, pp. H963-H968.

Daldrup, Heike et al., "Correlation of Dynamic Contrast-enhanced MRI Iimaging with Histologic Tumor Grade: Comparison of Macromolecular and Small-Molecular Contrast Media", AJR, vol. 171, 1998, pp. 941-952.

De Haen, Christoph et al., "Gadocoletic Acid Trisodium Salt (B22956/1) A New Blood Pool Magnetic Resonance Contrast Agent With Application in Coronary Angiography", Investigative Radiology, vol. 41, No. 3, 2006, Lippincott Williams & Wilkins, pp. 279-291.

Eldredge, Harriet B., et al., "Species Dependence on Plasma Protein Binding and Relaxivity of the Gadolinium-Based MRI Contrast Agent MS-325", Investigative Radiology, vol. 41, No. 3, 2006, pp. 229-243.

Faccioli-N-et al., "Pathological animal models in the experimental evaluation of tumour microvasculature with magnetic resonance imaging", Radiologia Medica 200704, IT., vol. 112, No. 3, Apr. 2007, pp. 319-328, XP002699081, ISSN: 0033-8362.

Fang, Jun et al., "The EPR effect: Unique features of tumor blood vessels for drug delivery, factors involved, and limitations and augmentation of the effect", Advanced Drug Delivery Reviews, vol. 63, www.elsevier.com, 2011, pp. 136-151.

Franiel, T. et al., "Pharmacokinetic MRI of the Prostate: Parameters for Differentiating Low-Grade and High-Grade Prostate Cancer", Fortschr Rontgenstr, vol. 181, 2009, pp. 536-542.

Freeman, Daniel J. et al., "Tumor penetration and epidermal growth factor receptor saturation by panitumumab correlate with antitumor activity in a preclinical model of human cancer", Molecular Cancer, 2012 11:47, http://www.molecular-cancer.com/content/11/1/47, pp. 1-11.

Haacke, E. Mark et al., Magnetic Resonance Imaging: Physical Principles and Sequence Design, Ch. 22: Spin Density, T1 and T2 Quantification Methods in MR Imaging, pp. 637-667, John Wiley & Sons, Inc., 1999, ISBN 0-471-35128-8.

Hobbs, Susan K. et al., "Regulation of transport pathways in tumor vessels: Role of tumor type and microenvironment", Proc. National Academy of Sciences, vol. 95, 1998, Medical Sciences, pp. 4607-4612.

Jain, Rakesh K., "Transport of Molecules, Particles and Cells in Solid Tumors", Annu. Rev. Biomed. Eng. vol. 1, 1999, pp. 241-263.

Jain, Rakesh K. et al., "Delivering nanomedicine to solid tumors", Nat Rev Clin Oncol, vol. 7, No. 11, Macmillan Publishers Limited, 2010, pp. 653-664.

Lee, Carol M. et al., "The distribution of the therapeutic monoclonal antibodies cetuximab and trastuzumab within solid tumors", BMC Cancer, vol. 10, No. 255, 2010, BioMed Central Ltd., pp. 1-11.

Maeda, Hiroshi et al., "SMANCS and polymer-conjugated macromolecular drugs: advantages in cancer chemotherapy", Advanced Drug Delivery Reviews, vol. 46, 2001, pp. 169-185, ELSEVIER Science B.V.

Maki, Shojiro et al., "Image Enhancement in Computerized Tomography for Sensitive Diagnosis of Liver Cancer and Semiquantitation of Tumor Selective Drug Targeting With Oily Contrast Medium", Cancer, vol. 56, No. 4, 1985, pp. 751-757.

Marcucci, Fabrizio et al., "How to improve exposure of tumor cells to drugs—Promoter drugs increase tumor uptake and penetration of effedtor drugs", Advanced Drug Delivery Reievws, vol. 64, www.elsevier.com, 2011, pp. 53-68.

Matsumura-Yasuhiro et al., "A New Concept for Macromolecular Therapeutics in Cancer Chemotherapy: Mechanism of Tumoritrophic Accumulation of Proteins and the Antitumor Agent Smancs", Cancer Research, vol. 46, 1986, pp. 6387-6392.

Murase, Kenya, "Efficient Method for Calculating Kinetic Parameters Using T1-Weighted Dynamic Contrast-Enhanced Magnetic Resonance Imaging", Magnetic Resonance in Medicine, vol. 51, 2004, pp. 858-862.

Northfelt, Donald W. et al., "Pegylated-Liposomal Doxorubicin Versus Doxorubicin, Bleomycin, and Vincristine in the Treatment of AIDS-Related Kaposi's Sarcoma: Results of a Randomized Phase III Clinical Trial", Journal of Clinical Oncology, vol. 16, No. 7, Jul. 1998, pp. 2445-2451.

O'Brien, Mary E.R. et al., "Reduced cardiotoxicity and comparable efficacy in a phase III trial of pegylated liposomal doxorubicin HCI

(56) References Cited

OTHER PUBLICATIONS (CAELYX™/Doxi®) versus conventional doxorubicin for first-line treatment of metastatic breast cancer", Annals of Oncology, vol. 15, 2004, pp. 440-449.
PCT international Search Report for PCT/EP2013/054350, dated Jun. 28, 2013.
PCT Written Opinion for PCT/EP2013/054350, dated Jun. 28, 2013.
Preda, Anda et al., "MRI Monitoring of Avastin(TM) Antiangiogenesis Therapy Using B22956/1, a New Blood Pool Contrast Agent, in an Experimental Model of Human Cancer", Journal of Magnetic Resonance Imaging, vol. 20, No. 5, Nov. 1, 2004, pp. 865-873, XP055067230, ISSN: 1053-1807.
Primeau, Andrew J. et al., "The Distribution of the anticancer Drug Doxorubicin in Relation to Blood Vessels in Sold Tumors", Clinical Cancer Research, vol. 11, No. 24, 2005, www.aacrjournals.org, pp. 8782-8788.
Raatschen, H.J. et al., "Effects of MRI-Assayed Microvascular Permeability on the Accumulation of Vinorelbine in Xenograft Tumors", Experimentelle Radiologie, In Fortschr Rontgenstr, vol. 182, 2010, pp. 133-139.
Roberts, Caleb et al., "Comparative Study into the Robustness of Compartmental Modeling and Model-Free Analysis in DCE-MRI Studies", Journal of Magnetic Resonance Imaging, vol. 23, Wiley-Liss, Inc., 2006, pp. 554-563.
Roberts, Heidi C. et al., "Comparison of Albumin-(Gd-DTPA)30 and Gd-DTPA-24-Cascade-Polymer for Measurements of Normal and Abnormal Microvascular Permeability", JMRI, vol. 7, No. 2, 1997, pp. 331-338.
Stern, M. et al., "Overview of monoclonal antibodies in cancer therapy: present and promise", Clinical Reviews in Oncology Hematology, vol. 54, 2005, www.elsevier.com, pp. 11-29.
Taghian, Alphonse G., et al., "Paclitaxel Decreases the Interstitial Fluid Pressure and Improves Oxygenation in Breast Cancers in Patients Treated With Neoadjuvant Chemotherapy: Clinical Implications", Journal of Clinical Oncology, vol. 23, No. 9, 2005, pp. 1951-1961.
Thurber, Greg M. et al., "Antibody tumor penetration: Transport opposed by systemic and antigen-mediated clearance", Advanced Drug Delivery Reviews, vol. 60, www.elsevier.com, 2008, pp. 1421-1434.
Tofts, Paul S. et al., "Estimating Kinetic Parameters From Dynamic Contrast-Enhanced T1-Weighted MRI of a Diffusable Tracer: Standardized Quantities and Symbols", Journal of Magnetic Resonance Imaging, vol. 10, 1999, pp. 223-232.
Tong, Ricky T. et al., "Vascular Normalization by Vascular Endothelial Growth Factor Receptor 2 Blockade linduces a Pressure Gradient Across the Vasculature and Improves Drug Penetration in Tumors", Cancer Research, vol. 64, 2004, pp. 3731-3736.
Toutain, P.L. et al., "Plasma terminal half-life", J. vet. Pharmacol. Therap., vol. 27, Blackwell Publishing Ltd., 2004, pp. 427-439.
Whitlam, John B. et al., "Ultrafiltration in Serum Protein Binding Determinations", Journal of Pharmaceutical Sciences, vol. 70, No. 2, Feb. 1981, pp. 146-150, American Pharmaceutical Association.
Yankeelov, Thomas E. et al., "Quantitative pharmacokinetic analysis of DCE-MRI data without an arterial input function: a reference region model", Magnetic Resonance Imaging, vol. 23, www.sciencedirect.com, 2005, pp. 519-529.
Zheng, Jie, et al., "Accuracy of T1 Measurements at High Temporal Resolution: Feasibility of Dynamic Measurement of Blood T1 After Contrast Administration", Journal of Magnetic Resonance Imaging, vol. 10, 1999, pp. 576-581.
Office Action for Japanese application No. 2014-560326, dated Jul. 26, 2016 (English translation) [B0658 JP].
Office Action for Australian application No. 2013229631, dated Jun. 22, 2017.
Office Action for Australian application No. 2013229631, dated Nov. 11, 2016.
Office Action for Chinese Application No. 201380012698.2, dated Dec. 12, 2016 (English translation).
Office Action for Japanese application No. 2014-560326, dated Apr. 11, 2017 (English translation).

\* cited by examiner

DYNAMIC CONTRAST ENHANCED MRI METHOD AND AGENTS FOR THE ASSESSMENT OF THE MACROMOLECULAR TRANSPORT WITHIN PATHOLOGIC TISSUES

CROSS-REFERENCE TO RELATED APPLICATIONS

This application is the national stage application of corresponding international application number PCT/EP2013/054350, filed Mar. 5, 2013, which claims priority to and the benefit of U.S. application No. 61/606,530, filed Mar. 5, 2012, all of which are hereby incorporated by reference in their entirety.

FIELD OF THE INVENTION

The present invention generally relates to a dynamic contrast enhanced MRI (DCE-MRI) procedure for the assessment of the macromolecular transport within pathologic tissues.

More particularly, the invention relates to contrast agents and a DCE-MRI method for the non-invasive estimation of the delivery of macromolecular drugs or pro-drugs within pathological tissues and, especially, in cancerous areas and solid tumors, and for the selection and the optimization of anticancer therapies.

STATE OF THE ART

Cancer remains the major cause of death in advanced countries and cancer risk increases with increasing age of the population. Surgical removal, particularly in the case of small malignancies, or confined to a limited area, and conventional chemotherapy, commonly making use of small molecular drugs, still represent the most commonly used anticancer therapies.

Because of their lack of selectivity for the region and pathology to be treated and, thus, of the severe side effect caused by conventional chemotherapeutic agents, an increasing interest exists in bioactive agents having optimized targeting capabilities that can both greatly reduce the drug toxicity and improve the therapeutic efficacy granted by conventional chemotherapy.

Suitable examples include targeted agents, namely drugs comprising in their structure a selective tumor-targeting unit, typically a peptidic or peptidomimetic moiety, aimed at selectively directing the therapeutically active moiety to the tumor. However, this type of drug has not proved to be always effective and, in some cases, have even caused serious side effects. A different strategy, gaining increasing interest in the recent years, is based on the exploitation of large macromolecular or nano-sized drugs, namely therapeutic compounds having molecular weight larger than 40 KDa or based on particles with size ranging from 2 to 400 nm, which have proved superior therapeutic efficacy with minimal side effects in both preclinical and clinical settings. Macromolecular drugs or pro-drugs have, in fact, proven to spontaneously and selectively concentrate overtime in malignant tissues and, especially, within solid tumors, as a consequence of anatomical and pathophysiological abnormalities characterizing their structure and, especially, their vasculature. To this extent, it is worth remembering that the angiogenesis causes, in the majority of pathological tissues and solid tumors, the formation of chaotic and up-regulated blood vessels which typically display a significantly enhanced permeability that, along with other functional abnormalities, results in the extensive leakage of macromolecular compounds into extravascular tumor tissue. At the same time, local deficiencies or, even, the lack of reticuloendothelial and/or lymphatic clearance ensure to the said macromolecular compounds a long retention within tumor tissues, resulting, in case of macromolecular drugs, in a prolonged local therapeutic activity (see, for instance, Proc. Natl. Acad. Sci. U.S.A. 95, 1998, 4607-4612; R. K. Jain, Transport of molecules, particles and cells in solid tumors, Annu. Rev. Biomed. Eng., 1, 1999, 241-263). As an example, the spontaneous accumulation of anticancer drugs such as SMANCS (polymer conjugated of neocarzinostatin and poly(styrene-co-maleic acid) having molecular weight larger than 40 KDa) within tumor tissues has proven to be up to 200 times higher than that observed in normal tissues and organs (see for instance: Maeda et al., Cancer Res. 1986; 46, 6387-6392; Maeda et al., Adv. Drug Deliv. Rev. 2001; 46, 169-185).

This accounts for the increasing interest devoted in the last 10 years to therapeutic strategies making use of polymeric or nano-sized drugs, some of them have, indeed, achieved a rapid approval for clinical use and are already on the market, while many others are expected in the very soon. Cases of failure or limited effectiveness as well as of drug resistance over months of treatment have been, however, encountered, especially with nano-sized drugs (see, for instance, Northfelt, D. W. et al. Pegylated-liposomal doxorubicin versus doxorubicin, bleomycin, and vincristine in the treatment of AIDS-related Kaposi's sarcoma: results of a randomized phase III clinical trial. J. Clin. Oncol. 16, 1998, 2445-2451; O'Brien, M. E. et al. Reduced cardiotoxicity and comparable efficacy in a phase III trial of pegylated liposomal doxorubicin HCl (CAELYX/Doxil) versus conventional doxorubicin for first line treatment of metastatic breast cancer. Ann. Oncol. 15, 2004, 440-449).

An explanation for these failures most probably lies in the peculiar anatomy and pathophysiology displayed by the different cancerous tissues. To this extent, it is in fact clear that, in order to effectively exert its therapeutic action in a pathological tissue a drug must be able to reach the concerned tissue through the blood circulation system, extravasate from vessels, and deeply diffuse in the extravascular-extracellular space of the tissue.

A number of scarcely or heterogeneously-perfused tumors are, instead, encountered in the clinical practice, which exhibit a resistance to pharmacological treatments with macromolecular anticancer drugs which is essentially due to the inadequate delivery thereof within the pathological area or tissue to be treated. Among them are, for instance, larger or later-stage solid tumors, often comprising an external layer typically displaying more dense and hyper-permeable microvascularisation, and an internal core, commonly including necrotic areas scarcely vascularised and hard to be penetrated by macromolecular therapeutic agents.

A phenomenon that considers and accounts for all the parameters facilitating the delivery and the accumulation of macromolecular solutes within a tumor mass is the Enhanced Permeability and Retention (EPR) effect, firstly reported and discussed by Maeda and co-workers (se Maeda et al., Cancer Res. 1986; 46, 6387-6392).

More particularly, the EPR effect is a complex molecular-weight dependent phenomenon which is related to the peculiar anatomy and pathophysiology of the malignant tissue and its quantification would translate in a reasonably reliable estimate of the penetration and the accumulation of a macromolecular solute within it. (see, in particular, Adv.

Drug Deliv. Rev. 2011; 63, 136-151 and cited literature). In practical terms, the higher is the observed EPR effect, the greater is the expected delivery of a macromolecular drug or pro-drug within the tumor. In contrast, if the observed EPR effect is too low, only a limited or inhibited drug penetration in the malignancy is expected, resulting in the so called drug-resistance of the tumor.

Accordingly, the EPR effect is today accepted by the scientific community as the key factor in the evaluation of a drug delivery into a tumor mass and, in turn, for the identification of patients showing limited or inhibited accessibility to pharmacological treatments with macromolecular drugs or pro-drugs, thus becoming the "gold standard" in the anticancer drug design and therapeutic strategies using macromolecular agents.

However, because of both the number and the complexity of parameters actually underlying and affecting this phenomenon (for instance detailed in formerly cited literature and, especially, Adv. Drug Deliv. Rev. 2011, 63, 136-151, herein incorporated by reference), an established method for the non-invasive in vivo quantization of the EPR effect by use of clinically relevant imaging techniques is still not available.

A histological method based on fluorescence microscopy was indeed suggested as a valuable tool to quantify blood perfusion and to characterize at the microscopic level the extravasation of a compound of interest from vessels to the extravascular space.

Suitable agents for use in this method are fluorescent compounds, either fluorescent per se or because conjugated to a fluorophore group, allowing to measure their concentration through the fluorescence intensity that they promote in microscopic images.

An important parameter that can be calculated by this histological method is the vessels area, namely the percentage of a microscopic section occupied by vessels. To this extent, the higher is the value of this parameter, the better is the tumor perfusion and the improved is the transport of solutes into the tissue. Although vessels area is an important parameter to may establish the EPR effect through the penetration of the compound of interest into the tissues, the most interesting information obtainable with the fluorescence microscopy is the curve representing the decay of the compound concentration as a function of its distance from the nearest perfused vessel. This curve is obtainable by expressing the fluorescence intensity I measured from a number of microscopic images as a function of their distance from the nearest perfused vessel, namely as $I=f(x)$ (to this extent see, for instance, F. Tannock et al., 2005. Clin Cancer Res, 11, 8782-8788 and Tong, R. T. et al., 2004 Cancer Res, 64, 3731-3736).

Alternatively, the use of the Evans blue is also disclosed in the relevant literature, that is a blue-dye that, after intravenous injection, accumulates in certain tumor sites while not results in normal tissues.

However, due to the moderate sensibility of the involved technique, dyes can profitably be used only in ex vivo investigations carried out on samples obtained from sacrificed animals or in in vivo tests performed on tumors made surgically observable.

Radiolabelled agents have also been used to provide in vivo estimates of the macromolecular compounds accumulation within tumors by use of PET technique. This latter, however, beside requiring the exposition of the patient to dangerous radiation, only provides a poor spatial resolution, that is one order of magnitude lower than that obtained with MRI and, therefore, can hardly be exploited with small tumors.

A CT based procedure making use of an oily contrast medium, namely Lipiodol, has also been disclosed, in particular as a valuable medium for dissolving and, thus, selectively delivering anticancer drugs (see, for instance, Cancer, Aug. 15, 1985).

The assessment of the vascular permeability with DCE-MRI techniques through measures of the $K^{trans}$ obtained with B22956/1 (Gadocoletic acid trisodium salt) is disclosed, for instance, in the US 2007/0059246 patent Application.

The correlation between endothelial permeability (measured, by DCE-MRI technique, as coefficient of the permeability-surface area product, $K^{PS}$) and histologically determined concentration of the chemotherapeutic agent Vinorelbine in experimental xenograft tumors undergoing angiogenesis inhibition with bevacizumab (Avastin™) was analysed by Brasch et al. in Fortschr. Rontgenstr 2010; 182: 133-139.

In particular the article discusses the correlation observed between $K^{PS}$ values obtained in tumor rim with albumin $(Gd-DTPA)_{30}$, a macromolecular contrast enhancing agent (m.w.≅92 KDa) not authorized for clinical use because of the immunogenic response it raises (Brasch R. et al., JMRI 1997; 7:331-338), and the total, HPLC determined, concentration of chemotherapeutic agent within the examined tumor region, calculated without discriminating between the agent optionally still inside vascular compartment or diffused within extravascular-extracellular space of the concerned tumor area. For contrast, this kind of determination makes quite unfeasible the identification of substantially unreached or non-homogeneously perfused tumor areas.

Instead, in order to identify oncologic patients who may benefit from a treatment with a macromolecular anticancer drug or pro-drug it is necessary to be able to estimate the real possibility this latter has to penetrate and homogeneously permeate the diseased area to be treated by determining, as pivotal steps, the amount of the undergoing extravasation (from blood vasculature) and the depth and homogeneity of its diffusion in the extravascular space of pathologic area (Freeman et al. Molecular Cancer 2012; 11:47).

In this respect it is, indeed, worth remembering that the insufficient and/or non-heterogeneous distribution of the monoclonal antibodies (mAbs) based anticancer agents in a tumor region is currently acknowledged by the scientific community as one of the major cause of failure of treatments using mAbs derived drugs. The spatial distribution of the drug at the microscopic scale, especially the distance that a mAb can reach from the perfused vessels when administered systemically before it is cleared from the blood pool is, indeed, a determinant factor for the therapeutic efficacy of the mAbs.

A need, therefore, still exists for improved contrast agents and diagnostic methods allowing the non-invasive verification of the existence in the pathologic tissue to be treated of those conditions permitting an effective delivery of macromolecular drugs, so as to discriminate resistant tumors and, hence, patients, who can hardly benefit from a therapeutic treatment using macromolecular drugs or pro-drugs due to an insufficient or impaired distribution thereof in the tissue to be treated.

SUMMARY OF THE INVENTION

The solution that the present invention discloses relates to paramagnetic contrast agents and to a diagnostic method allowing to non-invasively in vivo estimate the permeability of a pathological tissue to a macromolecular compound of interest by use of MRI techniques.

More particularly, the invention relates to a class of paramagnetic contrast agents and a MRI method for the non-invasive assessment of either the conditions underlying the extravasation and diffusion of a macromolecular solute of interest and the quantitative evaluation of its delivery into a pathological body area, region, tissue, tumor or cancerous mass or, more generally, in an inflamed area, based on the pharmacokinetics these agents display in the said concerned area.

To this extent, a class of paramagnetic contrast agents has been identified that, despite of having a reasonably low molecular weight, have proven to follow in vivo, for a time widely compatible with the time of the MRI diagnostic imaging, the same pharmacokinetic fate of the Human Serum Albumin (HSA), a blood macromolecular solute having molecular weight about 67 KDa.

In particular, we have observed that paramagnetic contrast agents having molecular weight lower than 5,000 Dalton and displaying an in vivo non-covalent binding with HSA of at least 85% show, in human plasma, pharmacokinetics strictly comparable to that of the Human Serum Albumin for a suitable time, i.e. for a time widely compatible with the MRI imaging, and are able to provide reliable estimates of the delivery of this latter and its distribution into a pathologic body area or tissue of interest based on the pharmacokinetics they display in the said concerned area or tissue, as assessed by use of MRI-imaging techniques.

Interestingly, moreover, through providing an in vivo quantization of the local delivery of the HSA, conveniently considered as a representative example of a macromolecular solute of interest, these contrast agents have advantageously proven to be in turn able to provide a reliable assessment of the conditions underlying the extravasation and diffusion of a macromolecular solute of interest such as a drug or pro-drug and, even more interestingly, a quantitative evaluation of its delivery into a diseased body area or tissue and, especially, in a tumor or cancerous mass.

Accordingly, in one embodiment the present invention relates to the use of this class of non-covalent HSA binding contrast agents to non-invasively in vivo estimate the delivery of a macromolecular solute of interest in a pathologic body area, tissue or mass, and the extent of the local macromolecular transport by MRI imaging techniques.

In another embodiment the present invention relates to a DCE-MRI method that comprises non-invasively obtaining an in vivo assessment of the delivery of a macromolecular solute of interest into a pathologic body area, region, tissue or solid mass from the pharmacokinetic displayed by a suitable paramagnetic contrast agent in the said concerned pathologic tissue, region or mass, and, more particularly, from DCE-MRI estimates of parameter(s) related to the pharmacokinetic this agent display in that concerned body area or mass.

In a different embodiment, the present invention relates to the use of paramagnetic agents and DCE-MRI method according to the invention for identifying penetration-resistant tumors, i.e. pathological tissues exhibiting a poor or impaired permeability to macromolecular solutes that can, thus, hardly benefit from treatment with macromolecular anticancer drugs or pro-drugs.

In a further embodiment the invention relates to a diagnostic protocol for the stratification of oncologic patients which makes use of the agents and the DCE-MRI method of the invention for identifying and discriminating patients resistant to an anticancer therapy relying on the use of macromolecular drug(s) or pro-drug(s) due to their insufficient or impaired penetration in the tumor area to be treated.

Still in addition the invention further relates to the use of agents and DCE-MRI method of the invention for the selection, the management and the optimization of an anticancer strategy using macromolecular anticancer drugs or pro-drugs, alone or combined with other synergistic agents including any agent devoted to enhance the uptake of macromolecular drugs such as, for instance, EPR enhancing agents, as well as for monitoring the effectiveness of EPR enhancing therapies or combined therapies including both anticancer and EPR enhancing drugs or for testing the efficacy, in terms of optimal delivery, of new anticancer drugs or pro-drugs within pathologic tissues of interest.

DETAILED DESCRIPTION OF THE INVENTION

Figure 1:
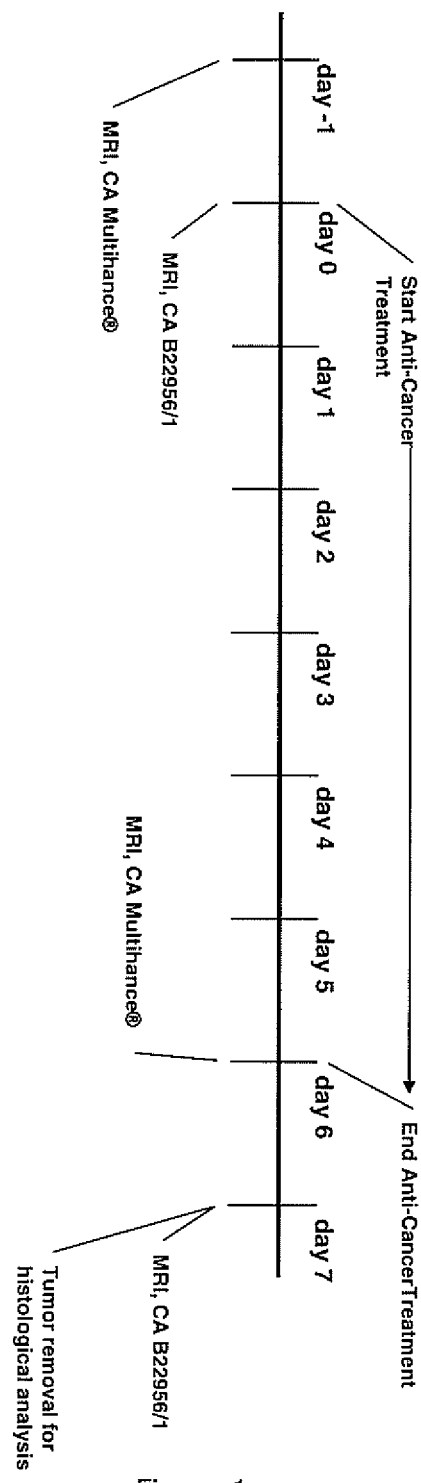
FIG. 1. Timing of the in vivo tests of Example 3 using Gadocoletic acid sodium salt in mice.

The invention relates to a DCE-MRI method of general applicability for non-invasively obtaining estimates of the conditions related to the penetration and the diffusion of a macromolecular solute or, in other words, its transport within a pathologic tissue or mass, as well as a quantitative assessment of its local delivery, based on the pharmacokinetic displayed by a suitable class of paramagnetic contrast agents in the said concerned pathologic area or tissue.

The proposed method, therefore, permits the non-invasive discrimination of tumors and patients where delivery conditions underlying the extravasation and the diffusion of macromolecular solutes are suitably met from patients destined to display a resistance to pharmacological treatments with macromolecular anticancer drugs due to the inadequate delivery thereof in the pathological tissue to be treated.

In particular, an object of the present invention is a DCE-MRI method for the non-invasive assessment of the macromolecular transport into a pathologic body area, tissue or mass that comprises obtaining in vivo estimates of the local delivery of a macromolecular solute of interest from the pharmacokinetics displayed by a suitable class of paramagnetic contrast agents in the said concerned pathologic area or tissue or, more particularly, from DCE-MRI estimates of those parameters related to the pharmacokinetics these agents display in that concerned tissue, area or mass.

To this extent, the Dynamic Contrast Enhanced MRI technique (DCE-MRI) is an emerging diagnostic imaging technique currently considered as optimal to quantify pharmacokinetic parameters in various tissues and to evaluate the progression of the response to cancer treatments, especially with antiangiogenic drugs (see, for instance, Preda et al. JMRI 2004; 20:865-873; Haacke E. M., Magnetic Resonance Imaging 1999; Physical Principles and Sequence Design Wiley-Liss; and Fortschr. Röntgenstr 2009; 181: 536-542). Though its election should not be regarded as limiting or preclusive of the alternative use of different sequence sets or imaging protocols known in the MRI technical field, the use of the DCE-MRI technique to implement the method of the invention, namely to obtain estimates of parameters related to the pharmacokinetic displayed by the involved contrast agent within a concerned pathologic tissue or tumor mass, is considered as preferred.

Unless otherwise provided, with the term "delivery" (or "distribution" or "permeation" as herein used interchangeably), of a macromolecular solute within a concerned pathologic body region, tissue or tumor mass, we intend the extent of its distribution in the interstitial space of the concerned tissue or mass, which typically includes its extravasation from the blood circulation to the extravascular space and its local (namely interstitial) diffusion.

With the term "transport" of a macromolecular solute within a concerned body area, region, tissue or tumor mass, we intend, instead, the extent of its penetration in the said concerned area or mass, typically through the local vascularisation, and its diffusion in the interstitium of the concerned tissue or mass.

With "delivery conditions" we refer to those patho-physiological conditions and functional parameters underlying the extravasation from the blood circulation and the diffusion of a macromolecular solute within the interstitium of a pathological tissue, for instance addressed and better detailed in the above cited literature (see, in particular, Adv. Drug Deliv. Rev. 2011, 63, 136-151, incorporated by reference).

With "pathologic" or "diseased" tissue, area, body region or solid mass we refer to an area affected by a pathology which may benefit from a treatment with macromolecular drugs or pro-drugs such as, preferably, a cancerous or tumor body area, tissue or region or a tumor mass or, more generally, a chronically inflamed area such as for instance, an arthritic area or body region.

With "patient" we intend a mammalian patient, and, preferably a human being suffering for a disease such as, for instance, a chronic inflammatory state, a cancer or a tumor, or, more generally, for a pathology which may benefit from therapeutic treatments with macromolecular drugs or pro-drugs.

Unless otherwise provided, macromolecular solutes within the scope of the present invention are compounds having a size comparable to or greater than that of albumin, i.e. having molecular weight at least around 50 KDa, or drugs such as anticancer drugs reaching the said dimensions upon intravenous injection, due to non-covalent binding with plasmatic proteins or blood components.

Macromolecular solutes of particular interest according to the invention are macromolecular drug or pro-drug, especially anticancer drugs or pro-drugs, typically including monoclonal antibodies or antibody fragments, or protein conjugates, or even polymer derivatives of therapeutic molecule.

Suitable examples, for instance, include polymeric conjugates of proteins such as SMANCS, PEG-asparaginase and PEGylated anti VEGFR2, conjugates of low molecular drugs with a synthetic polymer such as SMA (Styrene-Maleic acid/anhydride copolymer), HPMA (N-2-hydroxypropyl)-methacrylamide copolymer), DIVEMA (divinyl ether-maleic acid conjugate), PVA (polyvinyl alcohol), PEG (polyethylene glycol), succinyl gelatine, OXD (oxidized dextran 70) for instance including SOD-SMA (wherein SOD stands for superoxide dismutase), SOD-DIVEMA, DIVEMA-NCS (wherein NCS stands for neocarzinostatin), Pyran-NCS, SOD-PVA, SOD-suc-gelatin, PEG bilirubin oxidase, DOX-HPMA (wherein DOX stands for Doxorubicin), OXD-DOX, PEG-docetaxel (NKTR-105), PEG-irinotecan (NKTR-102), PEG-naloxone (NKTR-118), HPMA copolymer palatinate (ProLindac) and polymer-cyclodextrin nanoparticle-camptothecin (IT-101), or conjugates of low molecular drugs with proteins such as IgG or albumin, or, still moreover, drugs based on monoclonal antibodies or antibodies fragments, for instance disclosed in Critical Review in Oncology Hematology 2005; 54 11-29, and cited literature, as well as drugs displaying an in vivo non-covalent binding with plasma components, and, especially, albumin, of at least 90%. Preferred macromolecular drugs based on monoclonal antibody/antibody fragment for instance include Campath® (Antibody: Alemtuzumab; target: CD52), Avastin® (Antibody: Bevacizumab; target: the Vascular endothelial growth factor, VEGFR), Adcetris™ (Brentuximab Vedotin; target: CD30), Erbitux® (Antibody: Cetuximab; target: epidermal growth factor receptor), Mylotarg® (Antibody: Gemtuzumab; target CD33), Yervoy® (Ipilimumab or MDX-101; target: blocks CTLA-4), Vectibix® (Antibody: Panitumumab; target:epidermal growth factor receptor), Herceptin® (Antibody: Trastuzumab; target:HER2/neu), Bexxar® (Antibody: Tositumomab; target:CD20), Rituxan® (Antibody: Rituximab; target CD20).

In the method of the present invention the assessment of the macromolecular transport into a pathologic body area or tissue of interest is essentially obtained from the quantitative evaluation, performed by use of the DCE-MRI technique, of one or more of those parameters that are strictly related to the pharmacokinetics locally displayed by the exploited contrast agent, and that are, in turn, related to and, therefore, responsive for those peculiar anatomic and patho-physiologic conditions underlying the extravasation and the diffusion of the contrast agent in the said concerned tissue or area.

To this extent, many are the parameters that can be calculated from the DCE-MRI experimental data, and from the data generally obtainable in most clinical and preclinical set, and different are, moreover, pharmacokinetic (PK) approaches used to calculate them. Some of these methods and quantities are, for instance, listed in Tofts P. S. et al, JMRI, 1999; 10, 223-232 while an approach consenting their assessment is for instance described in Yankeelov T E et al. Magn. Reson. Imaging 2005; 23, 519-29.

A non-limiting list of suitable pharmacokinetic parameters according to the present invention, (otherwise generically identified as p), for instance, includes:

$K^{trans}$ (min$^{-1}$), which is the volume transfer constant between blood plasma and Extravascular Extracellular Space (EES). It is related to the extravasation of the concerned agent from the blood vasculature to the extravascular-extracellular (EES) space;

$f_{PV}$, the fractional plasma volume, which provides an indication of the volume of blood and, thus, of the local (tumor) vascularisation;

$K_{ep}$ (min$^{-1}$), which is the rate constant between EES and blood plasma, (more precisely, from the EES to the blood and, hence, to the wash out of the solute) and is related to the fraction of extravascular-extracellular space in tissue or region of interest;

$AUC_{t1,t2}$ (Area under the Curve, min×mol/L), which is the integral of the contrast agent concentration time profile. For instance, $AUC_{20,30}$ and $AUC_{10,20}$ are the AUC calculated between 20 to 30 minutes and 10 to 20 minutes post injection of the contrast agent;

$AUCE_{t1,t2}$ (Area under the signal Enhancement Curve, min), which is the integral of the MRI signal enhancement time profile. For instance, $AUCE_{20,30}$ and $AUCE_{10,20}$ are the AUCE calculated between 20 to 30 minutes and 10 to 20 minutes post injection of the contrast agent;

$IAUC_T$ (the Initial Area under the time-Concentration Curve, min×mol/L), which is the integral of the contrast agent concentration curve calculated over the first time point acquired after the contrast agent injection and a terminal time point T;

$IAUCE_T$ (the Initial Area under the time-signal Enhancement Curve (min), which is the integral of the signal enhancement curve calculated over the first time point acquired after the contrast agent injection and a terminal time point T;

AVGENH (the Average signal Enhancement, or Ave. Enh., as used herein interchangeably), which is the average signal enhancement calculated over all the time-points acquired post-injection;

EARLYAUCRATIO (or Early A U C Ratio, as used herein interchangeably), which is calculated dividing the $IAUC_1$ in the ROI of interest (for instance tumor, or muscle) by the $IAUC_1$ in blood (calculated during the first minute after contrast agent injection). For contrast agents having a negligible extravasation (from the vasculature) during the first minute after injection, as is the case of the agents according to the present invention, the value of the EARLYAUCRATIO is related to tumor fractional plasma volume;

LATEAUCRATIO (or Late AUC Ratio, as used herein interchangeably), which is calculated as the Area Under the Enhancement Curve in the region of interest from 20 to 30 minutes post injection ($AUC_{20,30}$) divided by $IAUC_1$ measured in blood. This quantity is related to the amount of extravasated Contrast Agent and thus, indirectly, to the values of $k^{trans}$ and $k_{ep}$.

Late and Early ENHANCEMENT are operationally different but substantially equivalent to (i.e. express the same quantity of) Late and Early AUCRATIO.

However, each pharmacokinetic parameter in some extent related to, or derivable from the above identified DCE-MRI pharmacokinetic parameters has to be considered as within the present invention.

In general terms, the main steps of the DCE-MRI procedure of the invention comprises: a) obtaining a collection of MRI images acquired during the passage of a suitable contrast agent within a pathological body area or region of interest and calculating the contrast agent concentration-time profile (or concentration-curve over the time, as used herein interchangeably) from acquired MRI images; b) extracting from the calculated concentration-time profiles the numerical descriptor(s) that are related to the pharmacokinetics displayed by the contrast agent within the pathologic tissue; and c) deriving an assessment of the macromolecular transport within the concerned tissue from the calculated parameter values. Critical point of the above procedure includes the identification of the Region of Interest within each of the collected DCEMRI images. With Region of Interest or ROI, as used herein interchangeably, we intend the body region (or the tissue, or the part of these same) on which the diagnostic method is applied i.e. the particular region of which the physiological characteristics relevant for the distribution of macromolecules at the tissue level are investigated. Typically, the region of interest (ROI) in the recorded images is represented by the pathologic region (typically the tumor region, or tumor ROI, as herein used interchangeably), but a reference region, for instance represented by healthy muscle, where the extravasation of the macromolecular solute of interest is substantially absent or at least negligible, and, optionally, a vessel area (or blood region) are also commonly identified for computational and/or comparative reasons.

According to a preferred implementation, the DCE-MRI method of the invention relies, essentially, on the pharmacokinetic modelling of the signal time curves acquired during DCE-MRI experiment, and comprises, as main steps:

i) obtaining a signal intensity curve from a collection of DCE-MRI images acquired during the passage of a suitable paramagnetic contrast agent within the pathologic area, tissue or mass under investigation and, optionally, an equivalent curve from a reference region and/or a vessel region, and converting the MRI signal intensities in contrast agent concentration and obtaining a concentration curve, ii) fitting the concentration curve by a pharmacokinetic model to obtain estimates of those pharmacokinetic parameters $p_i$ that are related to the transport of the contrast agent in the concerned tissue, area or mass, iii) assessing the delivery of a macromolecular solute of interest within the said concerned tissue or area under investigation from the obtained pharmacokinetic parameters values.

Preferably, the above DCE-MRI method further comprises acquiring morphologic MRI images of the pathologic body area or region under investigation, for instance before starting the dynamic imaging procedure, allowing to identify with good anatomical resolution the ROI(s) of interest, typically the tumor region(s), the reference region and, optionally, the blood region within recorded DCE-MRI images.

The collection of DCE-MRI images according to the step i) of the method can suitably be acquired over the whole acquisition time window (T) after contrast agent administration to the end point T of the MRI acquisition, typically ranging from 1 to 30 minutes or, preferably, in a time from 1 to 20 and, more preferably, from 1 to 15 minutes, or, alternatively, in any, continuous or discontinuous, time window comprised between the contrast agent administration and the end of the MRI acquisition.

Suitable examples of pharmacokinetic parameters that can be obtained at the step ii) of the method include the transfer constant $K^{trans}$, the rate constant $K_{ep}$, and the fractional plasma volume, $f_{PV}$.

However, though their election should not be regarded as limiting or preclusive of the estimation of any different parameter, a preferred implementation of the above method includes obtaining DCE-MRI-based estimates of $K^{trans}$ and $f_{PV}$, and, more preferably, of the $K^{trans}$, that are calculated by fitting the concentration curve obtained at the step i), typically by using a two compartment pharmacokinetic model known in the art, and for instance disclosed in Brasch R. C. et al., 1998, AJR 171,941-949, and Tofts P. S. et al, JMRI, 1999, 10, 223-232.

To this extent, a substantially linear correlation between DCE-MRI derived $K^{trans}$ values and the observed delivery of a macromolecular solute within the same imaged tissue, allows an assessment of the latter form DCE-MRI estimates of the former. In practical terms, the higher is the measured $K^{trans}$, the greater and/or the more homogeneous is the delivery of the macromolecular drug or pro-drug within the pathologic tissue under examination while, conversely, lower $K^{trans}$ estimates are suggestive of poor or impaired extravasation and diffusion of a macromolecular solute within the said tissue.

An alternative, but equally preferred implementation of the DCE-MRI method of the invention, is herein identified as model-free approach.

This approach is not based on the determination of those physiological parameters related to tumor vasculature; instead it is based on parameters that are related to the arrival of contrast agent in the tissue of interest, and that reflect blood flow, vascular permeability and the fraction of interstitial space (Geoffrey J. M. Parker et al. Comparative Study into the Robustness of Compartmental Modeling and Model-Free Analysis in DCE-MRI Studies. JMRI 2006, 23:554-563).

Essentially, this implementation relies on the extraction (from the MRI data acquired during DCE-MRI experiment) of numerical descriptor(s) such as, for instance, the value(s) of AUC and/or AUCE calculated over various time windows after the contrast agent injection and including, for example, the value(s) of the Initial Area Under the time-Concentration Curve ($IAUC_T$) and/or the Initial Area Under the time-signal Enhancement Curve $IAUCE_T$, calculated over several time windows limited by the first time point after the contrast agent injection and by various time points T (in minutes) before the end of the DCE-MRI acquisition, and/or the Average Signal Enhancement calculated, instead, over all the time-point acquired post injection.

More particularly, this alternative implementation comprises, as main step, calculating a contrast agent concentration (and/or, alternatively, a signal enhancement) curve covering the first T minutes after contrast agent injection from the set of MRI images acquired during the passage of the agent within the area or tissue of interest, for instance over the whole acquisition time window, typically taking, as formerly said, up to 30 minutes and, preferably, a time from 1 to 20 minutes or, alternatively, over a $t_1$ to $t_2$ time window, for instance from 20 to 30 minutes post injection, or even in any, continuous or discontinuous, time window comprised between the contrast agents administration and the end of the MRI acquisition, and/or the Average signal Enhancement, calculated over all the post injection time-points of the acquisition time window.

The integral of the contrast agent concentration (or signal enhancement) curve over the concerned time T from the agent administration, can be determined by using numerical integration procedures known in the art such as, for instance, the following trapezoidal integration rule $$IAUC_T = \frac{1}{2}\sum_{i=2}^{N} (t_i - t_{i-1})(F(i) + F(i-1))$$

where $IAUC_T$ is the IAUC calculated over the first T minutes post-injection, F(i) is the tissue concentration (or the signal enhancement for AUCE) of contrast agent at dynamic time point i, $t_i$ is the time at time point i, and N is the last time point before $t_i=T$, or the following equation:

$$AUC_{t1,t2} = \frac{1}{2}\sum_{i=t1}^{t2}(t_i - t_{i-1})(F(i) + F(i-1))$$

where AUC is calculated over the $t_1$ to $t_2$ time window (i.e., more precisely, by using all the DCE-MRI images acquired during the time-interval between t1 and t2) and F(i) is the tissue concentration of contrast agent (or the signal enhancement for AUCE) measured at time point i.

The AVEGH, can, instead be determined for instance by using the following equation $$AVGENH = \frac{\sum_{i=1}^{N} Enh(i)}{N}$$

where Enh(i) is the signal enhancement at dynamic time point i, and N is the last acquired time point.

Generally speaking, each of the above DCE-MRI descriptors AVGENH, AUC, AUCE, $IAUC_T$ $IAUCE_T$, as well as any other numerical descriptor which can be operationally derived from them, or from any operational combination thereof, and for instance including the LATEAUCRATIO and the EARLYAUCRATIO, can be suitably extracted from recorded DCE-MRI images by using this alternative implementation procedure according to the invention. However, though their election should not be regarded as limiting or preclusive of the estimation of any different parameter, a preferred implementation of the above method includes obtaining DCE-MRI-based estimates of at least one among AVGENH, AUC, and/or AUCE, or, alternatively of $IAUC_T$ and/or $IAUCE_T$, wherein these last are, as above said, a particular implementation of the previous; more preferably, the method includes extracting from the collected DCE-MRI images numerical estimates of AVGENH, because of its robustness and easy determination.

The two implementation methods formerly described, i.e. the pharmacokinetic modelled and the model-free approach, can be considered as alternatives to each other, because each of them provides, as a result, the determination of at least one pharmacokinetic parameter, respectively, for example, $K^{trans}$ and/or $f_{PV}$ (with the pharmacokinetic modelled approach) and AVEGH, $IAUC_T$ $IAUCE_T$, A U C, AUCE, LATEAUCRATIO and/or EARLYAUCRATIO (with the model-free approach), which is related to, and, therefore, responsive for the transport of the contrast agent within the pathologic tissue and is, in turn, able to provide an assessment of the delivery of a macromolecular solute of interest in the said concerned tissue. However, though the determination of more than one parameter should not be considered as a necessary limitation, a preferred implementation of the DCE-MRI method of the invention comprises measuring two or more or even all of the above pharmacokinetic parameters p and then comparing obtained results to provide more accurate and truthful estimation of the macromolecular delivery into a concerned body area or tissue under investigation.

Accordingly, in a particularly preferred embodiment, the present invention relates to a DCE-MRI method wherein a suitable paramagnetic contrast agent is used for obtaining in vivo estimates of the delivery of a macromolecular solute of interest into a pathologic body area, region, tissue or solid mass, the said method comprising, as main steps:
a) acquiring a collection of DCE-MRI images during the passage of the contrast agent within the concerned pathologic body area, tissue, region or mass, and, optionally, additional MRI images with good anatomical resolution; identifying the Region(s) of Interest, typically the tumor region(s), a reference region and, optionally, the vessel region within collected the DCE-MRI images, and obtaining a signal intensity curve within identified regions,
b) optionally determining the value of AVGENH and/or of AUCE in any, continuous or discontinuous, time windows comprised between the contrast agents administration and the end of the MRI acquisition,
c) converting the MRI signal intensity values obtained at the step a) in contrast agent concentration values and drafting a concentration-time curve,
d) optionally determining the value of AUC in any, continuous or discontinuous, time windows comprised between the contrast agents administration and the end of the MRI acquisition,
e) fitting the said obtained concentration curve by a pharmacokinetic model to obtain an estimate of $K^{trans}$,
f) assessing the delivery of the macromolecular solute of interest from the obtained estimate(s) of the assessed parameter(s).

To this extent, it is worth noting that the above method may optionally further comprise, before step a), a step 1a) concerning the administration of an effective amount of the elected paramagnetic contrast agent to a patient in need or to an organ or other body region or tissue of the said patient. In an alternative embodiment, the above method may, instead, comprise obtaining a signal intensity curve from a collection of MRI images acquired on a patient pre-treated with a proper amount of paramagnetic contrast agent, or, still alternatively, it can includes obtaining a signal intensity curve (and, in turn, estimates of at least one of the above DCE-MRI based parameters) from a collection of MRI images acquired, at the appropriate time, by a patient properly treated with an effective amount of paramagnetic contrast agent, and then digitally stored in the tomograph's console memory, or in a local or remote digital data storage device.

With "effective amount or proper amount", as used herein, we refer to any dose or amount of a contrast agent according to the invention, or of a pharmaceutical composition thereof, that is sufficient to fulfil its intended diagnostic purpose(s): i.e., for example, to acquire a collection of a MRI image during the passage of the contrast agent within the concerned pathologic body area, tissue, region or mass, and obtaining a signal intensity curve from acquired images.

According to a preferred implementation, in the above method the assessment of the macromolecular delivery is performed on a punctual basis.

To this extent, each of the above DCE-MRI derived pharmacokinetic parameter p, for instance including $K^{trans}$, $f_{PV}$, AVEGNH, $IAUC_T$ $IAUCE_T$, AUC, AUCE, LATEAUCRATIO and/or EARLYAUCRATIO, and, preferably, $K^{trans}$, AVEGNH, AUC and AUCE, is determined pixel-wise (or voxel-wise, depending on the bi- or three-dimension of the concerned image or body volume), in each of the pathologic (tumor) region(s) and reference region of each of the collected DCE-MRI images, which sample all the pathologic area or tumor volume.

Figure 10:
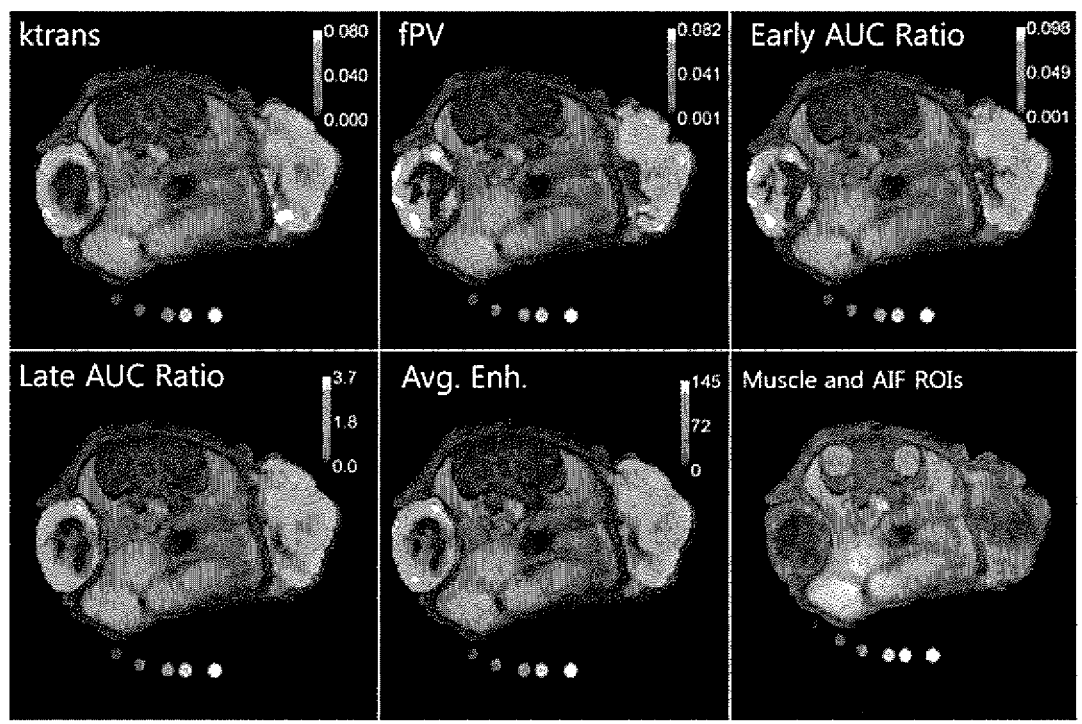
FIG. 10. Comparative parametric images from the in vivo test of Example 5 displaying the pixel-wise DCE-MRI measured values of $K^{trans}$, fPV, EarlyAUC ratio, Late AUC ratio, Average Enhancement (Avg. Enh.) overimposed on the corresponding anatomical MRI image. A panel is also reported, showing Muscle and AIF (Arterial Blood) Regions. In the parametric images, the brightness of the overimposed pixels is used as a measure of the parameter value: the higher is the value of the measured parameter, the brighter is the pixel in the image.

Comparative parametric images from the in vivo test of Example 5 displaying the pixel-wise DCE-MRI measured values of $K^{trans}$, fPV, EARLYAUCRATIO, LATEAUCRATIO, Average Enhancement (AVEGNH), determined with the method of the invention and overimposed to the corresponding anatomical MRI image, are for instance shown in FIG. 10, where a panel is also reported showing the reference (Muscle) and AIF (Arterial Blood) Regions. In the parametric images of the figure, the brightness of the overimposed pixels is used as a measure of the parameter value: the higher is the value of the measured parameter, the brighter is the pixel in the image.

Two sets parametric values are accordingly obtained, on a puntual basis, for each of the assessed parameter: one from the ROI(s) of interest, namely the pathologic region(s), and the other from the reference region.

An assessment of the the macromolecular delivery is then performed by comparing, for each of the assessed parameter, the estimated value measured at each pixel (or voxels) in the pathologic tissue or region of interest with corresponding values obtained into the reference healthy region, and by assessing the fraction of pixels/voxels (within the pathologic region) having statistically significant higher values than those estimated in the non-pathologic (healthy) region.

To this extent, the values of the pharmacokinetic parameter(s) determined within reference (non pathologic) regions are used to define a reference statistical distribution characterized by a mean ($\mu$) and a standard deviation ($\sigma$). For each of the estimated pharmacokinetic parameter a comparison test is then performed between values pixel-wise obtained from the pathologic ROI(s) and the corresponding reference statistical distribution derived from the reference ROI, consenting to identify and count, for each tumor ROI of each recorded DCE-MRI image the fraction of pixels resulting in a parameter value greater than $\mu+3\sigma$ (namely pixels/voxels where $p_i > \mu+3\sigma$) where $p_i$ is the measured value of the concerned pharmacokinetic parameter (in each pixel/voxel of the pathological ROI) and $\mu$ and $\sigma$ are, respectively the mean and standard deviation of the corresponding reference statistical distribution.

In this respect, $p_i$ values meeting the above requirement, that is to say greater than $\mu+3\sigma$, are deemed as "favourable" according to the invention or, in other words, as indicative of a permeability significantly different from that observed in the non-pathologic ROI, and pixels/voxels wherein the above condition is verified are labelled as "Permeable" (P) to a macromolecular solute. On the contrary when the comparison test result in $p_i$ values lower than $\mu+3\sigma$ (or, in other words, the test returns a false statement) the pixel/voxel is labelled as "unfavourable" or as "Non Permeable" (NP), as used herein interchangeably, to a macromolecular solute. The likelihood that a macromolecular solute is suitably delivered to a pathological tissue is then expressed by the following ratio: D=P/(P+NP) calculated from all of the collected DCE-MRI images sampling all the pathological body region or tumor volume. In this respect, optimal D values for an effective macromolecular solute delivery into a pathological tissue are D values preferably higher than 0.5, that, in practical terms, corresponds to a body tissue or region wherein more than 50% of the tissue or region itself, considered on a punctual basis, has a permeability higher than that observed in a non-pathologic, reference, area, charactherized by a negligible vascularization.

Figure 8:
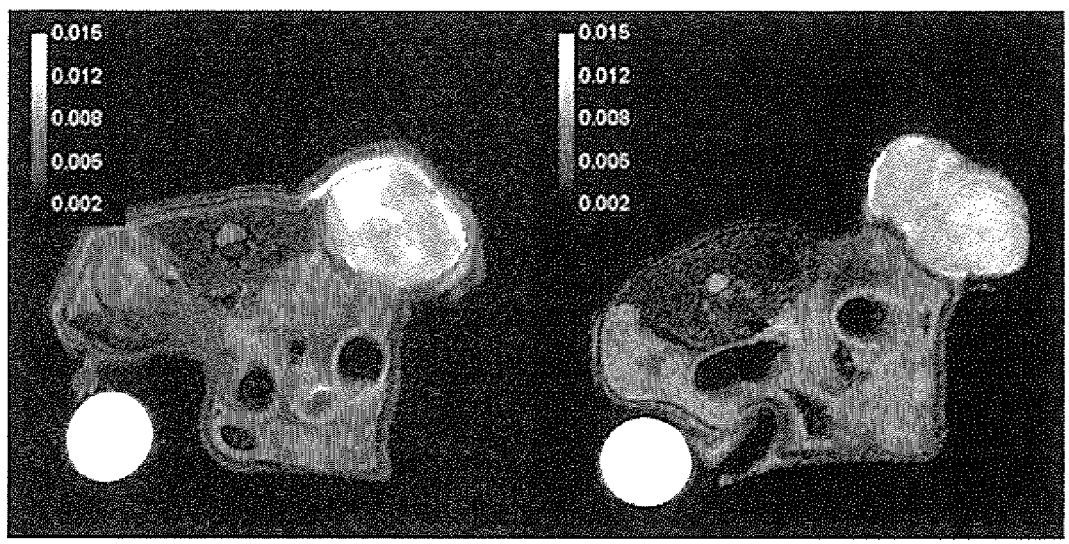
FIG. 8. Comparative parametric images from the in vivo test of Example 4, reporting the pixel-wise DCE-MRI measured $K^{trans}$ values overimposed on anatomical MRI images recorded in a pathological tissue (Xenograft tumor) 24 hours after treatment with PTX (Left image) and with vehicle (Right image). The images show an increased spatial distribution of the albumin in Xenografts tumor treated with PTX.
Figure 11:
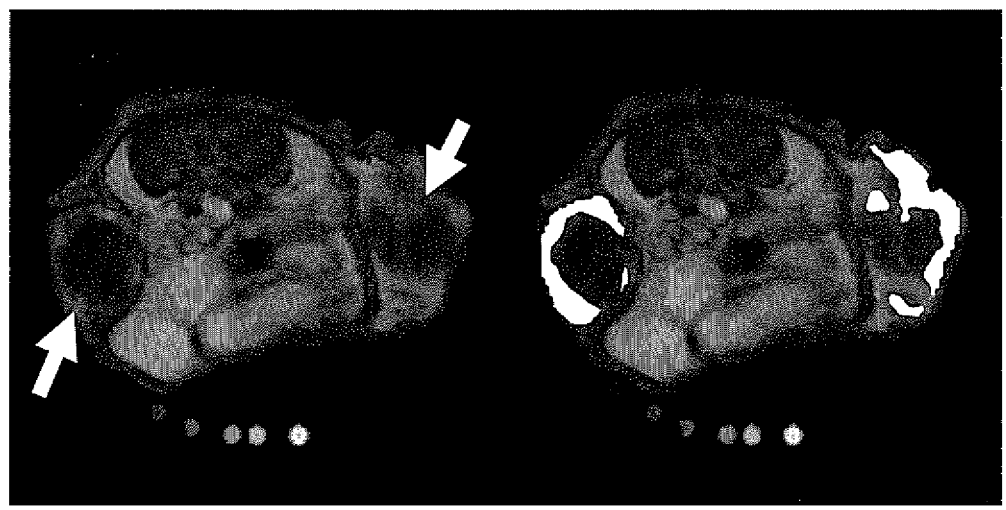
FIG. 11. Comparative images from the in vivo test of Example 5 showing, in the Left Panel, an MRI section of the abdominal region of a mouse (where the arrows indicate the A431 xenografted tumor masses) and in the Right Panel the same section with overimposed the pixels of the tumors with AVGENH>57 (where 57 is the measured threshold value) appearing as the white regions in the image. The figure allows to immediately appreciate both the amount and the distribution of the "Favorable" or "positive" pixels within the tumor region.

To this extent, interestingly, a suitable overimposition of the pixels/voxels labelled as "Permeable" within a pathologic area to the corresponding morphologic MRI image, for instance as in the case of FIGS. 8 and 11, allows to conveniently obtain an instant and surely effective view of the delivery of the macromolecular solute in the pathologic area, consenting to visualize either the extent of the measured delivery and, by a suitable comparison, the increase or decrease of this latter, resulting from a suitable treatment of the concerned pathology with a proper drug improving the macromolecular transport inside the pathological tissue.

It is clear from the foregoing that a preferred implementation of the above method further includes discriminating and selecting pathologies (and patients) resulting in D values equal to or higher that 0.5, and preferably ranging from 0.5 to 0.6, as displaying an adequate penetration to a macromolecular solute and, therefore, reasonably compatible with a treatment whit macromolecular drugs or pro-drugs, from pathologies and patients resulting in a D value lower than 0.5 that could, instead, hardly benefit from a therapy relying on the use of macromolecular drugs or pro-drugs that would not be able to effectively reach the diseased area.

More schematically, the step f is preferably implemented by:
1. Calculating for each of the concerned DCE-MRI parameters p, and preferably including a parameter selected from $K^{trans}$, AVGENH, $f_{PV}$, AUCE, AUC, EARLYAUCRATIO and LATEAUCRATIO, the mean ($\mu$) and standard deviation ($\sigma$) of the values determined, on a pixel basis, in the reference region of each of the DCE-MRI images collected at the step a);
2. Calculating the $\mu+3\sigma$ threshold value for each of the DCE-MRI parameter;
3. Identifying in each of the collected DCE-MRI images those pixels in the pathologic or tumor ROI(s) showing a value of the concerned parameter $p_i > \mu+3\sigma$,
4. Calculating from the tumor ROI(s) of all the DCE-MRI images sampling the whole pathologic area or tumor volume the fraction D of the pixels showing a parameter value exceeding the threshold value ($\mu+3\sigma$),
5. Fixing a cut-off value, for instance 0.5, and defining as "permeable" or "favorable" pathologic body regions or tumors having D≥0.5.

Suitable contrast agents for use in the above DCE-MRI method typically include paramagnetic contrast agents having physiochemical properties similar or close to those of the macromolecular solute of interest.

In this case, in fact, the pharmacokinetic displayed by the contrast agent in a body area under investigation can reasonably be assumed as comparable and, thus, as responsive of the pharmacokinetic behaviour locally exhibited by a macromolecular solute of interest, such as, preferably, a macromolecular drug or pro-drug; accordingly, a measure of those parameters related to the pharmacokinetic these agents display in a concerned body region or tissue can reasonably be considered as equally related to and responsive of the local transport of the macromolecular solute and conveniently be used to obtain reliable estimates of its delivery in the said concerned body area or region. Contrast agents according to the invention typically include macromolecular agents having size and superficial charge analogous or close to those of macromolecular drug or pro-drugs of interest, such as, for instance, the albumin(Gd-DTPA)$_{30}$ (m.w.≅92 KDa), commonly used in the relevant art as prototypical of a macromolecular solute.

On the contrary, commercially available small-molecule contrast media (SMCM) such as, for instance, Magnevist™ or MultiHance™, cannot reasonably be expected to correlate with the transport and delivery of a macromolecular drugs or pro drugs commonly having hydrodynamic radii at least 50-100 times larger than theirs.

Interestingly, we have found that a class of paramagnetic contrast agents exists, herein disclosed, that, despite having a reasonably low molecular weight consenting them to overcome the drawbacks affecting the macromolecular agents of the relevant art, have advantageously proven to follow in vivo, for a suitable time, the pharmacokinetic fate of a macromolecular solute, namely the serum albumin.

Indeed, paramagnetic contrast agents having molecular weight lower than 5,000 Dalton and displaying an in vivo non-covalent binding with HSA of at least 85% (in equilibrium conditions) have interestingly shown to display in human plasma, for a suitable time, that is to say widely compatible with times of the MRI diagnostic imaging, a pharmacokinetic strictly comparable to that of the Serum Albumin, a blood component having a Molecular Weight around 65 KDa.

The use of this class of in vivo albumin binding contrast agents in the DEC-MRI method of the invention formerly disclosed has to be considered as a particularly preferred embodiment of the present invention.

Preferred albumin binding agents according to the invention include paramagnetic contrast agents having molecular weight lower than 5,000 Da, preferably lower that 3,000 Da and, more preferably, comprised from 800 to 3,000 Da, that further display an in-vivo non-covalent protein binding with the Human Serum Albumin (or HSA, or albumin, as herein used interchangeably) equal to or higher that 85%, preferably higher than 90% and, more preferably, higher than 95%, expressed in terms of % of the agent amount that is non-covalently bound to serum albumin, measured by centrifugal ultrafiltration (Centrifree®) from a 0.5 mM solution of the agent in Seronorm® incubated at 37° C., according to the procedure disclosed, for instance, in Invest.Radiol. 2006, 41: 279-291; Whitlam J B, Brown K F. Ultrafiltration in serum protein binding determinations. J.Pharm.Sci. 1981; 70:146-150, and in the Example 2 of the Experimental section.

Among them, particularly preferred are albumin binding agents showing a favourable persistence in the blood system which, in terms of terminal human plasma half-life, (i.e. the time required to divide the plasma concentration by two after reaching pseudo-equilibrium, or half-life of the terminal phase J. vet. Pharmacol. Therap. 2004; 27: 427-439) is of at least 4 hours, and, preferably from 4 to 15 and, more preferably, up to 20 hours from the administration of the agent, while, however, all of the administered agent is suitably excreted within 1 month and, preferably, within 2 weeks from the administration.

This elected class of non-covalent albumin-binding contrast agents have interestingly shown to follow, in vivo, for a sufficient time, the same pharmacokinetics of the human albumin, and provide DCE-MR imaging-derived measures of those parameters related to their transport within a pathologic body area or tissue that, unexpectedly, have proven to linearly correlate with the delivery of this macromolecular solute in the same concerned tissue or area, or, in other words, that have proven to linearly correlate with the amount of the albumin extravasation from the blood vascularisation in the extravascular space of the pathologic tissue and its local spread as histologically observed.

Accordingly, through providing reliable in vivo estimates of the amount of albumin effectively delivered in the concerned tissue or area, the elected class of non-covalent albumin-binding paramagnetic contrast agents identified by the present invention allows to non-invasively obtain reliable DCE-MRI based estimates of the macromolecular transport within a pathologic tissue or mass and, in turn, to discriminate pathologies displaying a penetration-resistance to pharmacological treatments with macromolecular anti-cancer drugs from pathologies that, instead, display an adequate penetration and, thus, compatible with therapeutic treatments making use of macromolecular drugs or pro-drugs. Thus, they can find an advantageous application in protocols or a prognostic procedures aimed to discriminate patients eligible for a treatment with macromolecular drugs from patient probably resistant to such treatment.

The use of this particular class of albumin binding contrast agents in the DCE-MRI method of the invention for non-invasively obtaining in vivo estimates of the delivery of a macromolecular solute of interest into a pathologic body area, region, tissue or solid mass, though it should in no way be considered as limitative or preclusive of the use of any other suitable paramagnetic contrast agent, has to be considered as particularly preferred according to the present invention.

Accordingly, an especially preferred embodiment of the invention relates to a DCE-MRI method which comprises using an in vivo albumin-binding paramagnetic contrast agent according to the invention for non-invasively obtaining in vivo estimates of the delivery of a macromolecular solute of interest into a pathologic body area, region, tissue or solid mass.

Particularly preferred for the above scopes are albumin-binding contrast agents displaying a terminal half life in the human blood circulation of at least 4 hours.

Suitable examples of albumin binding paramagnetic contrast agents according to the present invention includes blood pool contrast agents with a molecular weight lower than 5,000 Da and displaying an in vivo non-covalent binding with HSA of at least 85% (at the equilibrium conditions). Preferably, these contrast agents include in their structure at least one paramagnetic complex unit, which preferably displays one or more than one negative residual charge at the physiological pH, and at least one, but optionally two (or more), lipophilic moiety(ies) promoting the binding of the contrast agent with the HSA. Optionally, they can also include an hydrophilic moiety, for instance an optionally negatively charged group such as a phosphate (for instance a mono- or diester phosphate group), a carboxylate or a sulphonate group, or heteroatom(s) such as oxygen, nitrogen, or sulphur atoms, increasing the number of formed hydrogen-bond and prolonging the blood retention of the contrast agent. The above lipophilic and, optional, hydrophilic moieties and the chelated complex unit(s) of the contrast agent molecule may be linked the each other either directly, through a single bond, or through suitable linkers or linking groups. To this extent, the said hydrophilic moiety (ies) can be conveniently linked to the lipophilic moiety(ies) or, alternatively, to the linking group(s) of which may optionally be an integral part.

The lipophilic moiety(ies) of the contrast agent is preferably represented by a derivative of a bile acid, for instance selected from the group consisting of residues of cholic, chenodeoxycholic, deoxycholic, ursodeoxycholic, lithocholic acids, or is a moiety including one, or two, or even more than two and, for instance, three aromatic or cycloaliphatic ring(s), such as, preferably, a phenyl, a biphenyl, a cyclohexyl, a cyclohexyl-phenyl or a cyclohexyl-biphenyl residue.

Among them, particularly preferred are contrast agents having the following formula (I)

X-L-Y  (I)

where X is a paramagnetic chelated complex of a chelating ligand selected from the group consisting of: diethylenetriaminopentaacetic acid (DTPA), 1,4,7,10-tetraazacyclododecane-1,4,7,10-tetraacetic acid (DOTA), 4-carboxy-5,8,11-tris(carboxymethyl)-1-phenyl-2-oxa-5,8,11-triazatridecan-13-oic acid (BOPTA), or a multidentate AAZTA chelating ligand disclosed in WO03/008390 or in EP 1904460; Y is the residue of biliary acid selected from cholic, chenodeoxycholic, deoxycholic, ursodeoxycholic, lithocholic acids, or is a cyclic or polycyclic residue, which comprises one, two or three aromatic and/or cycloaliphatic rings, an L is a linking group.

Preferred according to the invention are the contrast agents disclosed, for instance, in EP 0806968, and particularly preferred is the trisodium salt of the gadolinium complex identified as Gadofosveset or, alternatively, as MS-325, commercialized as Ablavar™, which has shown to display a non-covalent protein binding with the human serum albumin of about 90% (Invest. Radiol. 2006; 41(3): 229-43). Another preferred group of paramagnetic contrast agent according to the invention includes conjugates of bile acids, for instance disclosed in WO 00/38738 or in US 2007/0059246.

Among them, particularly preferred are chelated complexes of the [3β(S),5β,12α]-3-[[4bis-[bis[2-(carboxymethyl)amino]ethyl]amino]-4-carboxy-1-oxobutyl]amino]-12-hydroxycholan-24-oic acid with paramagnetic metal ions and the physiologically compatible salts thereof. To this extent, suitable paramagnetic metal ions within the scope of the invention are selected from the following: $Fe^{2+}$, $Fe^{3+}$, $Cu^{2+}$, $Ni^{2+}$, $Rh^{2+}$, $Co^{2+}$, $Cr^{3+}$, $Gd^{3+}$, $Eu^{3+}$, $Dy^{3+}$, $Tb^{3+}$, $Pm^{3+}$, $Nd^{3+}$, $Tm^{3+}$, $Ce^{3+}$, $Y^{3+}$, $Ho^{3+}$, $Er^{3+}$, $La^{3+}$, $Yb^{3+}$, $Mn^{3+}$, $Mn^{2+}$. More preferably, the paramagnetic metal ion is $Gd^{3+}$.

Pharmacologically acceptable salts are, for instance, suitably selected from: potassium, sodium, calcium or magnesium salts; ethanolamine, diethanolamine, morpholine, glucamine, N-methylglucamine, and N,N-dimethylglucamine salts; chloride, bromide, iodide, sulfate, acetate, succinate, citrate, fumarate, maleate, oxalate salts; and salts with cations and anions of amino acids such as taurine, glycine, lysine, arginine, ornithine or of aspartic and glutamic acid.

The sodium salt of gadolinium complex with the said [3β(S),5β,12α]-3-[[4bis-[bis[2-(carboxymethyl)amino]ethyl]amino]-4-carboxy-1-oxobutyl]amino]-12-hydroxycholan-24-oic acid chelating ligand, herein alternatively identified as Gadocoletic acid trisodium salt or B22956/1, which has proven to display an in vivo binding with Human Serum Albumin about 95% (see, for instance, de Haen C. et al, Invest Radiol 2006; 41(3):279-91 and the Example 2 below) and a good retention into vascular space (for instance, disclosed in WO 00/38738) is considered as especially preferred contrast agent according to the invention.

Another example of paramagnetic contrast agents of the above formula (I) particularly preferred according to the invention is the Gadolinium complex, disodium salt, of the AAZTA-deoxycholic acid of formula

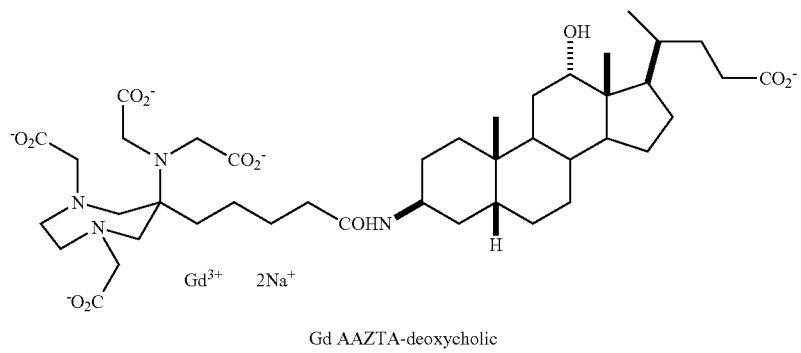

Gd AAZTA-deoxycholic hereinafter called Gd AAZTA-deoxycholic, which has proven to display a binding affinity for the Human Serum Albumin higher than 90%.

Accordingly, an object of the present invention concerns the use of a paramagnetic contrast agent having molecular weight lower than 5,000 Da, preferably comprised from 800 to 5,000 Da and, more preferably, from 800 to 3,000 Da, and displaying an in vivo non-covalent binding with the human serum albumin of at least 85% and, preferably, higher than 85% and corresponding to a non-covalent binding with the HSA of 86, 87, 88, 89, 90, 91, 92, 93, 94 or 95% and, more preferably, higher than 95%, or of a suitable pharmaceutical composition comprising it, for the non invasive in vivo assessment of the macromolecular transport into a pathologic body area, tissue, region or cancerous mass by use of the DCE-MRI technique. Particularly preferred is the use according to the invention of a paramagnetic contrast agent selected from the group consisting of Gadocoletic Acid trisodium salt, Gd AAZTA-deoxycholic disodium salt and Gadofosveset, or of a pharmaceutical composition comprising one of them, alone or in combination with any other drug or pro-drug, suitable additive and/or vehicle.

A further object of the invention relates to a DCE-MRI procedure that comprises using non-covalent binding paramagnetic contrast agent having molecular weight lower than 5,000 Da and displaying in-vivo a non-covalent binding with human serum albumin of at least 85% and, preferably, higher than 90% and, more preferably, higher than 95%, for obtaining in-vivo estimates of the delivery of a macromolecular solute of interest into a pathologic body area, region, tissue or solid mass and, especially, tumors or cancerous masses. To this extent, particularly preferred among them are contrast agents having molecular weight from 800 to 5,000 and, more preferably, from 800 to 3,000 Da, that further display a terminal half life value in the blood circulation in humans of at least 4 hours.

Preferably the said DCE-MRI procedure comprises, as main steps, the process steps previously identified and discussed in detail and, more preferably, makes use of a contrast agent selected from the group consisting of Gadocoletic acid trisodium salt, Gadofosveset trisodium salt and Gd AAZTA-deoxycholic, disodium salt.

From all the foregoing, as the method of the invention allows to obtain an assessment of the delivery of a macromolecular solute of interest that relies on the determination of the albumin delivery performed by the use of DCE-MRI techniques, it can be considered as a prognostic method.

Accordingly, a further object of the invention is a prognostic method which comprises using a paramagnetic contrast agent having molecular weight comprised from 800 to 5,000 Da and displaying a non-covalent binding to the human serum albumin of at least 85% and, preferably, higher than 90% for non-invasively in vivo estimating the delivery of a macromolecular solute of interest into a pathologic body area, region, tissue or solid mass and, especially, of a macromolecular therapeutic agent within a tumor, a cancerous tissue or a chronically inflamed area such as, for instance, an arthritic area or body region by the use of DCE-MRI techniques.

In an additional embodiment, the invention relates to the use of the elected class of albumin-binding contrast agents and the DCE-MRI method of the invention for non-invasively discriminating pathologies and patients where delivery conditions underlying the extravasation and the diffusion of macromolecular solutes are suitably met, from malignancies or patients that, conversely, display a resistance to pharmacological treatments with macromolecular anticancer drugs or pro-drugs due to the inadequate delivery thereof in the pathological tissue to be treated.

The said discrimination can conveniently be operated based on a quantification of the delivery of a macromolecular solute in the pathology affecting patients under screening, for instance by making reference to the D value measured within the concerned pathologic area, wherein, as said, values of D preferably higher than 0.5, for instance from 0.5 to 0.6, can be considered as indicative of an adequate delivery, compatible with a therapeutic treatment making use of macromolecular drugs or pro-drugs, while D values lower than 0.5 are conversely, indicative of a poor or impaired penetration and delivery, that could compromise a treatment with macromolecular drugs.

Accordingly, an additional embodiment of the invention relates to a protocol for the stratification or, in other terms, the classification of oncologic patient which comprises using a paramagnetic contrast agent having molecular weight from 800 to 5,000 Da and displaying an in-vivo non-covalent binding with Human Serum Albumin equal to or higher than 85% and, preferably higher than 90%, for the non-invasive identification of patient resistant to anticancer therapy making use of macromolecular drugs or pro-drugs due to their insufficient or impaired penetration in the pathologic area to be treated.

Preferably, the above protocol is applied for identifying and stratifying patients resistant to an anticancer therapy relying on the use of monoclonal antibody- or peptide- or even polymer-derivative anticancer drugs or pro-drugs, and/ or for optimizing an anticancer therapy relying on their use.

Furthermore, the invention addresses the use of agents and DCE-MRI method of the invention for the selection, the management and the optimization of an anticancer strategy using macromolecular drugs or pro-drugs, alone or combined with other synergic agents including, for instance, any agent or drug devoted to enhance the uptake of the macromolecular drug, such as for instance EPR enhancing agents, as well as for monitoring the effectiveness the said uptake enhancing agent or drug, or of therapies or combined therapies including one of them, as well as for testing the efficacy, in terms of optimal distribution within pathologic tissues of new anticancer drugs or pro-drugs.

Accordingly, the invention further encompasses a protocol using the DCE-MRI method and the agents of the invention for the selection, the management, and the optimization of an anticancer strategy making use of macromolecular anticancer drugs or pro-drugs, alone or combined with an agent devoted to enhance the uptake of a macromolecular solute, and, therefore, of macromolecular drugs or pro-drugs into a pathologic body area, region, tissue or solid mass of interest, or for monitoring the effect provided by the said combined therapy, as well as for monitoring the effect provided by an agent devoted to enhance the uptake of a macromolecular solute.

In this respect, the potential of the elected class of non-covalent albumin binding agents according to the invention to follow the pharmacokinetic fate of a macromolecular compound and, therefore, to provide a reliable assessment of its transport within a pathologic body area of interest has been firstly investigated by Dynamic Contrast Enhanced MRI tests performed in vivo on experimental prostate cancer model in mice.

To this extent, B22956/1 was used as non-limiting representative contrast agent according to the invention and fluorescently tagged Bovine Serum Albumin (BSA, m.w.≅65 KDa) was instead used as prototypical macromolecule able, once injected in mice, to mimic the behaviour of a macromolecular drug having comparable physiochemical properties.

The comparative test has been performed using NCR athymic nude mice implanted with PC-3 cells (a human prostate cancer line) and treated with Axitinib®, a VEGFRs inhibitor, (to modulate the tumor vascular permeability) by a protocol which timing is for instance schematized in FIG. 1. Scope of the test was to compare the image-based analysis of the albumin distribution in a human tumor model as extracted from the analysis of a time-serie of MRI images (with spatial resolution of around 110 µm) acquired with the method of the invention after injection of B22956/1 as contrast agent, and the distribution of FITC-BSA (Fluorescent isothiocyanate Bovine Serum Albumin) albumin inside and outside vessels histologically determined from fluorescent microscopy images on a scale of microns.

Figure 3:
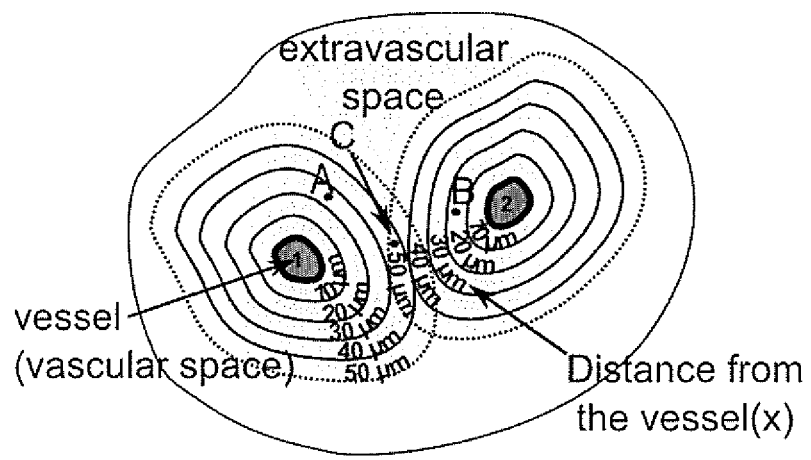
FIG. 3. Graphical schematization of the histological method used in the experimental tests, identifying vessels (1 and 2) in microscopic images and the isodistance line representing the distance from the nearest vessel of every pixel of the microscopic images at which the fluorescence intensity is calculated. For instance, in the scheme, point A is 20-30 μm far from the vessel 1, point B is 10-20 μm far from the vessel 2, point C is 40-50 μm far from the vessel 2 but only 30-40 μm far from the vessel 1 therefore its distance is set to 30-40 μm from the nearest vessel (vessel 1).
Figure 4:
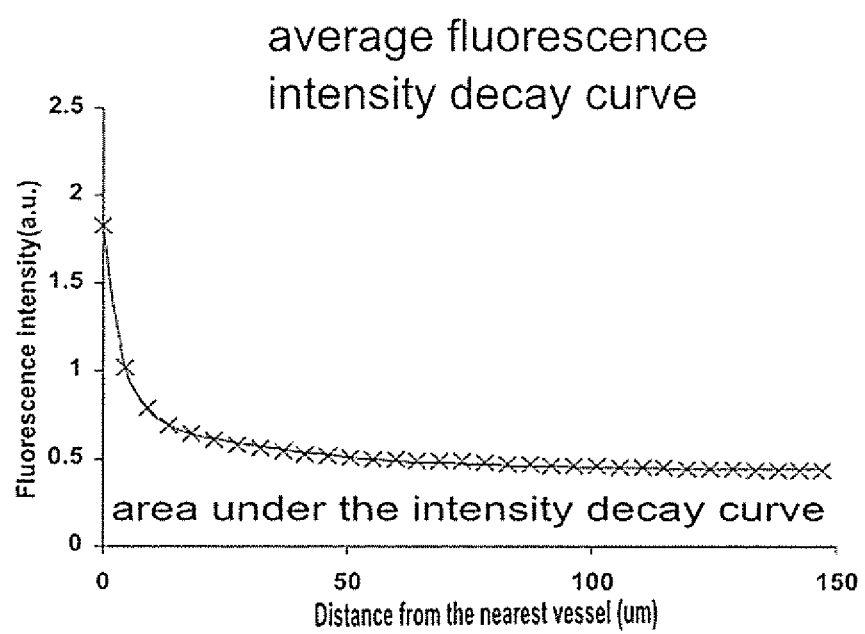
FIG. 4. Fluorescent intensity decay curve obtained from fluorescence intensity values calculated for each pixel at a given distance (x) from the vessel walls. The area under the fluorescence intensity decay curve is calculated numerically integrating the intensity decay curve in an interval of choise, i.e. ranging from the vessels wall and the distance at which the fluorescence approaches the background value.

In particular, the trans-endothelial permeability ($K^{Trans}$) and the fractional plasma volume ($f_{PV}$) were calculated from dynamic MR data by application of a bi-compartmental pharmacokinetic model, while the Initial Area Under the Curve ($IAUC_T$) was calculated in several time windows, typically comprised between the contrast agent administration and the end of the MRI acquisition. The macromolecular penetration in tumors was, then, probed by fluorescently labelled Bovine Serum Albumin administered via tail vein after the last MRI session. Microscopic images were used to quantify the percentage of area stained by fluorescent albumin in the tumor, as a measure of the blood vessel density, using an automatic thresholding method. The albumin extravasation in the tumor extravascular space was assessed based on the fluorescence found out of the blood vessels from histological samples taken from both of tumor rim and core, for instance as schematized in FIG. 2. In particular, the albumin florescence was averaged over all pixels at a given distance from the nearest vessel and stored as a function of distance from the vessels walls, by use of an optimized procedure, for instance schematized in FIG. 3, providing both a quantification of the availability of the albumin in the extravascular space of the concerned tumor, namely the amount of the extravasated FITC-Albumin, and the decay of its concentration over the distance x from a nearest vessel, or, in other words, its actual distribution and dilution within the extracellular spaces (for instance as schematized in FIG. 4).

Notably, statistically significant correlations were observed between microscopic fluorescence and MRI data, for instance observable in tables A and B of provided in the experimental section.

Figure 7:
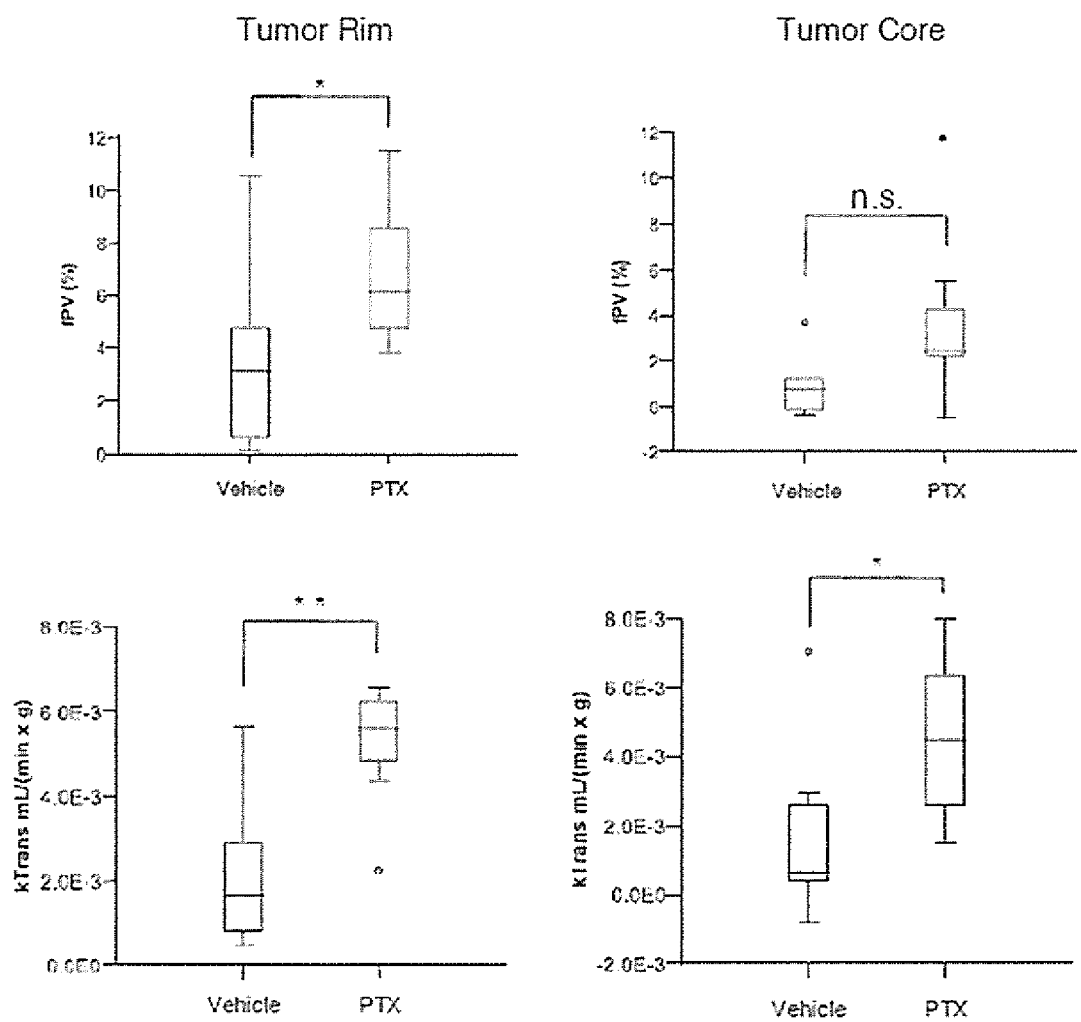
FIG. 7. Graphical presentation (box-plots) of the increase in DCE-MRI values of fractional plasma volume $f_{PV}$ and transfer coefficient $K^{trans}$ measured, in the in vivo Example 4, with B22956/1 in core and rim, respectively, of PTX treated tumors.

In particular, a statistically significant consistency was verified from measured DCE-MRI parameters and the effect promoted by the antiangiogenic treatment, and significant differences between treated and control group animals were observed for both measured $K^{trans}$, $IAUCE_T$ and $IAUC_T$, appreciable in FIG. 7, provided that the MRI Imaging session lasted at least 5 minutes post contrast agent injection, wherein this confirm the capability of the provided method and agents to monitor therapeutic effects of a VEGFRs inhibitor in an hypovascularized tumour.

Most relevantly, moreover, the measures of $K^{trans}$, $IAUCE_T$ and $IAUC_T$, non-invasively determined with the DCE-MRI method of the present invention, summarized in Tables A and B in the experimental section below, showed a statistically significant linear correlation, both in the tumor rim and in the tumor core, with the albumin extravasated from the vessels (FITC-BSA) histologically quantified by the area under the decay curve obtained with the fluorescent microscopy procedure herein proposed. To this extent, the Pearson coefficients obtained for each of the data column, each corresponding to a measured parameter, and the statistical significance are reported in the provided Tables, while a correlation between obtained histological estimates of FITC-BSA against the corresponding values of $K^{trans}$ plotted with regression lines in both tumor core and rim of tested animals is provided in FIGS. 5 and 6.

In particular, the histological analysis of the vessels permeability showed that the treatment with VEGFRs inhibitor induced changes in the albumin concentration not only near the vessels but also at greater distances (100-200 μm). In full agreement with these results, the value of the $k^{trans}$ measured with B22956/1 post treatment with Axitinib™ was lower in the rim of treated tumors, and lower values of the $IAUCE_T/IAUC_T$ parameters over time were also found in treated tumors provided that the MRI acquisition lasted at least 5 minutes post contrast agent injection.

Instead, no significant correlation was observed with MultiHance™, used as reference low-molecular non-albumin binding contrast agent, as it is observable from Tables C and D.

The above prove that the class of non-covalent protein binding agents elected according to the present invention display an in vivo behaviour similar to that of a macromolecular solute, for instance the albumin, and the same or a strictly close pharmacokinetic for a suitable period of time, and can advantageously be used for non-invasively measuring its delivery within a pathologic body area or tissue of interest. Hence, in turn, (by considering the albumin, as said, as putative of a macromolecular drug of interest), they can advantageously be used for non-invasively assessing the delivery of a macromolecular solute of interest in the same concerned tissue or area, as well as, more generally, for stratifying pathologic areas based on their penetrability and possibility of local perfusion by a macromolecular drug of interest.

Besides being surely advantageous, the possibility of using these agents, displaying a moderate-low molecular weight as effective in vivo prototypic of macromolecular solutes is, indeed, unexpected.

In this respect, in fact, it was far from expected that agents having a moderate molecular weight such as B22956/1 (MW 1056.17), MS-325 (MW 975.88), and the Gd AAZTA-deoxycholic, disodium salt (MW 1019.22) a percentage of which, corresponding to the unbound fraction, is quite rapidly excreted from blood circulation, could provide pharmacokinetic parameters that suitably correlate with the delivery of a macromolecular compound having a significantly different size, structure and persistence in the bloodstream such as, for instance, the albumin or, even less, a macromolecular peptide or antibody-derivative drug or pro-drug. This consideration applies especially to these latter, that are known to stay in the vascular compartment for a long time, and then to display a distribution in the extravascular tumor tissues that is strongly dependent on parameters such as diffusivity, antigen density, antigen-binding kinetic, vascular permeability and dose (G. M. Thurber et al. ADV DRUG DELIVER REV 2008, 60: 1421-1434).

Indeed, the potential of non-covalent protein binding contrast agents according the invention to provide in vivo suitable estimates of the effect promoted by a therapeutic agent such as, for instance, an EPR-enhancing agent, i.e. an agent devoted to enhance the uptake of the co-administered macromolecular drug in the tumor area, has been investigated by means of Dynamic Contrast Enhanced MRI tests performed in vivo with B22956/1, used as representative agent according to the invention, on melanoma cancer model xenografts in nude mice treated with vehicle or Paclitaxel (PTX). This compound has in fact shown to be able to enhance the drug delivery in solid tumors by reducing the local Interstitial Fluid Pressure (IFP) caused by the local absence of adequate lymphatic system, thus restoring the convective transport, recognized to be the main driver of the macromolecular transport in tumors, that is, instead, significantly hindered by an excessive interstitial fluid pressure (see, for instance, Paclitaxel Decreases the Interstitial Fluid Pressure and Improves Oxygenation in Breast Cancers in Patients Treated With Neoadjuvant Chemotherapy: Clinical Implications. Simon N. Powell et al. J Clin Oncol 23:1951-1961; Delivering nanomedicine to solid tumors. Jain, R. K. & Stylianopoulos, T. Nat. Rev. Clin. Oncol. 2010, 7: 653-664).

Interestingly, the DCE-MRI assessment of tumor vessels functionality performed with B22956/1 on mice (bearing subcutaneous WM1552/5 melanoma) pre-treated with PTX, showed a significant modification of the pharmacokinetics and the distribution of the contrast agent in both the tumor core and rim of PTX-treated animals over controls.

In particular, a statistically significant increase of the % of the fractional plasma volume $f_{PV}$ (%) and the $K^{trans}$ values was measured in tumors pre-treated with Paclitaxel® over the values measured in tumor administered with vehicle alone, which is fully consistent with an increase of the tumor perfusion and permeability which are known to be promoted by the treatment with PTX. To this extent, a box-plot of DCE-MRI estimates of $f_{PV}$ (%) and $K^{trans}$ obtained in tumor rim and core 24 h after PTX treatment is provided in FIG. 7. Indeed, in full agreement with the alteration of the tumor perfusion promoted by PTX treatment, the plot of FIG. 7 shows that the median values of the pharmacokinetic parameters $f_{PV}$ and $K^{tran}$ were lower for the vehicle group in both core and rim, while an increase was observed in PTX pre-treated animals, in conformity with the alteration of the tumor perfusion (increase of the perfusion) promoted by this EPR enhancing agent.

To this extent, it is worth noting that the values of the pharmacokinetic parameters calculated by the abovementioned DCE-MRI procedure can advantageously be overimposed, by means of a colour-scaled parametric image, on an MRI anatomical reference image of the pathological tissues under investigation, for instance shown in FIG. 8 (as corresponding grayscale), allowing to easily visualize the spatial extension of the increased permeability promoted by the PTX pre-treatment, or, at the same way, the extent and the deep of the delivery of a macromolecular solute of interest. The results of this test from one side support and confirm the significant consistency existing from $K^{trans}$ estimates enabled by the agents of the present invention (within a pathologic tissue) and the effect promoted by an agent devoted to increase the delivery and dilution of macromolecular solutes, suggesting that an estimate of the latter is obtainable by a measure of the former.

The above results suggest that pharmacokinetic parameters displayed by the non-covalently binding agent of the invention, namely $f_{PV}$ and, especially, $K^{trans}$, (as well as, moreover, as formerly discussed, $IAUC_T$ and $IAUCE_T$) that have shown to provide reliable estimates of the albumin delivery, and to be consistent with the effect promoted by an EPR enhancing agent on the macromolecular delivery, may be also related to the delivery and the diffusion of different classes of macromolecular solutes, for instance including macromolecular peptides, fluorescent antibodies, and, more generally, an antibody-derived anticancer agent of interest An additional experimental test was then performed, disclosed in details in the Example 5 of the Experimental section, aimed to investigate and demonstrate the potential of the non-covalent protein binding contrast agents according to the invention to provide reliable estimates of the distribution of an antibody-derived anticancer drug within a pathologic tumor area, as well as to assess the effect promoted by an agent used to modify its accumulation at various distance from vessel walls in tissues. The experimental test was performed by using Cetuximab® on a tumor xenograft model of human hepidermoid carcinoma (A431), implanted in NCR athymic nude mice (two implants, respectively on the left and the right flank of each mouse) treated, for instance, with vehicle, or Paclitaxel (PTX).

Figure 9:
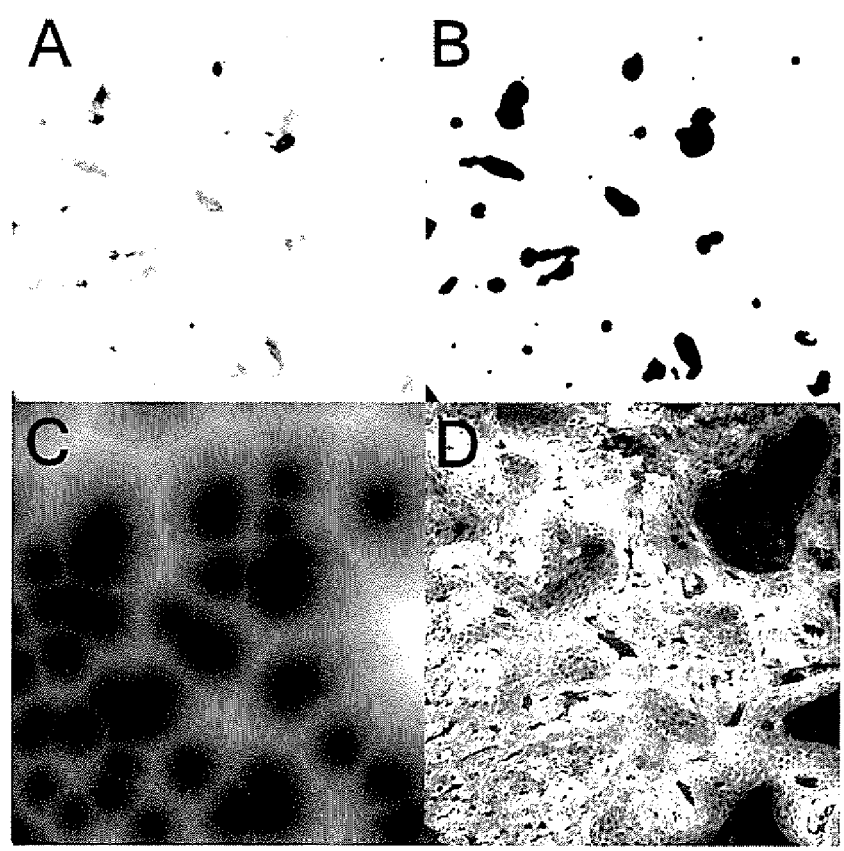
FIG. 9. Histological images from the in vivo test of Example 5. Panel A: FITC-Albumin stained histological image; Panel B: thresholded vessels area; Panel C: map of the distances from nearest vessels; Panel D: Cy5-CTX stained histological image.

To this end, Cetuximab® (CTX) was tagged with the fluorescent cyanine moiety Cy5 enabling its detection and quantization by fluorescent microscopy and used as non-limiting examples of antibody-derived macromolecular drugs while B22956/1 was used as non-limiting example of the Contrast agents according to the invention. The fluorescent microscopy technique was chosen as the reference gold standard for assessing the monoclonal antibody (mAb) delivery due to its sensitivity and ability to resolve the distribution of CTX at the microscopic scale. Histological images exemplifying and detailing the performed test are shown in FIG. 9.

The effect promoted by the treatment with PTX on the kinetics and the distribution of B22956/1 was firstly measured with the method of the invention. In particular, the values of $K^{trans}$, fPV, EARLYAUCRATIO, LATEAUCRATIO and AVGENH were assessed pixel-wise 24 hours after the treatment with PTX and vehicle. Parametric images displaying the values of the above parameters measured pixel-wise from PTX treated mice and overimposed on the corresponding anatomical MRI image are shown in FIG. 10 where a brighter signal stands for a higher parameter value. A panel is also reported in the figure, showing Muscle and AIF (Arterial Blood) Regions (ROIs) used for statistical evaluation of the results. Numerical estimates of the above pharmacokinetic parameters, obtained from PTX-treated and control mice are instead summarized and compared in the Table G of the Example, showing that a statistically significant increase of parameters such as $K^{trans}$, LATEAUCRATIO, $AUC_{20-30}$ and AVGENH was observed in PTX treated tumors which is consistent with the effect on the tissutal diffusivity that is agent is known to promote (see the above cited literature on the PTX effect).

Even more interestingly, the above results are consistent with extravasation and, especially, with the distribution of labelled Cetuximab® (namely Cy5-CTX) in A431 tumor xenograft as histologically determined by fluorescent microscopy.

In this respect, the effect promoted by PTX on the penetration and distribution of the CTX was assessed by fluorescent microscopy, using Cetuximab® suitably labelled with the Cyanine Cy5. Microscopic images were used to quantify the amount of area stained by the labelled mAb and the distance of the stained area from the nearest vessel walls.

In particular, the amount of fluorescently labelled antibody Cy5-CTX accumulates in the tumor 24 hours after PTX and vehicle injection was measured as a function of the distance from the vessels walls by fluorescence histology. Obtained results are graphically presented in FIG. 12. As it clearly appears from the figure, a better and more homogeneous distribution of the administered fluorescently labelled antibody was observed in PTX treated mice over controls showing, instead, a greater CTX accumulation in the perivascular space.

A substantial consistence was, hence, found between the increase of the DCEMRI parameters measured with the non-covalent binding contrast agents and the method of the instant invention and the better distribution of the mAb-derived CTX histologically determined in PTX treated tumor xenograft. On the other side, a substantial coherence was also verified between the teaching provided by the relevant literature on the effect promoted by PTX on the tumor tissutal diffusivity (see for instance F. Marcucci et al., Advanced Drug Delivery Review 2011, 64, 53-68) and modifications in tumor physiology determined with the agents and the method of the invention. In conclusion, obtained results from one side support the feasibility of using the contrast agents and the DCEMRI method proposed by the present invention for assessing the effect promoted by an EPR enhancing agent and the efficacy of an anticancer protocol making use of an anticancer agent in combination with an EPR enhancing drug favouring its delivery within the tumor to be treated. On the other side they further interestingly suggest that, despite the significant difference in the molecular weight and, therefore, in the systematic clearance thereof from the body system, the non-covalent binding contrast agents elected by the present invention can provide numerical DCE-MRI parameters substantially consistent with the transport of a monoclonal antibody-derived anticancer drug and, accordingly, the feasibility of their advantageous use for the non-invasive assessment of penetration-resistant tumors.

To further support this latter hypothesis, DCE-MRI estimates according to the invention were used to discriminate "unfavourable" or "Non-Permeable" tumors (and hence mice) displaying an insufficient or impaired penetration to CTX-labelled drugs from "favourable" or "Permeable" tumors and obtained results were compared with histological estimates.

To this extent, AVGENH was selected as non-limiting example of pharmacokinetic parameters according to the invention because of it robustness and easy determination.

Its value was determined pixel-wise in the tumor ROI drawn in each of the MRI images sampling the whole tumor volume. Pixels with AVGENH>57, where the latter value is the threshold value for the concerned parameter determined from a reference (muscle) region of the recorded MRI images, were identified as "Favourable" or "Permeable". An anatomical image showing overimposed the pixel of the tumor with AVGENH>57 is shown in FIG. 11, consenting to appreciate the amount and distribution of "favourable" pixels within the tumor ROI. The transport of the administered mAb was then assessed in the analyzed tumors as the fraction of total pixels characterized by an AVGENH value over 57. In particular, having fixed 0.5 as the cut-off value, (corresponding to those tumors in which the number of pixels exceeding the threshold are at least equal to the 50% of the total tumor pixels) tumors having a fraction of "Permeable" pixels higher than 0.5 was identified as "favourable" or "Permeable", while "unfavourable" or "Non-Permeable" are defined tumors resulting in lower fraction. Obtained results are schematically presented in FIG. 13, where the fraction of pixels (in each of the tested tumors) exceeding the threshold is compared with the amount of the antibody in the tumor correspondingly determined by fluorescent microscopy (fAUC). As shown in the figure, a statistically significant correlation was found from the fraction of pixels with AVGENH higher than 57 and the measured values of $fAUC_{350,550}$ (sloped line p-value<0.01, Parson Corr. Test) and, hence, with the distribution of the extravasated CTX histologically measured. Indeed, "Favorable" tumors (white dots, were the fraction of pixel with AVGENH>57 exceeds 0.5) showed higher values of $fAUC_{350,500}$ with respect to "Unfavorable" ones (the vertical line is placed to indicate the cutoff value).

These results are consistent with the feasibility of using the proposed contrast agents and method for discriminating "favorable" or "Permeable" tumors from "unfavorable" tumors destined to display a resistance to treatment the antibody derived drug due to its insufficient or impaired penetration in the tumor region to be treated.

For contrast, due to the considerable intensity of the recorded signal both in PTX-treated and Control mice, probably due to a saturation of the detectable area, the use of the in vivo Optical Imaging technique to discriminate vehicle or PTX treated tumors and the assess the effect of this latter on the Cy5-CTX distribution within the tumor region did not allowed any significant result.

From all the above, the class of non-covalently albumin-binding contrast agents identified by the present invention, though having a comparative low molecular weight, can be suggested for use in the assessment of the delivery of an macromolecular solute such as, in particular, an anticancer drugs or pro-drugs within a tumor area, region tissue or mass of interest. Moreover, obtained results further suggest the effectiveness of the albumin-binding contrast agents and DCE-MRI method of the invention for monitoring the effectiveness of an anticancer therapy making use of macromolecular drugs, for instance a monoclonal antibody or antibody-fragment based drug or pro-drug as well as for assessing the efficacy of an anticancer protocol using an anticancer agent in combination with an EPR enhancing drug favouring its delivery within the tumor to be treated.

Figure 13:
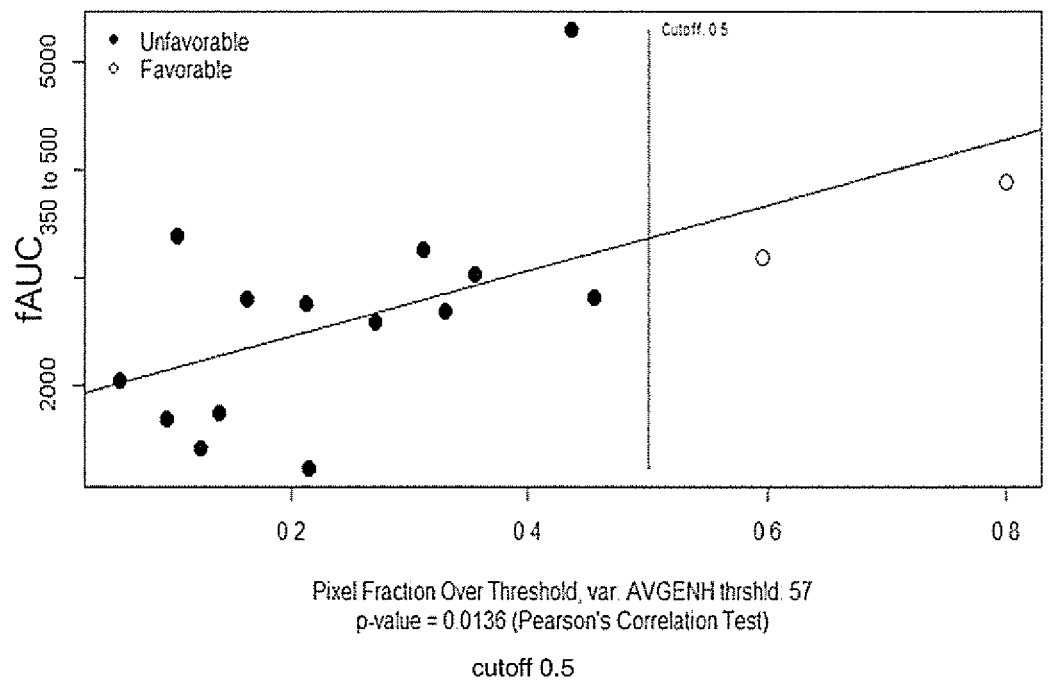
FIG. 13. Graphical presentation of the comparative test of Example 5 correlating DCE-MRI results and histological estimates. The scheme further shows the results of the DCE-MRI based discrimination between "favourable" (or "Permeable") tumors from "unfavourable" (or "Non-Permeable") tumors and the selection criterion used for discriminating. In the figure, the fraction of pixels (calculated from all the pixels of each tumor ROI) with AVGENH>57 showed statistically significant correlation with the values of $fAUC_{350,550}$ (sloped line p-value<0.01, Parson Corr. Test). Indeed, "Favorable" tumors (white dots, were the fraction of pixel with AVGENH>57 exceeds 0.5) showed higher values of fAUC with respect to "Unfavorable" (the vertical line is placed to indicate the cutoff value).

Still moreover, the agents and the DCE-MRI method of the present invention can be suggested for use in the identification and the stratification of penetration-resistant pathologies and, especially, solid tumors, and patients that hardly could benefit from a treatment with a macromolecular anticancer drug or pro-drug, and, especially, an antibody derived drug, for instance represented within the scheme of FIG. 13 by mice on the left of the cut-off line, from patients that are, instead, compatible with a treatment with macromolecular anticancer drugs, due to the existence of those conditions underlying the extravasation and deep diffusion of this latter in the interstitium of the tumor to be treated, for instance represented within the scheme of FIG. 13 by mice on the right side of the cut-off line.

Therefore, an additional object of the present invention includes the use of a paramagnetic contrast agent having molecular weight from 800 to 5,000 Da and displaying an in-vivo non-covalent binding with Human Serum Albumin equal to or higher than 85% and, preferably, higher than 90% for the non-invasive in vivo assessment of the delivery of a monoclonal antibody or antibody-fragment based anticancer drug or pro-drug into a pathologic body area, region, tissue or solid mass of interest by use of the DCE-MRI technique.

Moreover, according to an additional embodiment, the invention further relates to a prognostic, preclinical or clinical or therapeutic protocol that comprises using the contrast agents and the DCE-MRI procedure of the present invention in any of its steps, for instance in a clinical o therapeutic trial, to discriminate "positive" or "responder patients" from "negative" or "non-responders" patient to a therapeutic regimen using a macromolecular drug or pro-drug, or to assess the effect of an anticancer drug or pro-drug or the synergic effect of an adjuvant drug, or any other Target Biological endpoint (TBE) related to the process of macromolecular distribution in tumor tissues.

Non-covalent albumin binding paramagnetic contrast agents according to the invention, as well as their physiologically acceptable salt, are known in the art can, accordingly, be prepared by a skilled person by use of known synthetic procedures. The same applies to their pharmaceutical acceptable compositions.

As a non-limiting example, the preparation of Gadolinium complex of the AAZTA-deoxycholic acid is described in Example 1.

The contrast agents according to the invention can suitably be administered to a patient in need in the form of an injectable pharmaceutical composition including, together with a physiologically tolerable carrier, the paramagnetic contrast agent according to the invention, or a physiologically acceptable salt thereof, preferably formulated at a concentration ranging between 0.001 and 1.0 M, and, more preferably, from 0.01 to 0.5 M, as sterile aqueous solutions with a pH ranging from 6.0 to 8.5. These compositions are for instance formulates as ready for parenteral administration, and, most preferably, for intravenous or intra-arterial administration. Alternatively, these formulations can be lyophilized, to be reconstituted before use.

Generally, and particularly when the administration is intravenous or intra-arterial, pharmaceutical compositions may be supplied as a bolus, or as two or more doses separated in time, or as a constant or non-linear flow infusion.

Further details concerning the DCE-MRI procedure and the practice of the present invention are reported in the following experimental section, with the sole aim to better illustrate the present invention, without representing any limitation to it.

Example 1: Preparation of [[6-[[Bis(carboxymethyl)]amino]-6-[5-[[(3β,5β,12α)-23-carboxy-7-hydroxy-24-cholan-3-yl]amino]5-oxopent-1-yl]-tetrahydro-1H-1,4-diazepine-1,4-(5H)-diacetate(5-)]gadolinate(2-)]disodium (Gd AAZTA-deoxycholic acid disodium salt)

The preparation of the Gd AAZTA-deoxycholic has been performed by using the synthetic process represented in Scheme 1 below.

including as main steps:

a) Preparation of 6-[Bis[2-[(1,1dimethyl)ethoxy]-2-oxoethyl]amino]-6-[5-[[(3β,5β,12α)-23-(methoxycarbonyl)-7-hydroxy-24-cholan-3-yl]amino]5-oxopent-1-yl]-tetrahydro-1H-1,4-diazepine-1,4-(5H)-diacetic acid bis[(1,1-dimethyl)ethyl]ester (3)

(3β,5β,12α)-3-amino-12-hydroxycholan-24-oic acid methyl ester 1 (7.3 g, 18.0 mmol; prepared as disclosed in WO95/32741), 2 (11.0 g, 16.4 mmol prepared as disclosed

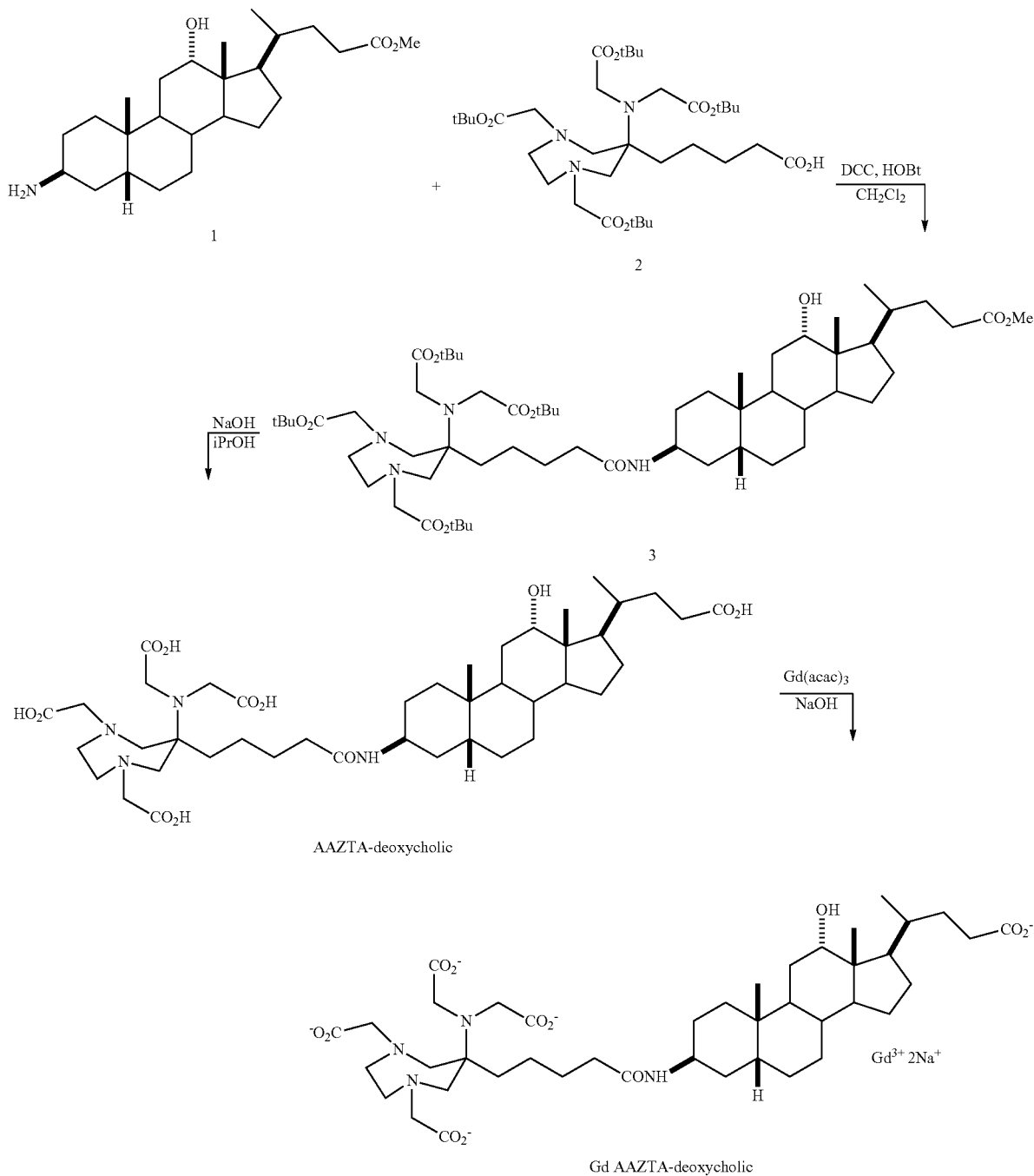

Scheme 1 in WO2008/071679) and N-Hydroxybenzotriazole (HOBt) (2.21 g, 16.4 mmol, Product Aldrich, art. 157260) were dissolved in $CH_2Cl_2$ (105 ml) and cooled to 0-5° C. then a solution of N,N'-dicyclohexylcarbodiimide (DCC) (3.71 g, 18.0 mmol; Product Merck, art. 802954) in $CH_2Cl_2$ (60 ml) was added over 40 minutes. After 2 h at 0-5° C. and 22 h at room temperature, the suspension was filtered, concentrated to half volume and washed with sat. $NaHCO_3$ (3×30 ml) and $H_2O$ (2×30 ml). The organic phase was dried ($Na_2SO_4$), filtered and evaporated. The crude (17.1 g) was purified by flash chromatography (Silica gel 60 (0.040-0.063 mm) (Merck KGaA art. 109385) column h=20 cm, Ø=10 cm; eluent 97: 3 CHCl3/MeOH) to obtain the desired compound 3 (13.36 g; 12.6 mmol) as a solid. Yield 77%

Analytical Data
Mr: 1059.49 ($C_{59}H_{102}N_4O_{12}$)
HPLC: 90.8% (area %)
$^1$H-NMR and $^{13}$C-NMR ($CDCl_3$) are consistent with the expected structure.

b) Preparation of 6-[[Bis(carboxymethyl)]amino]-6-[5-[[(3β,5β,12α)-23-carboxy-7-hydroxy-24-cholan-3-yl]amino]5-oxopent-1-yl]-tetrahydro-1H-1,4-diazepine-1,4-(5H)-diacetic acid (AAZTA-deoxycholic acid)

2M NaOH (74.5 ml, 149 mmol) was added to a solution of compound 3 (12.6 g, 11.9 mmol) in i-PrOH (30 ml) and the solution was stirred at room temperature for 24 h then at 55° C. for 30 h. The pH of the solution was adjusted to 7.7 by addition of 37% HCl and the solution was evaporated to residue then dissolved in $H_2O$ (50 mL). The crude ligand was precipitated at pH 3 by addition of 37% HCl, filtered and washed with $H_2O$ (until pH neutral of the washings). The crude acid thus obtained (8.1 g) was dissolved in $H_2O$ (30 mL) at pH 6.9 by addition of 1N NaOH and purified by chromatography (Amberchrome CG161 resin, eluent: gradient $H_2O/CH_3CN$. The desired product was recovered with 3:2 $H_2O/CH_3CN$). Fractions containing the product were collected and concentrated to remove the CAN, then acidified to pH 3 with HCl 37%. The precipitate was filtered, washed with $H_2O$ (until pH neutral of the washings) dried (30° C. and 15 mbar) to give the desired acid (4.78 g; 5.8 mmol) as white solid. Yield 49%.

Analytical Data
Mr: 821.02 ($C_{42}H_{68}N_4O_{12}$)
HPLC: 89.1% (area %)
$^1$H-NMR and $^{13}$C-NMR: ($D_2O/KOD$): are consistent with the expected structure.
Complexometric Titer: (0.01 M $CuSO_4$): 93.4%
KF: 5.17%.

c) Preparation of [[6-[[Bis(carboxymethyl)]amino]-6-[5-[[(3β,5β,7α)-23-carboxy-7-hydroxy-24-cholan-3-yl]amino]5-oxopent-1-yl]-tetrahydro-1H-1,4-diazepine-1,4-(5H)-diacetate(5-)]gadolinate(2-)] disodium salt (Gd AAZTA-deoxycholic)

AAZTA-deoxycholic acid (2.0 g; 2.31 mmol) was suspended in $H_2O$ (pH 3.8) and dissolved at pH 4.1 by addition of 1N NaOH (2.7 ml; 2.7 mmol); Gd(acac)3 (1.05 g; 2.31 mmol; supplied by Alfa-Aesar art.013204) was added in portion and the complexation was monitored by HPLC-ELSD (see Appendix 1) and with Xilenol Orange assay. The 2,4-pentanedione was extracted with $CH_2Cl_2$ (3×150 ml); the aqueous layer was concentrated, adjusted to pH 6.5 by addition of 0.1 N NaOH (19.2 ml; 1.92 mmol) (total NaOH 4.62 mmol, 2 equivalents) and lyophilized to give the desired complex disodium salt (2.3 g; 2.26 mmol) as white solid. Yield 98%.

Analytical Data
Mr: 1019.21 ($C_{42}H_{63}GdN_4Na_2O_{12}$)
HPLC-ELSD: 99.7% (area %) (see below)
MS: in agreement with proposed structure
Elemental analysis for $C_{42}H_{63}GdN_4 Na_2O_{12}$ (%)

|  | C | H | N | Gd | Na | Cl | $H_2O$ |
|---|---|---|---|---|---|---|---|
| Calcd. | 49.50 | 6.23 | 5.50 | 15.43 | 4.51 | | |
| Found | 45.46 | 6.44 | 5.04 | 13.77 | 4.25 | 0.20 | 7.79 |
| Corresp. to | 49.41 | 6.06 | 5.48 | 14.97 | 4.62 | 0.22 | anhydrous |

Chromatographic Method Phospholipids Rxsil
Stationary Phase: Zorbax RX-SIL, 4.6 mm ID×250 mm (5 μm)
Temperature: 40° C.
Mobile Phase: gradient elution

| A: CH2Cl2/CH3CN/CH3OH/25% NH4OH | 237:237:25:1 (v/v) |
| B: CH2Cl2/CH3CN/CH3OH/H2O/25% NH4OH | 150:150:125:70:5 (v/v) |

Flow rate: 1.2 mL/min

| | Gradient: | |
|---|---|---|
| min | A (%) | B (%) |
| 0 | 100 | 0 |
| 8 | 0 | 100 |
| 16 | 0 | 100 |
| 17 | 100 | 0 |
| 21 | 100 | 0 |

Detection: UV (254 nm)
ELSD (Gain=4; Temperature=42° C.)
Injection: 50 μL
Sample conc.: 2 mg/mL
Instrumentation: VW Elite LaChrom—Hitachi high pressure gradient pump system (L-2100), VWR Elite LaChrom—Hitachi L-2200 autosampler, VWR Elite LaChrom—Hitachi L-2300 column oven, VWR Elite LaChrom—Hitachi L-2400 UV detector, SEDERE SEDEX Model 75 ELSD.

Example 2

Determination of the Binding (as Percent (%) of Binding) of the Paramagnetic Complex with the Human Serum Albumin The binding (%) has been determined by with the method of the centrifugal ultrafiltration as described in: Whitlam J B, Brown K F Ultrafiltration in serum protein binding determination. J. Pharm Sci. 1981; 70:146-150; Bowers W F, Fulton S, thompson J. Ultrafiltration vs equilibrium dialysis for determination of free fraction. Clin Pharmacokinet. 1984; 9:49-60.

Material and Method
B22956/1 (Bracco Imaging S.p.A., prepared for instance as disclosed in WO00/37738)
Gd AAZTA-deoxycholic acid disodium salt (Bracco Imaging S.p.A.) Seronorm® Human (Nycomed Phama)

General Procedure

The albumin serum protein binding was analysed in a human serum solution (Seronorm Human, Nycomed Phama) where each complex was added at a concentration of Gd(III) ion of 0.5 mM. The solutions were incubated in a Amicon ultracentifugation device equipped with an ultrafiltration regenerated cellulose membrane (30 KDa MWCO) kept at 37° C. in a Innova 4230 incubator shaker (New Brunswick Scientific, Edison N.J. USA). Ultrafiltration were carried out after 10 min of sample incubation at 37° C. The percent of Gd(III)-complex bound (% B) was determined by equation: % B=[($C_t$−$C_f$)/$C_t$]*100 where $C_t$ is the total amount of Gd(III) in the incubated solution and $C_f$ is the free Gd(III) complex found in the permeate solution. The average bound fraction was assessed from ultrafiltration experiments carried out in triplicate. The aspecific interaction of each Gd(III)-complex with the ultrafiltration membrane was excluded from recovery experiments performed using an aqueous solution of each complex.

Example A. B22956/1 Percent Bound (% B) to Serum Proteins

A solution of B22956/1 was prepared dissolving 31.8 mg of complex in milliQ water (1 mL), then the amount of Gd(III) was quantified by ICP-MS spectrometer (Elan 6000, Perkin Elmer) after sample digestion in nitric acid in microwave oven (25.07±0.41 mM).

The above solution (0.300 mL) was added to 15 mL of reconstituted human serum. Before ultrafiltration, the solution (0.5 mL) was collected for Inductively Coupled Plasma Mass Spectrometry (ICP-MS) measurement of Gd(III) content ($C_t$) (0.460 mM±0.015). The prepared solution (4.5 mL) was mixed and heated at 37° C. in an incubator shaker and ultrafiltered on a regenerated cellulose membrane (30 KDa MWCO) after 10 min of incubation at 37° C. The protein free permeate solution (0.4 mL) was collected and $C_f$ was measured by ICP-MS analysis. Ultrafiltration procedure was repeated in triplicate.

TABLE a $C_f$ values in the analysed permeated solution.

|  | Average Gd(III) (mM), $C_f$ | S.D. |
|---|---|---|
| Perm. A | 0.016 | 0.001 |
| Perm. B | 0.011 | 0.0004 |
| Perm. C | 0.012 | 0.001 |

From obtained $C_f$ values the percent of bound Gd-complex was determined by application of the following equation $$\% B=[(C_t-C_f)/C_t]*100$$

where $C_t$ is 0.460 mM (S.D.: 0.015).

TABLE b

| % bound B22956/1 | | |
|---|---|---|
| % B | Average | S.D. |
| 96.52 | 97.19 | 0.47 |
| 97.65 | | |
| 97.39 | | |

Example B. Gd AAZTA-Deoxycholic Acid Disodium Salt Percent Bound (% B) to Serum Proteins A solution of the Gd-AAZTA deoxycholic acid sodium salt was prepared dissolving 20.8 mg of complex in milliQ water (0.63 mL). The amount of Gd(III) determined by ICP-MS was 26.06 mM (S.D.: 1.13 mM).

The solution (0.290 mL) was added to 15 mL of reconstituted human serum and 0.5 mL was collected before ultrafiltration to assess the total Gd(III) ($C_t$=0.464 mM, SD: 0.014 mM).

Binding interaction of AAZTA-based Gd complex towards serum proteins was investigated as described in the previous example obtaining:

TABLE c $C_f$ values in the analysed permeated solution.

|  | Average Gd(III) (mM), $C_f$ | S.D. |
|---|---|---|
| Perm. A | 0.038 | 0.001 |
| Perm. B | 0.032 | 0.004 |
| Perm. C | 0.031 | 0.001 |

From which, operating as above said, we obtained

TABLE d

| % bound Gd-AAZTA deoxycholic acid sodium salt | | |
|---|---|---|
| % B | Average | S.D. |
| 91.8 | 92.74 | 0.66 |
| 93.10 | | |
| 93.32 | | |

Example 3: Quantification of the Macromolecular Transport in Tumor by Use of Non-Covalent Protein Binding Contrast Agent and DCE-MRI Imaging Technique Animals The experiment was performed on 20 NCR Athymic nude mice purchased from Harlan Laboratories S.r.l., S. Pietro al Natisone (UD), Italy.

All procedures involving the animals have been conducted according to national and international laws and policies for the Care and Use of Laboratory Animals (L.D. 116/92; Authorization n.19/2008-A issued Mar. 6, 2008, by the Italian Ministry of Health; EEC Council Directive 86/609 CEE, and EEC Council Directive 2010/63/EU).

Tumor Cell Coltures and Preparation of Implants

Human prostate adenocarcinoma cells (PC-3) were supplied by ATCC (American Type Culture Collection) and grown in Hams F-12 medium supplemented with 10% foetal bovine serum, 2 mM glutamine, 100 IU/mL penicillin and 100 µg/mL streptomycin (all from Lonza, Verviers, Belgium). PC-3 cells were then collected and washed two times with PBS; five million cells were resuspended in 0.1 mL Phosphate Saline Buffer (PBS) and injected subcutaneously in the right flank of each 5 week old male mouse. Tumour development was followed by palpation and measured by calliper every 2-3 days until the end of the experiment. The tumour volume was calculated by the formula $(\pi/6) \times (L \times W)^{3/2}$, where L and W are the maximum length and width of the tumour. Mice were distributed randomly into 2 groups (Treated and Control) on the day of initial drug treatment when the average tumour volume will reach 400-600 mm³.

Antiangiogenic Treatment with Axitinib

Axitinib® (from LC Laboratoires, Woburn, Mass., USA) was suspended at 5 mg/mL in polyethylene glycol 400 and sonicated at room temperature for 10 to 20 min to obtain a fine suspension. The pH of the suspension was adjusted to 2-3 using 0.1 N HCl followed by a second sonication. A final 3:7 (v/v) ratio of polyethylene glycol 400:H₂O was be obtained by adding acidified water (pH 2-3). The injection-ready solution was prepared freshly every 4 to 5 days and stored at 4° C. in the dark. Axitinib was daily administered to the tumour-bearing mice by intraperitoneal injection at a dose of 25 mg/kg, corresponding to an administration volume of 5 mL/kg. Control mice received daily intraperitoneal injections of vehicle solution (30% polyethylene glycol 400:70% acidified water, pH 2-3) at the same administration volume used for the test article.

Animals were treated for seven consecutive days.

Experimental Protocol

Contrast Agents and Drug Treatment were administered at the doses and volumes specified in the table 1 below.

At the beginning and at the end of the 6-days treatment period with Axitinib each animal of Control and Treated groups were firstly MRI imaged with MultiHance®, used as reference, non-albumin-binding compound, and 24 hours later with B22956/1.

A schematization of the experiment timing is provided in FIG. 1 in which: the day 0 is the starting day of the treatment with Axitinib, the day 6 is the last day of treatment, the day before the beginning of the treatment with Axitinib®, i.e. the day −1, is the imaging day with MultiHance®, the day 7 is the day of the tumor removal for histology.

TABLE 1

| Group | Treatment/Dose/Volume of administration | Contrast Agent/Dose/Volume of administration |
|---|---|---|
| Control | Axitinib, 25 mg/kg, 5 mL/kg | Multihance ®, 100 µmol/kg, 4 mL/kg<br>B22956/1, 100 µmol/kg, 4 mL/kg |
| Treated | Vehicle solution, 5 mL/kg | Multihance ®, 100 µmol/kg, 4 mL/kg<br>B22956/1, 100 µmol/kg, 4 mL/kg |

DCE-MRI Experiment

During MR imaging experiments, animals were anaesthetized with isofluorane gas (about 1%) in a mixture of 33% O₂ and 66% N₂O. During the experiment, anaesthesia was maintained by adjustment of gas level in function of breath rate.

Contrast Agents were injected intravenously at an injection rate of about 1 mL/min through a catheter placed in the tail vein of the animal.

DCE-MRI Imaging Protocol

The MR experiments were performed on a BioSpec-Bruker spectrometer operating at 3T dedicated to small animal studies, equipped with BGA12S2 gradient coils (12 cm inner diameter).

Coronal and axial Rare T₂-weighted images were acquired with the optimized parameters for high resolution with a good contrast to detect the tumour mass.

Pre-contrast regional longitudinal relaxation times (T1) were measured by acquiring series of 3D FLASH MR images (Fast Low Angle Shot, TR about 6-7 milliseconds) with variable flip angle θ (FA=5-90° before contrast agent injection, by using the following parameters: Matrix 256× 128×8, slice thickness 1.875 mm, FOV 3×3 cm. Two saturation bands were placed just above and below the measured slices to avoid flow artefacts.

T1 values were determined by curve-fitting the equation:

$$S(\theta) = k \frac{(1 - E1)\sin \theta}{(1 - E1\cos \theta)}, \text{ with } E1 = e^{-TR/T_1}$$

where TR is repetition time, T1 longitudinal relaxation time, S(θ) is the signal obtained with a flip angle θ, k is a proportional constant taking into account proton density and receiver gain.

Dynamic 3D FLASH (FA=20°, TR about 6-7 milliseconds, acqu. time≈7.5 s) consisting of 5 initial precontrast and about 315 dynamic postcontrast images were acquired when the contrast agent B22956/1 was injected (scan time 45 min). Five initial precontrast and about 235 dynamic postcontrast images were acquired when the contrast agent MultiHance® was injected (scan time 30 min).

Two saturation bands were placed just above and below the measured slices to avoid flow artefacts.

Histology Protocol

At the end of the last MRI acquisition, fluorescent dye solution (FITC-albumin, 10 mg/mL, Sigma-Aldrich) was injected at the dose of 100 mg/kg (administration volume: 10 mL/kg) into the tail vein. Twenty min after injection, mice were killed by cervical dislocation. The excised tumours were cut in three pieces along the cranial/caudal direction.

Samples were fixed overnight in 4% formalin and then incubated overnight in 30% sucrose saline solution. Finally, the samples were embedded in OCT (optimum cutting temperature) compound. The entire tissue blocks were frozen in isopentane cooled down in liquid nitrogen.

Approximately 1600 5-µm thick cryosections (selected histological sections) were obtained from the OCT blocks. Five contiguous sections (25-µm) were cut every 100-µm from the middle pieces of the tumor masses approximately in planes parallel to those used for the MR images.

For Albumin-FITC visualization, sections were fixed in 2% neutral buffered formalin for 10 min, washed in Phosphate Buffer Saline (PBS) added with 0.1 M Glycine for 20 min, and mounted in Mounting Medium.

Figure 2:
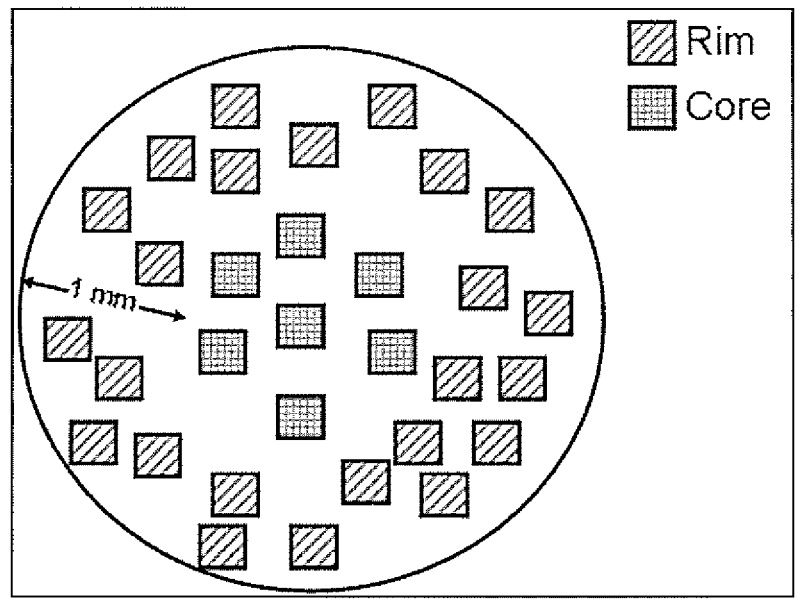
FIG. 2. Microscopic images sampling scheme.

From each animal approximately seventy images at 10× magnification were sampled from the selected histological sections obtained the rim and core regions of the tumor, for instance as schematized in FIG. 2. The rim was defined as the 1-mm peripheral edge of the tumor sections. The core corresponds to the central part of the tumor sections.

Histological images were captured using a Leica fluorescence microscope DM2500 and LAS software at Biology Laboratories.

DCE-MRI Data Analysis

Regions of interest (ROIs) were drawn and signal intensities recorded for the blood, (in the inferior vena cava or abdominal aorta), and for the tumor rim (1-mm peripheral edge of the tumor), tumor core (the central part of the tumor) and the entire tumor region.

Two kind of analysis were then carried out, according to the two different implementations procedures provided of the DCE-MRI method of the invention:

1. model-free analysis of the signal enhancement and contrast agents concentration as function of time in tumour 2. pharmacokinetic (modelled) analysis of the longitudinal relaxation time variance as function of time (three sections), on the basis of a two-compartmental pharmacokinetic model.

The final result of the analysis was a dataset containing both model-free and pharmacokinetic parameters for each MRI slice acquired from the tumors, for instance provided in tables A and B.

Images were analyzed on a Windows computer using the public domain NIH ImageJ program (developed at the U.S. National Institutes of Health and available, for instance, on the Internet at http://rsb.info.nih.gov/nih-image/). Collected images data was elaborated by a Phyton script. Statistical analysis was performed using SPSS (SPSS, Inc., Chicago Ill.).

Contrast Agent Concentration Estimation

Pre-contrast R1 values for tumor regions and blood were determined from the variable-flip angle FLASH images. The method consisted in least square fitting, pixel-wise, the linear form of the measured values of $S(\theta,i,j)$ as function of $\theta$, where $S(\theta,i,j)$ is the signal measured in the pixel (i,j) with flip angle equal to $\theta$.

Postcontrast R1 values for tumor ROIs and blood were calculated ROI-wise, from average precontrast R1 values and average signal intensities of dynamic 3D images obtained before and after contrast administration using the following equations:

$$R_1(ROI, t) = \frac{\ln\left(\frac{1-A}{1-A\cos\theta}\right)}{TR}; A = \frac{S(ROI, t)}{S^{pre}(ROI)} \frac{(1 - e^{-TR*R_1 pre(ROI)})}{(1 - e^{-TR*R_1 pre(ROI)}\cos\theta)}$$

where $R_1(ROI,t)$ is the average $R_1$ calculated at time t for ROI ROI, $S(ROI,t)$ is the average signal intensity calculated at time t for ROI ROI and $S^{pre}(ROI)$ is the average signal measured in ROI ROI from the pre-contrast injection images. Once $R_1$ pre and post contrast has been evaluated, the average CA tissue concentration as function of time was calculated by the well known relation:

$$C_{CA}(ROI, t) = \frac{R_1(ROI, t) - R_{1pre}(ROI)}{r_{1,CA}}$$

where $r_{1,CA}$ is the CA relaxivity and $C_{CA}(ROI,t)$ is the contrast agent concentration measured in ROI ROI at time t.

Model-Free Time Analysis

Initial area under the time-concentration curve ($IAUC_T$) was used to characterize tumor microvasculature. $IAUC_T$ was calculated at various time points using trapezoidal integration of the contrast agent concentration and signal enhancement over the first 1, 5, 10, 15, 20 and 30 minutes post contrast agent injection $$IAUC_T = \frac{1}{2}\sum_{i=2}^{N}(t_i - t_{i-1})(F(i) + F(i-1))$$

where $IAUC_T$ is the IAUC calculated over the first T minutes post-injection, F(i) is the tissue concentration of contrast agent, or the signal enhancement, at dynamic time point i, $t_i$ is the time at time point i, and N is the last time point before $t_i$=T. $t_0$ was defined as the first post-injection timepoint.

In the following $IAUC_T$ indicates the initial area under the contrast agent concentration curve calculated over the first T minutes post injection while $IAUCE_T$ refers to the same calculation but based on the signal enhancement curve.

Pharmacokinetic Model

A two compartment pharmacokinetic model (Daldrup H, et al., 1998 Correlation of Dynamic Contrast Enhanced MR Imaging with Histologic Tumor Grade: Comparison of Macromolecular and Small-Molecular Contrast Media. AJR; 171:941-949; Tofts P. S. et al, 1999, Estimating Kinetic Parameters From Dynamic Contrast-Enhanced T1-Weighted MRI of diffusible Tracer: Standardized Quantities and Symbols. JMRI; 10:223-232, both of them herein incorporated by reference) was used to describe the kinetic behaviour of the contrast medium in tumour tissue, precisely to describe kinetics of exchange between plasma and extravascular extracellular space (EES) in tumour.

The differential equation describing the kinetic behaviour of the CA in the tissue of interest when the vascular term is included is given by:

$$\frac{d[C_{tis}(t) - f_{PV}C_P(t)]}{dt} = K^{trans}C_P(t) - k_{ep}[C_{tis}(t) - f_{PV}C_P(t)] \quad (1)$$

Solving the three parameter the differential equation gives:

$$C_{tis}(t) = K^{trans}\int_0^t C_P(\theta) \cdot e^{-k_{ep}(t-\theta)}d\theta + f_{PV}C_P(t),$$

where $C_{tis}(t)$ and $C_P(t)$ are gadolinium concentration as function of time respectively in tumour tissue and plasma, $K^{trans}$ is the transfer constant, $K_{ep}$ is the rate constant and $f_{PV}$ is the fractional plasma volume.

The values of $K^{trans}$, $K_{ep}$ and $f_{PV}$ can be estimated from DCE-MRI data using the conventional linear least-squares method (see, for instance Kenya Murase, 2004, MRM; 51:858-862, and above cited literature).

To this extent, unless otherwise provided, $K^{trans}$ is herein alternatively referred as kTrans or kTrans mL\(min×g)×100, the latter in case the unit measure is expressed. On the other side $f_{PV}$ is also herein referred as fPV or fPV (%).

Histological Images Analysis

The blood vessel density was quantified as the percentage of area stained by albumin in the tissues of interests using the threshold-based segmentation method describe below, furthermore the fluorescence due to the extravasated fraction of FITC-Albumin was quantified in order to characterize the local microvessels permeability.

Segmentation Method

RGS histogram was stretched to increase the image contrast and then RGB Pixel intensities were converted to 8-bit gray scale applying the luminance formula: Luminance value=0.3 red+0.59 green+0.11 blue Pixels corresponding to vessels (vessel pixels) were segmented by the Otsu threshold algorithm. The segmentation results were validate internally by our histologist.

The blood vessels area was calculated as the percentage of the field of view occupied by vessel pixels (FITC—Albumin Positive Area %).

Extravasation Quantification

In order to analyze the FITC-Albumin distribution in the tumor tissue the FITC-Albumin fluorescence was averaged over all pixels at given distance to the nearest vessel for each image and stored as a function of distance from the nearest vessel (fluorescence decay curve) (Daldrup H, et al., 1998 Correlation of Dynamic Contrast Enhanced MR Imaging with Histologic Tumor Grade: Comparison of Macromolecular and Small-Molecular Contrast Media. AJR; 171:941-949). The total amount of the extravasated FITC-Albumin was quantified by the area under the fluorescence decay curve from 1 to 200 μm (FITC-Alb. Decay AUC(1-200 μm)).

Statistics

In order to assess the correlation existing between DCE-MRI estimates and Histological parameters, the Pearson Correlation was calculated among each of the MRI parameters: kTrans, fPV, IAUCE1, IAUCE5, IAUCE10 and the histological: FITC-Albumin Positive Area %, FITC-Alb. Decay AUC(1-200 μm). A p-value<0.05 was considered statistically significant.

Results

Histological estimates of the albumin distribution derived from fluorescence microscopy images and MRI imaging-based results obtained with Gadocoletic acid trisodium salt in tumor Rim and Core, and Pearson correlation, are summarized in Tables A and B below, respectively, while Table E provides Label definitions for Tables A and B, confirming the substantially linear correlation existing both in core and rim from histological and MRI-derived estimates. Table C and D reports data obtained using the contrast agent MultiHance®, no correlation between DCE-MRI and histological data was found using this contrast agents.

Figure 5:
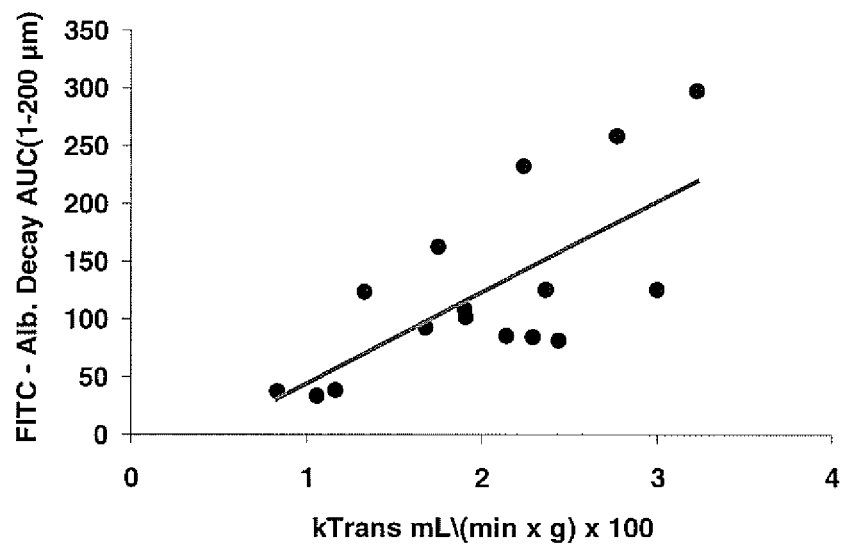
FIG. 5. Correlation of histological estimates of FITC-Albumin decay AUC(1-200 μm) (mean values) calculated, in the in vivo test of Example 3, for each animal in tumor rim and the corresponding values of $k^{trans}$ mL\(min×g)×100 plotted with regression lines.
Figure 6:
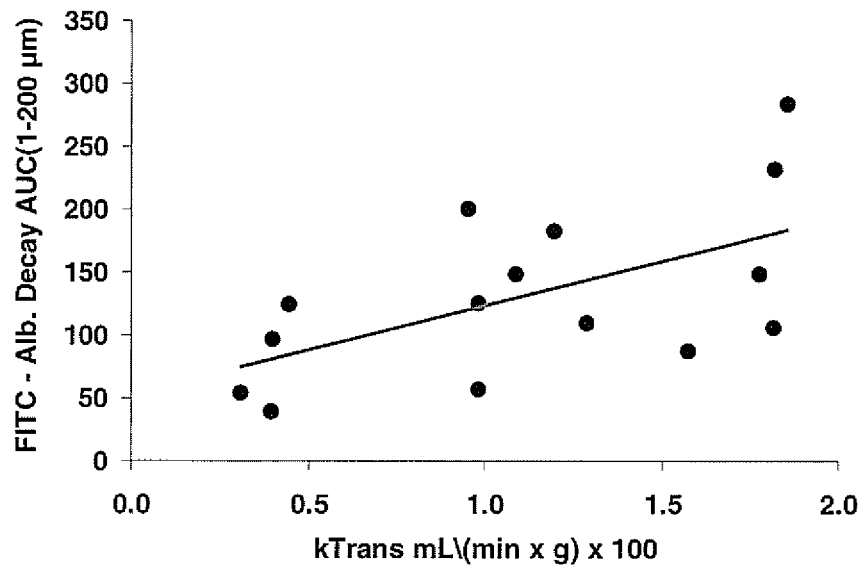
FIG. 6. Correlation of histological estimates of FITC-Albumin decay AUC(1-200 μm) (mean values) calculated, in the in vivo Example 3, for each animal in tumor core and the corresponding values of $K^{trans}$ mL\(min×g)×100 plotted with regression lines.

In particular, the four tables report and compare, for each of the tested animal, the parameter values estimated with the DCE-MRI method of the invention respectively 5, 10, 20 and 30 minutes after the contrast agent administration, both in tumor rim (Table A and C) and core (Table B and D), with the extravasated albumin histologically quantified in the same animal by fluorescent microscopy with FITC-BSA. A graphical representation of the correlation between the amount of extravasted albumin and the MRI-based parameters measured with the use of B22956/1 is shown in FIGS. 5 and 6 where the values of FITC-Alb. Decay AUC(1-200 μm) measured in tumor Rim and Core for each tumor are plotted against kTrans.

The Pearson coefficients obtained for each of the DCE-MRI data column, each corresponding to a measured parameter, are comprised in the provided Tables, confirming the substantial linear correlation existing between DCE-MRI based values obtained with B22956/1 and histological data, that is further confirmed by p-value always lower than 0.05. With the contrast agent MultiHance®, instead no statistically significant correlation was found.

TABLE A

Histological and MRI raw data measured in tumor Rim using the contrast agent B22956/1.
Tumor Rim - CA: B22956/1

| Animal ID | FITC - Alb. Decay AUC(1-200 μm) | kTrans mL\(min × g) × 100 | IAUC5 | IAUC10 | IAUC20 | IAUC30 | IAUCE5 | IAUCE10 | IAUCE20 | IAUCE30 |
|---|---|---|---|---|---|---|---|---|---|---|
| 1 | 296.5 | 3.22 | 6.4 | 16.4 | 37.1 | 55.7 | 16440 | 41031 | 92054 | 138220 |
| 2 | 232.3 | 2.24 | 4.4 | 11.7 | 30.8 | 51.9 | 11902 | 30197 | 76805 | 128047 |
| 3 | 80.7 | 2.45 | 5.8 | 14.8 | 34.8 | 54.5 | 14594 | 36526 | 84965 | 132582 |
| 4 | 100.9 | 1.91 | 4.4 | 11.9 | 28.1 | 45.8 | 11897 | 30837 | 71806 | 116587 |
| 5 | 37.2 | 0.83 | 2.2 | 5.9 | 14.0 | 22.9 | 6071 | 15552 | 36109 | 58691 |
| 6 | 84.3 | 2.30 | 4.4 | 11.1 | 25.6 | 38.7 | 12205 | 30495 | 69645 | 105104 |
| 7 | 33.1 | 1.06 | 2.6 | 7.1 | 16.3 | 26.1 | 6229 | 16434 | 37494 | 59623 |
| 8 | 162.4 | 1.76 | 4.3 | 9.7 | 21.9 | 32.8 | 11751 | 26438 | 58595 | 87383 |
| 9 | 122.5 | 1.33 | 3.1 | 8.0 | 19.0 | 30.3 | 8332 | 20553 | 48892 | 77304 |
| 10 | 125.1 | 3.00 | 5.8 | 16.6 | 39.8 | 62.7 | 13259 | 37782 | 90070 | 141879 |
| 11 | 92.2 | 1.68 | 3.4 | 9.5 | 24.6 | 40.3 | 8145 | 21532 | 54828 | 89231 |
| 12 | 258.2 | 2.77 | 5.3 | 14.4 | 36.6 | 59.7 | 14223 | 36704 | 90712 | 146625 |
| 13 | 84.6 | 2.15 | 4.5 | 11.6 | 27.6 | 43.3 | 9943 | 25402 | 59649 | 93628 |
| 14 | 107.5 | 1.91 | 4.0 | 10.4 | 26.1 | 42.6 | 11984 | 30679 | 75013 | 121740 |
| 15 | 124.6 | 2.37 | 5.5 | 14.0 | 32.8 | 51.3 | 15246 | 37635 | 86682 | 135003 |
| 16 | 38.4 | 1.17 | 2.3 | 5.9 | 13.5 | 20.6 | 6557 | 16442 | 37662 | 57464 |
| Pearson correlation with FITC - Alb. Decay AUC(1-200 μm) | | 0.705* | 0.64* | 0.622* | 0.65* | 0.646* | 0.685* | 0.66* | 0.679* | 0.674* |

Last line: Pearson correlation,
*p-value < 0.05.

TABLE B

Histological and MRI raw data measured in tumor Core using the contrast agent B22956/1.
Tumor Core - CA: B22956/1

| Animal ID | FITC - Alb. Decay AUC(1-200 μm) | kTrans mL\(min × g) × 100 | IAUC5 | IAUC10 | IAUC20 | IAUC30 | IAUCE5 | IAUCE10 | IAUCE20 | IAUCE30 |
|---|---|---|---|---|---|---|---|---|---|---|
| 1 | 282.9 | 1.85 | 3.7 | 9.9 | 22.9 | 34.3 | 10323 | 26853 | 61309 | 91426 |
| 2 | 182.1 | 1.20 | 2.2 | 5.1 | 15.6 | 28.4 | 6223 | 14248 | 41184 | 74290 |
| 3 | 147.7 | 1.09 | 2.2 | 6.4 | 16.2 | 26.7 | 6124 | 16974 | 42163 | 69131 |
| 4 | 124.8 | 0.98 | 2.3 | 6.4 | 15.7 | 27.7 | 6585 | 17450 | 41879 | 73464 |
| 5 | 38.8 | 0.40 | 1.3 | 3.3 | 7.1 | 10.7 | 3462 | 8500 | 17863 | 26524 |
| 6 | 105.3 | 1.81 | 3.1 | 8.1 | 20.4 | 30.7 | 9383 | 24273 | 60004 | 90290 |
| 7 | 54.1 | 0.31 | 1.1 | 3.0 | 6.4 | 10.2 | 2581 | 6731 | 14462 | 22906 |
| 8 | 200.3 | 0.95 | 2.2 | 4.9 | 12.0 | 18.3 | 6235 | 13468 | 32280 | 49184 |

TABLE B-continued

Histological and MRI raw data measured in tumor Core using the contrast agent B22956/1.
Tumor Core - CA: B22956/1

| Animal ID | FITC - Alb. Decay AUC(1-200 μm) | kTrans mL\(min × g) × 100 | IAUC5 | IAUC10 | IAUC20 | IAUC30 | IAUCE5 | IAUCE10 | IAUCE20 | IAUCE30 |
|---|---|---|---|---|---|---|---|---|---|---|
| 9 | 124.2 | 0.44 | 0.7 | 1.9 | 6.2 | 11.6 | 2536 | 5932 | 19228 | 34788 |
| 10 | 148.3 | 1.77 | 2.6 | 8.9 | 22.1 | 35.3 | 5330 | 19696 | 49597 | 79623 |
| 11 | 56.5 | 0.98 | 2.0 | 5.3 | 14.2 | 23.2 | 5108 | 12679 | 32926 | 53148 |
| 12 | 231.7 | 1.82 | 2.9 | 8.4 | 23.0 | 38.5 | 8852 | 24114 | 63086 | 104569 |
| 13 | 87.2 | 1.57 | 2.9 | 7.6 | 18.4 | 29.3 | 6426 | 17186 | 41042 | 65466 |
| 14 | 96.8 | 0.40 | 0.9 | 2.2 | 6.4 | 11.7 | 2628 | 6645 | 18157 | 32664 |
| 15 | 108.9 | 1.29 | 2.6 | 6.9 | 16.8 | 27.0 | 8436 | 21111 | 49854 | 79592 |
| 16 | na | na | na | na | na | na | na | na | na | na |
| Pearson correlation with FITC - Alb. Decay AUC(1-200 μm) | | 0.583* | 0.584* | 0.552* | 0.59* | 0.598* | 0.627* | 0.606* | 0.636* | 0.644* |

Last line: Pearson correlation,
*p-value < 0.05.

TABLE C

Histological and MRI raw data measured in tumor Rim using the contrast agent MultiHance ®.
Tumor Rim - CA: MultiHance

| Animal ID | FITC - Alb. Decay AUC(1-200 μm) | kTrans mL\(min × g) × 100 | IAUC5 | IAUC10 | IAUC20 | IAUC30 | IAUCE5 | IAUCE10 | IAUCE20 | IAUCE30 |
|---|---|---|---|---|---|---|---|---|---|---|
| 1 | 296.5 | 5.23 | 6.1 | 14.2 | 29.4 | 41.9 | 12639 | 28681 | 58877 | 84038 |
| 2 | 232.3 | 2.88 | 3.3 | 9.4 | 23.0 | 37.7 | 5204 | 15189 | 36858 | 60255 |
| 3 | 80.7 | 8.14 | 7.7 | 20.5 | 42.4 | 60.3 | 11096 | 29022 | 59715 | 85214 |
| 4 | 100.9 | 3.59 | 3.8 | 10.0 | 22.7 | 33.9 | 6711 | 17012 | 38283 | 56887 |
| 5 | 37.2 | 3.81 | 4.4 | 12.0 | 28.1 | 44.7 | 8175 | 21865 | 50749 | 80533 |
| 6 | 84.3 | 4.51 | 6.8 | 14.1 | 30.0 | 44.2 | 10794 | 21688 | 46781 | 68598 |
| 7 | 33.1 | 4.22 | 4.7 | 12.4 | 29.1 | 45.0 | 7978 | 20513 | 47719 | 73468 |
| 8 | 162.4 | na | na | na | na | na | na | na | na | na |
| 9 | 122.5 | 4.44 | 5.2 | 12.4 | 27.9 | 41.1 | 7992 | 18894 | 42295 | 62058 |
| 10 | 125.1 | 3.23 | 3.9 | 10.4 | 24.2 | 38.2 | 6081 | 16481 | 37936 | 59998 |
| 11 | 92.2 | 4.78 | 5.9 | 14.6 | 33.7 | 53.3 | 9622 | 23993 | 54443 | 86453 |
| 12 | 258.2 | 6.14 | 6.6 | 18.2 | 45.4 | 70.3 | 12979 | 34097 | 83076 | 128200 |
| 13 | 84.6 | 1.74 | 2.1 | 5.5 | 13.5 | 21.8 | 3835 | 9836 | 23883 | 38489 |
| 14 | 107.5 | 5.23 | 5.9 | 14.5 | 34.1 | 50.6 | 10179 | 25171 | 58481 | 86629 |
| 15 | 124.6 | 5.82 | 7.3 | 18.6 | 42.3 | 65.1 | 11151 | 27846 | 62634 | 96216 |
| 16 | 38.4 | 3.76 | 4.0 | 10.6 | 24.5 | 37.5 | 6842 | 17905 | 41008 | 62781 |
| Pearson correlation with FITC - Alb. Decay AUC(1-200 μm) | | 0.158 | 0.166 | 0.180 | 0.212 | 0.211 | 0.375 | 0.382 | 0.390 | 0.380 |

Last line: Pearson correlation.

TABLE D

Histological and MRI raw data measured in tumor Core using the contrast agent MultiHance ®.
Tumor Core - CA: MultiHance

| Animal ID | FITC - Alb. Decay AUC(1-200 μm) | kTrans mL\(min × g) × 100 | IAUC5 | IAUC10 | IAUC20 | IAUC30 | IAUCE5 | IAUCE10 | IAUCE20 | IAUCE30 |
|---|---|---|---|---|---|---|---|---|---|---|
| 1 | 282.9 | 4.07 | 4.7 | 11.3 | 23.9 | 34.4 | 10312 | 23416 | 49485 | 71322 |
| 2 | 182.1 | 1.06 | 1.4 | 4.1 | 9.5 | 16.3 | 2149 | 6867 | 16006 | 27326 |
| 3 | 147.7 | 3.63 | 2.9 | 9.9 | 23.0 | 36.0 | 4109 | 14214 | 33058 | 52294 |
| 4 | 124.8 | 1.02 | 1.0 | 3.2 | 8.7 | 14.8 | 2175 | 6075 | 16169 | 27673 |
| 5 | 38.8 | 2.86 | 3.5 | 9.6 | 21.5 | 34.4 | 5941 | 15934 | 35774 | 57099 |
| 6 | 105.3 | 3.57 | 5.6 | 10.9 | 23.6 | 34.7 | 8270 | 15542 | 34728 | 50572 |
| 7 | 54.1 | 2.54 | 3.0 | 8.0 | 19.4 | 31.6 | 5070 | 12999 | 31216 | 50704 |
| 8 | 200.3 | na | na | na | na | na | na | na | na | na |
| 9 | 124.2 | 1.53 | 1.5 | 3.6 | 10.1 | 15.9 | 1751 | 4706 | 14092 | 22142 |
| 10 | 148.3 | 0.82 | 1.5 | 4.2 | 9.1 | 15.6 | 1620 | 5271 | 11375 | 19974 |
| 11 | 56.5 | 3.15 | 4.1 | 10.2 | 23.6 | 38.9 | 5893 | 15373 | 35066 | 58692 |
| 12 | 231.7 | 4.46 | 4.5 | 13.1 | 34.1 | 52.5 | 9012 | 24687 | 62493 | 96463 |
| 13 | 87.2 | 1.08 | 1.2 | 3.2 | 8.5 | 13.9 | 2078 | 5488 | 14772 | 24045 |
| 14 | 96.8 | 1.63 | 1.6 | 4.3 | 12.6 | 21.1 | 3164 | 9212 | 25365 | 41734 |

TABLE D-continued

Histological and MRI raw data measured in tumor Core using the contrast agent MultiHance ®.
Tumor Core - CA: MultiHance

| Animal ID | FITC - Alb. Decay AUC(1-200 μm) | kTrans mL\(min × g) × 100 | IAUC5 | IAUC10 | IAUC20 | IAUC30 | IAUCE5 | IAUCE10 | IAUCE20 | IAUCE30 |
|---|---|---|---|---|---|---|---|---|---|---|
| 15 | 108.9 | 3.19 | 4.1 | 10.9 | 25.1 | 39.5 | 7043 | 18191 | 41606 | 65221 |
| 16 | Na | 2.6 | 2.4 | 6.9 | 16.4 | 25.8 | 3438.1 | 10010 | 2389 | 37667 |
| Pearson correlation with FITC - Alb. Decay AUC(1-200 μm) | | 0.296 | 0.167 | 0.218 | 0.219 | 0.159 | 0.358 | 0.380 | 0.369 | 0.317 |

Last line: Pearson correlation.

TABLE E

Labels definitions.

| Label | Definition |
|---|---|
| FITC - Alb. Decay AUC(1-200 μm) | Area under the FITC albumin decay curve from 1 to 200 μm from the nearest vessel. |
| kTrans mL\(min × g) × 100 | Transfer Constant |
| IAUCx | Initial Area Under the Concentration Curve calculated over the first x minutes post injection |
| IAUCEx | Initial Area Under the signal Enhancement Curve calculated over the first x minutes post injection |

Example 4: Use of a Non-Covalent Protein Binding Contrast Agent According to the Invention to Assess the Effect of a Pre-Treatment with Paclitaxel® in Nude Mice Bearing Subcutaneous WM1552/5 Cell Lines Melanoma cell line derived from ATCC WM15 (Silini A, et al. Regulator of G-protein signalling 5 (RGS5) protein: a novel marker of cancer vasculature elicited and sustained by the tumor's proangiogenic microenvironment. Cell Mol Life Sci. 2011 DOI 10.1007/s00018-011-0862-8) derived from patient melanomas were cultured in RPMI 1640 (Roswell Park Memorial Institute 1640) (Gibco, Paisley, UK), supplemented with 10% heat-inactivated fetal calf serum (Sigma, St. Louis, Mo., USA) and 1% L-glutamine (Gibco) and maintained in a humidified atmosphere with 5% CO2 at 37° C. Exponentially growing cells were harvested, repeatedly washed and re-suspended in serum-free medium prior to injection.

Mice and Xenograft Tumor Models

Six- to eight-week-old female NCr-nu/nu mice, obtained from Harlan (Correzzana, Italy) were maintained under specific pathogen-free conditions and handled using aseptic procedures throughout the whole study. Procedures involving animals and their care were conducted in conformity with above mentioned national and international laws and policies on standards for the Care and Use of Laboratory Animals. WM1552/5 cells (2×106 cells) were injected subcutaneously in the right flank of nude mice which were then randomized for treatment (N=10-12 per group) when tumors reached approx 100-150 mg.

Drugs

PTX (Indena S.p.A., Milan, Italy) was dissolved in 50% Cremophor EL (Sigma) and 50% ethanol and further diluted in saline immediately before use. PTX was administered intravenously (i.v.) at a dose of 20 mg/kg.

MRI Imaging

Reagents

B22956/1 (Bracco Imaging S.p.A; obtained as disclosed in WO 00/38738), used as MRI contrast agent.

In Vivo DCE-MRI Imaging

PTX- and vehicle-treated nude mice bearing WM1552/5 melanoma xenografts (N=4 mice per group) were analyzed by DCE-MRI 24 h after PTX administration. To prevent perfusion and permeability from being influenced by the size of lesions, PTX- and vehicle-treated tumors were weight-matched (mean=603 mg and 503 mg, respectively). Magnetic resonance imaging scans were performed using a BioSpec AVIII system (Bruker BioSpin) dedicated to small rodents, equipped with a 7 Tesla/30-cm magnet and a 35-mm birdcage RF coil. Throughout the duration of the scans, animals were kept under controlled anaesthesia (about 30% O2, 70% N2, and 0.8-1% isofluorane). Tumor vascularization was investigated by dynamic contrast enhanced (DCE) series comprising 74 transversal FLASH (Fast Low Angle SHot) 2-dimensional (2D) T1 weighted scans acquired after injection of the B22956/1 as a no limiting example of Contrast Agent according to the invention (Bracco Imaging SpA), 0.1 mmol/kg, with the following parameters: TR/TE 100/3.5 ms, flip angle (FA) 90°, matrix size 128×256, fieldof—view 2.5×2.5 cm2 (corresponding to ca. 200×100 mm$^2$ inplane resolution), 6 slices 2 mm thick, acquisition time 59 seconds/image. One scan with the same parameters was run before CA injection. Pre-contrast T1 values in tumors were measured using a multislice variable flip-angle FLASH. Image 2D reconstruction for all MRI experiments was performed by using the scanner software ParaVision. Image post-processing and data analysis were carried out by in-house developed routines running under Image) (Abramoff, M. D., Magalhaes, P. J., Ram, S. J. "Image Processing with Image)". Biophotonics International, volume 11, issue 7, pp. 36-42, 2004). Obtained estimates are provided as box-plots in FIG. 7, displaying the increase in DCE-MRI-estimated B22956/1 fractional plasma volume fPV and transfer coefficient kTrans in both of core and rim of PTX treated tumors.

Statistical Analysis

Differences in the kinetics of distribution of the contrast agent (DCE-MRI) were analyzed by Mann Whitney U test.

Example 5: Use of a Non-Covalent Protein Binding Contrast Agent According to the Invention to Assess the Transport of an Antibody-Derived Anticancer Drug in Nude Mice Bearing Subcutaneous A431 Vehicle-Treated or Pre-Treated with Paclitaxel Animals The experiment was performed on 8 female NCR athymic nude mice, purchased from Harlan Laboratories S.r.l., S. Pietro al Natisone (UD), Italy. All procedures involving animals and their care were conducted in conformity with institutional guidelines that comply with above referred national and international laws and policies for the care and use of Laboratory Animals.

Tumor Cell Cultures and Tumor Implants

Human epidermoid carcinoma cell line (A431) (supplied by ATCC) were cultured in DMEM (Dulbecco's Modified Eagle Medium) High Glucose medium (4.5 g/L glucose) (Sigma-Aldrich, Steinheim, Germany), supplemented with 10% heat-inactivated foetal bovine serum (Lonza, Verviers, Belgium), 2 mM glutamine (Lonza, Verviers, Belgium), 100 IU/mL penicillin and 100 µg/mL streptomycin (Lonza, Verviers, Belgium) and maintained in a humidified atmosphere with 5% $CO_2$ at 37° C. Exponentially growing cells were harvested and washed two times with PBS. Two million A431 cells were resuspended in 0.1 mL PBS and injected subcutaneously in the right and left flank of each of the 6 week old female mice. Tumors development were followed daily after inoculation, initially by palpation and by caliper once the mass will be established, until the day of the sacrifice. Mice were distributed randomly into 2 groups (Treated and Control) on the day of initial drug treatment when the average tumor diameter reached 7-8 mm, measured by caliper.

Drugs

Paclitaxel (PTX) (Indena S.p.A., Milan, Italy): PTX solution was prepared in 50% Cremophor EL and 50% ethanol as described in Example 4 and further diluted in saline immediately before use to a final concentration of 2 mg/mL. PTX was administered intravenously (i.v., singular administration) at a dose of 20 mg/kg.

Control mice were treated intraperitoneally with vehicle solution (50% Cremophor EL and 50% ethanol diluted in saline), at the same administration volume used for test article.

Experimental Design and Protocol

The experiment was designed to measure the effect induced by PTX on the accumulation and distribution of the antibody Cetuximab® (CTX) in a tumor model of human epidermoid carcinoma (A431) and to compare the obtained results with DCE-MRI data obtained using B22956/1. To this extent, 8 mice were divided into 2 groups; 2 animals of each of the two obtained groups were treated with PTX and 2 with vehicle (CTRL). Treatments started 14 days after the tumor implant, when the tumor reached a diameter in the range 7-8 mm, measured by caliper. The animals were administered with PTX or with CTRL at day 14 from the tumor implant (considered as DAY1). 24 hours after the treatment with PTX or CTRL (DAY2) each animal was injected with B22956/1 (used as non-limiting example of contrast agent according to the invention) and imaged with DCE-MRI. MRI imaging was performed pre-contrast and at different time points post-contrast agents administration. After the MRI experiment, fluorescently labeled Cetuximab® (Cy5-CTX) was injected intraperitoneally. At DAY3 all the mice were imaged in vivo by Optical Imaging (OI); then FITC-Albumin (10 mg/mL) was injected and 5 minutes later the animals were sacrificed. Tumors were excised and a second Optical Imaging acquisition was performed ex vivo. Finally tumors were prepared for the histological examination.

DCE-MRI Experiment

The MR experiments were performed on a BioSpec-Bruker spectrometer operating at 3T dedicated to small animal studies, equipped with BGA12S2 gradient coils (12 cm inner diameter).

Reagents

B22956/1, (Bracco Imaging S.p.A., obtained as above referred) was used as MRI contrast agent (CA). B22956/1 was intravenously injected at the dose of 100 µmol/kg, with an administration volume of 4 mL/kg.

DCE-MRI Imaging Protocol and Sequences 24 hours after the treatment with PTX or CTRL each animal was injected with the CA (B22956/1) and imaged with DCE-MRI. The contrast agent was injected intravenously at an injection rate of about 1 mL/min through a catheter placed in the tail vein of the animal. For MR imaging experiments, animals were pre-anaesthetized with isofluorane gas (about 1%) in a mixture of 33% $O_2$ and 66% $N_2O$ and the anesthesia was then maintained by adjustment of gas level in function of breath rate. MRI imaging was performed at different time points post-contrast agents administration. In particular, pre-contrast coronal and axial Rare $T_2$-weighted anatomical images were acquired with the optimized parameters for high resolution with a good contrast, to detect the tumour mass. 3D FLASH images (Fast Low Angle Shot; TR about 6-7 milliseconds) with variable flip angle θ (FA=5-90° were acquired before contrast agent injection to estimate the tumour and muscle longitudinal relaxation time by using matrix 128×128×8, slice thickness ~1.5 mm, FOV ~3.0×3.0 cm. The same sequences (FA=20°, TR about 6-7 milliseconds) were then acquired to follow CA dynamic in tumor and blood vessels after CA i.v. injection. Flow artifacts were avoided by placing two thick saturation bands just above and below the measured slices.

Optical Imaging Experiment and Protocol

Optical Imaging (OI) experiments were performed on a Pearl Impulse, LiCor, USA. Histology will be performed on ScanScope FL Aperio (USA) at CRB/Z laboratories.

Reagents

ERBITUX (Cetuximab solution; MW ~152 kDa): (Im-Clone LCC, 5 mg/mL (0.033 mM) in a buffer solution consisting of 100 mM sodium chloride, 100 mM glycine, 0.01% Polysorbate 80 and 10 mM citric acid at pH 5.5).

Cyanine Cy5: (Cy5, NHS ester, GE Healthcare, MW 792, 10 mg/mL).

Cy5-CTX: The fluorescently labeled monoclonal Antibody (mAb) was prepared in house, by conjugating the monoclonal antibody (3.51 mg/mL in citrate-TEA buffer, obtained by buffer exchange from the commercial glycine solution of the mAb) with the commercially available fluorescent cyanine Cy5-NHS ester by using typical and well experienced procedures known in the art. Molar ratio dye/mAb in the conjugated product=2.

Albumin-Fluoresceinisothiocyanate: (Albumin-FITC, by Sigma-Aldrich, 10 mg/mL solution).

Optical Imaging Protocol

The labelled antibody was intraperitoneally injected 24 hours after PTX or vehicle administration, at a dose of 1 mg of monoclonal Antibody (mAb) per mouse, corresponding to about 7 nmol of fluorescent dye per mouse.

Animals were pre-anaesthetized with isofluorane gas (2%) in 98% $O_2$ before performing the optical imaging experiment, during the acquisition the anesthesia was maintained by adjustment of gas level in function of breath rate. During the OI session the animals were maintained at 37° C.

24 hours after the injection of Cy5-conjugated Cetuximab mice were analyzed with the above optical imaging system capable of detecting fluorescence intensity. The instrument was equipped with an excitation laser at 650 nm wavelength and a long pass filter with a band pass wavelength of 770 nm. The typical excitation power was 100 µW. The acquisition of the in vivo fluorescence images of the whole thoracic region (1 mm resolution) lasted approximately 10 min. Fluorescence intensity was measured as the number of photon counts in each position of the acquisition region. After the end of the in vivo OI experiments, a fluorescent solution of FITC-albumin (10 mg/mL, Sigma-Aldrich) was injected at the dose of 100 mg/kg (administration volume: 10 mL/kg) into the tail vein. Five minutes after the injection the animals were sacrificed by cervical dislocation an the tumor were excised. The short delay time of 5 minutes between injection and sacrifice was chosen to avoid the overestimation of the vessels dimensions due to the extravasated albumin fraction in the extracellular space. Ex vivo OI experiments on removed tumor were also performed.

Histology Experiment and Protocol

The excised tumors were embedded in OCT (Optimum Cutting Temperature) compound and immediately frozen in isopentane cooled down in liquid nitrogen. 10-μm thick cryosections were then obtained from the OCT blocks. In particular, six sections were cut every 500-μm from each tumor (3 sections per glass slide, two series of glass slides), approximately in planes parallel to those used for the MR images. For Albumin-FITC and the other fluorescent signals visualization, sections were fixed in 10% neutral buffered formalin for 10 min, washed in PBS+0.1 M Glycine for 20 min, and mounted in Mounting Medium with DAPI.

Data Analysis

Histological Images Analysis

In order to analyze the relations among DCE-MRI data, the effect of PTX on the tumor microenvironment and the distribution of CTX in tumors, at the microscopic scale, the fluorescent microscopy was chosen as reference method due to its high sensitivity and high spatial resolution. Indeed, mAbs-based drugs showing high specificity for a membrane antigen as CTX can generate a dramatically inhomogeneous spatial distribution that can inhibit the therapeutic activity of the drug. By fluorescent microscopy it was possible to resolve spatially the distribution of CTX, that is to quantify the amount of the mAb at the microscopic scale, and consequently to investigate the effects of PTX not only on the overall amount of CTX delivered into the tissue but also on the homogeneity if its distribution.

Method

Forty-five histological images were acquired, corresponding to approximately 3 sections per tumor. Each image consisted in a stack of two channels corresponding to the fluorescence signal obtained from the dye Cyanine 5 (Cy5) and Fluorescein isothiocyanate (FITC). Cy5 was conjugated with the mAb Cetuximab® and was used to generate the Cy5-CTX images (FIG. 9 panel D), while the dye FITC, conjugated with albumin, was used to generate the FITC-Alb images (FIG. 9 panel A).

Identification of Perfused Vessels from FITC-Albumin Images.

Perfused vessels inside each section were identified by selecting in each FITC-Alb image all the pixels with a signal intensity over a specified threshold (FIG. 9 panel B). The value of the threshold was selected and validated by visual inspection by an expert histologist.

CTX Signal Decay Curve.

The spatial distribution of the Cy5-CTX staining was analyzed calculating for each pixel its distance from the nearest vessel wall using FITC-Alb images (Distance Map FIG. 9 panel c). In the corresponding Cy5-CTX image, the Cy5-CTX signal was then expressed as a function of the pixel distance from the vessel wall (CTX decay curve). (As far as the adopted protocol see, for instance, F. Tannock et al., 2005. Clin Cancer Res, 11, 8782-8788 and Tong, R. T. et al., 2004 Cancer Res, 64, 3731-3736). Spatial distribution data obtained with this method covered from 0 to about 700 μm from the nearest vessel wall.

DCE-MRI Image Analysis

The entire image analysis was performed using the Image) software, while collected data were elaborated within the R statistical analysis environment (R Development Core Team (2011). R:A language and environment for statistical computing. R Foundation for Statistical Computing, Vienna, Austria. ISBN 3-900051-07-0, URL. http://www.R-project.org/. incorporated by reference).

Contrast Agent Concentration Estimation

Pre-contrast $R_1$ values for tumor, muscle and blood were determined from the variable-flip angle FLASH images. The method consisted in least square fitting the values of $S(\theta)$ as function of $\theta$, where $S(\theta)$ is the signal measured from images acquired with a flip angle equal to $\theta$. Post-contrast $R_1$ values were calculated using pre-contrast $R_1$ values and signal intensities of dynamic 3D images obtained before and after contrast administration using the following equations:

$$R_1(t) = \frac{\ln\left(\frac{1-A}{1-A\cos\theta}\right)}{TR}$$

$$A = \frac{S(t)}{S_{pre}} \frac{(1-e^{-TR*R_1 pre})}{(1-e^{-TR*R_1 pre}\cos\theta)}$$

where $R1(t)$ is the R1 calculated at time t, $S(t)$ is the signal intensity calculated at time t and $S_{pre}$ is the average signal measured in from the pre-contrast injection images. Once R1 pre and post contrast has been evaluated, the average CA tissue concentration as function of time was calculated by the relation:

$$C_{CA}(t) = \frac{R_1(t) - R_{1pre}}{r_{1,CA}}$$

where $r_{1,CA}$ is the CA relaxivity and $C_{CA}(t)$ is the contrast agent concentration measured at time t. One reference $R_{1pre}$ value was calculated roi-wise for tumor, muscle and blood for each animal as the mean 1/T1 value calculated from the variable-flip angle FLASH images of the slices near the centre of the RF coils with the aim of minimizing the error due to RF field inhomogeneity.

Pharmakokinetic Analysis.

A Two-Compartment Pharmacokinetic Model, disclosed, for instance, in the above Example 3 and cited literature, was analogously used to describe the kinetic behaviour of the contrast medium in tumour tissue, and, more precisely, to describe kinetics of exchange between plasma and extravascular extracellular space (EES) in tumour. The same differential equation was exploited describing the kinetic behaviour of the CA in the tissue of interest when the vascular term is included:

$$\frac{d[C_{tis}(t) - f_{PV}C_P(t)]}{dt} = K^{trans}C_P(t) - k_{ep}[C_{tis}(t) - f_{PV}C_P(t)]$$

giving, at the same way, the following equation:

$$C_{tis}(t) = K^{trans} \int_0^t C_P(\theta) \cdot e^{-kep(t-\theta)} d\theta + f_{PV} C_P(t),$$

where $C_{tis}(t)$ and $C_P(t)$ are gadolinium concentration as function of time respectively in tumour tissue and plasma, $K^{trans}$ is the transfer constant, $K^{ep}$ is the rate constant and fPV is the fractional plasma volume. The values of $K^{trans}$, $K^{ep}$ and fPV were then estimated from DCE-MRI data, for instance using the conventional linear least-squares method (see, to this extent, the above cited literature).

The Arterial Input Function (AIF), namely the concentration of the injected contrast agent B22956/1 in plasma expressed as a function of time, was, moreover, computed by analysing the MRI signal in blood roi-wise. The AIF used for the pharmacokinetic analysis was obtained averaging the AIFs measured for each animal (pooled AIF or population-based AIF).

A Pixel-wise analysis was performed over the regions of interest corresponding to the tumors inoculated in the right and left flanks and over the muscle.

Model-Free Analysis.

This approach is advantaged by simplicity, fastness of calculation, especially valuable when applied in pixel-wise analysis over thousands of pixels, and robustness since it is not dependent on a least-squares fitting procedure.

In practical terms, the Area under the time-concentration curve (AUC) was calculated over various time windows numerically integrating the contrast agent concentration or the signal enhancement curve. The value of AUC is defined by the following equation:

$$AUC_{t1,t2} = \frac{1}{2} \sum_{i=t1}^{t2} (t_i - t_{i-1})(F(i) + F(i-1))$$

where AUC is calculated over the $t_1$ to $t_2$ time windows. $F(i)$ is the tissue concentration of contrast agent, or the signal enhancement, measured at time point i. When the AUC is calculated starting from the first time point post-injection the parameter will be referred as the Initial Area Under the Concentration Curve ($IAUC_T$) where T indicates the upper limit of the time window. In this experimental study $AUC_{10,20}$, $AUC_{20,30}$ and $IAUC_1$, were calculated, that is to say, the Area Under the Curve calculated in the time windows from 10 to 20 minutes, from 20 to 30 minutes, and from the first time point to the minute 1 post-injection, respectively. Two additional parameters were then calculated, obtained by combining the values of AUC measured in tumor and in blood. In particular the EARLYAUCRATIO was obtained dividing the $IAUC_1$ in the ROI of interest and reference regions (tumor and muscle) by the $IAUC_1$ measured in blood. To this extent, it is worth nothing that, when the extravasation of the contrast agent within the first minute after injection is negligible, as is the case of B22956/1 (used for the test), then the value of EARLYAUCRATIO is correlated to tumor fractional plasma volume (fPV).

Moreover, since, as said, in this experiment we used a pooled AIF (hence assuming a constant value) the values of EARLYAUCRATIO (as obtained by the above ratio) are directly correlated to $IAUC_1$. The second is the LATEAUCRATIO, which was defined as the Area Under the Enhancement Curve in tumor from 20 to 30 minutes post injection ($AUC_{20,30}$) by the $IAUC_1$ measured in blood. This quantity is related to the amount of extravasated Contrast Agent and thus, indirectly, to the values of ktrans and kep. Moreover, since in this experiment a pooled AIF was used, for the above reason, the values of LATEAUCRATIO are directly correlated to $AUC_{20,30}$. The parameter AVGENH was also calculated, as the average enhancement calculated over all the acquired time points according to the following formula $$AVGENH = \frac{\sum_{i=1}^{N} Enh(i)}{N}$$

where Enh(i) in the signal enhancement at dynamic time point i, and N is the last time point acquired. This parameters was tested because of its very easy calculation and robustness.

In this respect, a correlation Table F is provided herein below, including DCE-MRI parameter values as calculated from experimental DCE-MRI data of this Example test, together with the pairwise Pearson correlation. A correlation factor equal or close to 1 indicates that two parameters express, substantially, the same information. As a special case the parameters EARLYAUCRATIO and LATEAUCRATIO showed Pearson correlation with $IAUC_1$ and $AUC_{20,30}$ respectively equal to 1 because a population based (pooled) AIF was used and as a consequences, it follows from the definition of EARLYAUCRATIO and LATEAUCRATIO, the parameters differ only for a multiplicative factor.

This table substantially confirms that, regardless of the operations performed for their calculation, all these parameters are ultimately related to the same underlying physical phenomenon, namely the pharmacokinetic of the administered contrast agent and, hence, they are in some measure related to each other, and, accordingly, all reasonably exploitable with the method of the instant invention. An exception could be represented by $K_{ep}$ which expresses the rate constant from the EES to the blood and is related to the fraction of extravascular-extracellular space in (tumor) tissue and the wash out of the macromolecular solute rather than its extravasation from the blood to the EES.

TABLE F

|   | ktrans | kep | fPV | EARLYAUCRATIO | LATEAUCRATIO | IAUC1 | AUC20.30 | AUC10.20 | AVGENH |
|---|---|---|---|---|---|---|---|---|---|
| ktrans | 1.00 | 0.52 | 0.53 | 0.71 | 0.70 | 0.71 | 0.70 | 0.79 | 0.74 |
| kep |  | 1.00 | 0.05 | 0.22 | 0.01 | 0.22 | 0.01 | 0.11 | 0.07 |
| fPV |  |  | 1.00 | 0.92 | 0.75 | 0.92 | 0.75 | 0.78 | 0.79 |
| EARLYAUCRATIO |  |  |  | 1.00 | 0.74 | 1* | 0.74 | 0.80 | 0.79 |
| LATEAUCRATIO |  |  |  |  | 1.00 | 0.74 | 1* | 0.98 | 0.98 |
| IAUC1 |  |  |  |  |  | 1.00 | 0.74 | 0.80 | 0.79 |

TABLE F-continued

| | ktrans | kep | fPV | EARLYAUCRATIO | LATEAUCRATIO | IAUC1 | AUC20.30 | AUC10.20 | AVGENH |
|---|---|---|---|---|---|---|---|---|---|
| AUC20.30 | | | | | | | 1.00 | 0.98 | 0.98 |
| AUC10.20 | | | | | | | | 1.00 | 0.98 |
| AVGENH | | | | | | | | | 1.00 |

*Correlation equal to 1 because a pooled AIF was used. It follows from the definition of EARLY and LATEAUCRATIO.

Pixel Over Threshold.

The values of the above DCE-MRI parameters were calculated pixel-wise in the pathologic region of interest, in this example the tumor regions, from DCE-MRI images. Parametric images showing the results of pixel-vise DCE-MRI analysis for each of the assessed parameters overimposed on the corresponding anatomic image are, for instance, shown in FIG. 10.

A threshold value was then calculated pixel-wise for the parameter of interest (p), by considering the mean ($\mu$) and standard deviation ($\sigma$) of the values determined pixel-wise for the concerned parameter in healthy muscle of untreated mice, typically by considering as threshold $\mu+3\sigma$.

For instance, when considering AVGENH as the relevant DCE-MRI parameter p, herein considered as a non-limiting of DCE-MRI parameter according to the invention because of its easy determination and robustness, obtained values were

| Roi | Group | Var | AVGENH |
|---|---|---|---|
| muscle | CTRL | Mean ($\mu$) | 18.49 |
| | | SD ($\sigma$) | 12.94 |
| | | Threshold | 57 | resulting in a threshold value of 57.

The number of pixels is then identified for each ROI, having a parametric value exceeding the assessed threshold value. An overimposition of the pixels of the tumor regions with AVGENH>57 on the corresponding anatomical image, for instance shown in FIG. 11, allows to appreciate both the amount and the distribution of "Permeable" or "favorable" pixels in the ROI. The transport in the tumor tissues of the administered mAb is assessed in the analyzed tumors as the fraction of total pixels (of the tumor ROIs of all recorded MRI images, sampling all the tumor volume) characterized by a value of the measured DCE-MRI parameter (in the example AVGENH) which is statistically different from the corresponding values calculated in the reference tissue, i.e. having an AVGENH over 57. Then by fixing 0.5 as the cut-off value, (corresponding to those tumors in which the number of pixels exceeding the threshold are at least equal to the 50% of the total tumor pixels) tumors having a ratio of pixels with AVGENH over 57 over the total tumor pixels higher than 0.5 were identified as "favorable" or "Permeable", while "unfavorable" or "Non Permeable" are defined tumors resulting in lower ratio.

Optical Images Analysis

Fluorescence images of the whole thoracic region were acquired with 1 mm resolution in PTX treated and Control mice for approximately 10 min.

An highly intense signal area was recorded in both treated and control animals.

Results and Conclusions

Analysis of the PTX Effect on the DCE-MRI Parameters

Statistical analysis was performed on DCE-MRI data to compare treated and untreated tumors 24 h after the treatment with PTX. For each tumor the average value of the DCE-MRI parameters calculated pixel-wise was computed, and then the distributions of the averages of two treatment groups were compared. Statistical significance of the differences was tested with the Mann Whitney U Test. The differences were considered statistically significant with p-values lower than 0.05 (5%).

Obtained results are summarized in Table G reporting mean, standard deviation and number of CTRL and PTX tumors used to obtain the DCE-MRI parameters. The results of the Mann-Whitney U Test are also reported.

TABLE G

| Group | | ktrans | kep | fPV | EARLYAUCRATIO | LATEAUCRATIO | $IAUC_1$ | $AUC_{20.30}$ | $AUC_{10.20}$ | AVGENH |
|---|---|---|---|---|---|---|---|---|---|---|
| CTRL | Mean | 0.0152 | 0.117 | 0.0264 | 0.0247 | 0.71 | 0.55 | 15.7 | 16.9 | 36.2 |
| | SD | 0.0049 | 0.025 | 0.0072 | 0.0087 | 0.12 | 0.19 | 2.6 | 3.4 | 7.6 |
| | N | 8 | 8 | 8 | 8 | 8 | 8 | 8 | 8 | 8 |
| PTX | Mean | 0.0255* | 0.112 | 0.038 | 0.036 | 1.14** | 0.8 | 25.3** | 27* | 54* |
| | SD | 0.0087 | 0.025 | 0.017 | 0.017 | 0.33 | 0.38 | 7.5 | 8.8 | 16 |
| | N | 8 | 8 | 8 | 8 | 8 | 8 | 8 | 8 | 8 |

*p-value < 0.05,
**p-value < 0.01, Mann-Whitney U Test

Obtained data are consistent with an increased blood perfusion and enhanced extravasation of the contrast agent B22956/1 in PTX treated mice over controls. In particular, the PTX treatment has proven to induce an effect that is particularly significant from a statistical point of view, on those DCE-MRI parameters such as trans, $AUC_{20-30}$, LATEAUCRATIO that are related to CA extravasation.

PTX is known to exert a promoting activity when administered in combination with mAbs (F. Marcucci and A. Corti, Advanced Drug Delivery Reviews 2011, 64: 53-68) probably due to its capability in reducing the interstitial fluid pressure and, by consequence, to enhance the convection-mediated transport of macromolecules in tumors (A. Brønstad, A. Berg, and R. K. Reed. Am J Physiol Heart Circ Physiol 2004, 287: H963-H968). The exploitability of the proposed DCE-MRI method to assess the effect of a drug capable of altering the macromolecular distribution in tumors as PTX was tested. The obtained results from one side confirm that modifications induced by PTX in the tumor physiology are measurable with the proposed DCE-MRI method. On the other side, the obtained results further support and suggest that the agents and the DCE-MRI method of the invention can profitably be used for assessing the efficacy of an anticancer protocol making use of an anticancer agent in combination with an EPR enhancing drug, favoring its delivery within the tumor to be treated.

Analysis of the PTX Effect by Optical Imaging

In the performed test, the considerable intensity of the recorded signal both in PTX-treated and Control mice, probably due to a saturation of the detectable area, did not allow to estimate the effect of the PTX on the administered mAb. Indeed, it is known that at high doses, such as 1 mg/mouse, the mAb Cetuximab® can saturate the first 100 µm of tumor tissue from the vessels walls in A431 tumor xenograft although there remained minimal drug penetration in hypoxic regions located in the central part of the tumors (Lee and Tannock BMC Cancer 2010, 10:255). OI confirmed that the mAb accumulated both in PTX-treated and untreated tumors. Due to the limitation of the technique in observing the fluorescence signal coming from below the well perfused superficial part of the tumors, the remarkable effect of the PTX treatment in the central under-perfused area of the tumors was not observed.

Analysis of the PTX Effects on CTX Distribution

Fluorescent CTX decay curves were measured for each tumor section acquired by fluorescence microscopy over distances ranging from 0 to about 700 µm from the nearest vessel wall. Forty-five fluorescence decay curves, divided almost equally between treated and untreated tumors, were analyzed. The distance range between 0 and 700 µm was divided into bins about 20 µm wide and for each interval the value of Area Under the Curve of the fluorescence signal (fAUC) was computed. The distributions of the values of fAUC were compared by the Mann-Whitney U Test to evaluate if the differences between treated and untreated tumors were significant. Obtained results are graphically reported in FIG. 12, where the medians of the fAUC for the PTX and CTRL group calculated in each distance bin are reported with the corresponding p values obtained from the Mann-Whitney U Test.

As clearly appear from the figure, untreated tumors showed greater CTX accumulation between 0 and about 200 µm from the nearest vessel wall. Treated tumors showed higher fluorescence between 400 and about 700 µm from the nearest vessel wall. No differences were found between treated and untreated tumors analyzing the distributions of fAUC values calculated over the whole tested range from 0 to 700 µm. However, a more homogeneous and improved distribution of the administered fluorescently labelled antibody in PTX treated over Control mice is indisputably derivable from the obtained results, for instance observable in FIG. 12.

These results strengthen some findings about the effect promoted on the overall distribution of a mAb in a tumor region by PTX, that, especially when the mAb is administered at high saturating dose, can increase the mAb's distribution volume inside the tumor and cause limited effects on the total amount of mAb accumulated in the tissue (F. Marcucci and A. Corti, Advanced Drug Delivery Reviews 2011, 64 53-68; Lee and Tannock BMC Cancer 2010, 10:255; A. Brønstad, A. Berg, and R. K. Reed. Am J Physiol Heart Circ Physiol 2004, 287: H963-H968; G. M. Thurber et al. Advanced Drug Delivery Reviews 2008, 60: 1421-1434). This is an important pre-requisite to improve the therapeutic effects of macromolecular drugs.

Figure 12:
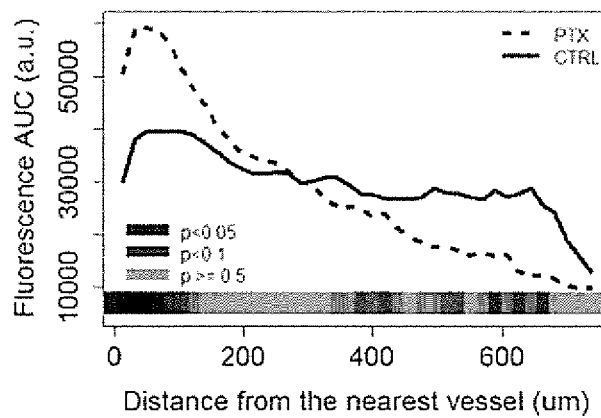
FIG. 12. Average fluorescence decay curve computed in the in vivo test of Example 5, by using Cy5-CTX in nude mice NCR bearing subcutaneous A431 human hepidermoid carcinoma xenografts pre-treated with PTX or vehicle. Statistical significance of the differences between the two curves divided in ranges of about 20 µm is shown in the line below the plot.

Of note, moreover, the behavior of FIG. 12 obtained by histological estimates of the mAB distribution in the tumor area, supporting a better and more homogeneous distribution of the mAb promoted by the treatment with PTX, is consistent with the increase of pharmacokinetic parameters such as, especially Ktrans, fPV, $AUC_{20-30}$ and LATEAUCRATIO measured in PTX treated tumors with the DCE-MRI method of the invention.

Correlation Between DCE-MRI and Histological Data and Tumor Discrimination

The existence of a relation between DCE-MRI parameters obtained with the method of the invention and histological data was analysed. The reference observations were the histological results that showed for PTX-treated and untreated tumors a differential CTX accumulation depending on the distance from the vessels at which the fluorescence was measured. A particular instance of the method of invention was applied on the available data in order to demonstrate the feasibility of the DCE-MRI method of the invention to discriminate the tumors characterized by a favorable extravasation of the antibody CTX from those, instead, showing a limited mAb extravasation. To this extent, the extravasation of CTX was quantified as the fAUC calculated from 350 to 550 µm ($fAUC_{350-550}$).

The applied procedure essentially included the following steps:

1. Analyze pixel-wise the MRI signal intensity time profile in order to calculate the contrast agent concentration time profile and/or the signal enhancement time profile in the ROI (in the following example the subcutaneously implanted tumor).
2. Calculate pixel-wise the values of the DCE-MRI parameters of interest. In the following example the parameter AVGENH was used as representative, non-limiting, DCE-MRI parameter according to the invention for the reason above explained.
3. Calculate the mean ($\mu_{AVGENH}$) and standard deviation ($\sigma_{AVGENH}$) of the values of AVGENH in the reference region (in the following example the dorsal muscle).
4. Identify the fraction of the pixels ($D_{AVGENH}$) in the ROI (tumor) showing AVGENH>($\mu_{AVGENH}+3\sigma_{AVGENH}$).
5. Assign to the "Favorable" group each tumor showing $D_{AVGENH}$>0.5 otherwise assign it to the "Unfavorable" group.

In practical terms, a reference threshold value of 57 was defined from muscle, as formerly described, for the DCE-MRI parameter AVGENH. Pixels with AVGENH>57 were hence identified as the pixels of the tumor ROIs with a favorable physiology for CTX extravasation. In other terms $D_{AVGENH}$ represent the fraction of the "favorable" pixels belonging to the tumor volume measured by analyzing all the available MRI slices displaying at least part of the tumor ROI. $D_{AVGENH}$ was plotted against $fAUC_{350-550}$ and the Pearson correlation between $fAUC_{350-550}$ and $D_{AVGENH}$ was calculated. The obtained results are schematically provided in FIG. 13.

Notably, as clearly appear from FIG. 13, $D_{AVGENH}$ showed statistically significant correlation with $fAUC_{350-550}$ (sloped line p-value<0.01, Pearson Corr. Test) and, hence, with the amount of CTX histologically determined in tissue regions from 350 to 550 µm from the nearest vessel.

A cutoff value of 0.5 for $D_{AVGENH}$ was then selected, corresponding to the hypothetical tumor in which the 50% of all the pixels inside the ROI showed "favorable" physiology. Tumors having a $D_{AVGENH}$ higher than 0.5 were identified as "favorable" or "Permeable", while tumors resulting in lower ratio were defined "unfavorable" or "Non Permeable".

Indeed, as appears from the graph of FIG. 13, "Favorable" tumors (white dots, $D_{AVGENH}$>0.5) showed higher values of $fAUC_{350,550}$ with respect to "Unfavorable" (the vertical line is placed to indicate the cutoff value). This relevant observation provides an indication of the reliability of the proposed method and suggests its effectiveness when used for discriminating oncologic patients.

The invention claimed is:

1. A Dynamic Contrast Enhanced-Magnetic Resonance Imaging (DCE-MRI) method for classifying a tumor or cancerous mass of an oncologic patient prior to treatment with an anticancer therapy comprising:
    a) administering an effective amount of a paramagnetic contrast agent having a molecular weight of 800 to 5000 Da,
    displaying a non-covalent binding with Human Serum Albumin of at least 85%, and comprising (i) at least one paramagnetic complex unit and (ii) at least one lipophilic moiety to the oncologic patient;
    (b) acquiring DCE-MRI images during the passage of the paramagnetic contrast agent within the oncologic patient;
    (c) identifying at least one region of interest within the DCE-MRI images;
    (d) obtaining a signal intensity curve within the at least one region of interest, wherein the signal intensity curve contains a plurality of signal intensity values;
    (e) converting the signal intensity values into contrast agent concentration values;
    (f) drafting a concentration-time curve;
    (g) fitting the concentration curve by a pharmacokinetic model;
    (h) deriving at least one parameter related to the pharmacokinetics displayed by the paramagnetic contrast agent, wherein the at least one parameter is measured, on a pixel-by-pixel or voxel-by-voxel basis, in at least one region of interest within the tumor or cancerous mass and in at least one reference region in the DCE-MRI images;
    (i) calculating a threshold value for the at least one parameter by determining the mean (μ) and standard deviation (σ) of the at least one parameter, on a pixel-by-pixel or voxel-by-voxel basis, in the at least one reference region;
    (j) estimating the delivery of the anticancer therapy within the tumor or cancerous mass of the oncologic patient based on the at least one parameter by calculating a fraction D of pixels or voxels in the at least one region of interest having a value of the at least one parameter that exceeds the threshold value for the at least one parameter; and
    (k) classifying the tumor or cancerous mass of the oncologic patient as resistant or non-resistant to the anticancer therapy based on the fraction D, wherein the fraction D at least equal to 0.5 indicates that the tumor or cancerous mass of the patient is non-resistant to the anticancer therapy and the fraction D less than 0.5 indicates that the tumor or cancerous mass of the patient is resistant to the anticancer therapy, wherein the anticancer therapy is a macromolecular drug or pro-drug having a size comparable to or greater than that of albumin prior to intravenous injection or reaching the size upon intravenous injection, and wherein classification of the tumor or cancerous mass occurs prior to treatment with the anticancer therapy.

2. A DCE-MRI method according to claim 1 wherein the macromolecular drug or pro-drug is an antibody or an antibody fragment-based anticancer drug.

3. A DCE-MRI method according to claim 2 wherein the macromolecular drug or pro-drug is selected from the group consisting of Alemtuzumab, Bevacimmab, Brentuximab Vedotin, Cetuximab, Gemtuzumab, Ipilimumab, Panitumumab, Trastuzumab, Tositumomab and Rituximab.

4. A DCE-MRI method according to claim 1, wherein the at least one parameter is selected from the group consisting of: fractional plasma volume ($f_{PV}$), volume transfer constant between blood plasma and extravascular extracellular space ($K^{trans}$), average signal enhancement (ANVGENH), area under the concentration curve (AUC), area under the signal enhancement curve (AUCE), initial area under the time-concentration curve ($IAUC_T$), initial area under the time-signal enhancement curve ($IAUCE_T$), early AUC ratio (EARLYAUCRATIO), late AUC ratio (LATEAUCRATIO), and combinations thereof.

5. A DCE-MRI method according to claim 4 wherein the at least one parameter is selected from the group consisting of $K^{trans}$ and $f_{PV}$.

6. A DCE-MRI method according to claim 1 wherein the paramagnetic contrast agent has a molecular weight of 800 to 3,000 Da and a terminal half-life value in human blood circulation of at least 4 hours.

7. A DCE-MRI method according to claim 1 wherein the paramagnetic contrast agent displays a non-covalent binding with the Human Serum Albumin higher than 90%.

8. A DCI-MRI method according to claim 1 wherein the paramagnetic contrast agent is a physiologically acceptable salt of a paramagnetic chelated complex selected from the group consisting of: Gadocoletic acid, a gadolinium complex of the MS 325, and a gadolinium complex of the AAZTA-deoxycholic acid.

* * * * *

UNITED STATES PATENT AND TRADEMARK OFFICE
CERTIFICATE OF CORRECTION

PATENT NO. : 9,952,300 B2
APPLICATION NO. : 14/382585
DATED : April 24, 2018
INVENTOR(S) : Giavazzi et al.

Page 1 of 1

It is certified that error appears in the above-identified patent and that said Letters Patent is hereby corrected as shown below:

In the Claims

Column 56, Claim 3, Line 20 "Bevacimmab" should read – Bevacizumab –.

Column 56, Claim 4, Line 27 "ANVGENH" should read – AVGENH –.

Column 56, Claim 8, Line 44 "DCI-MRI" should read – DCE-MRI –.

Signed and Sealed this
Twenty-third Day of April, 2019

Andrei Iancu
*Director of the United States Patent and Trademark Office*